US008796415B2

(12) United States Patent
Debant et al.

(10) Patent No.: US 8,796,415 B2
(45) Date of Patent: Aug. 5, 2014

(54) INHIBITORS OF GUANINE EXCHANGE FACTORS AND THEIR USE AS ANTICANCER DRUGS

(75) Inventors: Anne Debant, Prades-le-Lez (FR); Susanne Schmidt, Montpellier (FR); Nathalie Bouquier, Montpellier (FR); Sylvie Fromont, Montpellier (FR)

(73) Assignees: Centre National de la Recherche Scientifique, Paris (FR); Universite Montpellier 2—Sciences et Techniques, Montpellier (FR)

( * ) Notice: Subject to any disclaimer, the term of this patent is extended or adjusted under 35 U.S.C. 154(b) by 9 days.

(21) Appl. No.: 13/503,092

(22) PCT Filed: Oct. 22, 2009

(86) PCT No.: PCT/IB2009/055230
§ 371 (c)(1),
(2), (4) Date: Jun. 26, 2012

(87) PCT Pub. No.: WO2011/048445
PCT Pub. Date: Apr. 28, 2011

(65) Prior Publication Data
US 2012/0258099 A1 Oct. 11, 2012

(51) Int. Cl.
*A61K 38/00* (2006.01)

(52) U.S. Cl.
USPC .......................... 530/300; 530/324; 530/350

(58) Field of Classification Search
None
See application file for complete search history.

(56) References Cited

U.S. PATENT DOCUMENTS

2006/0210973 A1* 9/2006 Debant et al. .................. 435/6

FOREIGN PATENT DOCUMENTS

| EP | 1367064 A1 | 12/2003 |
|---|---|---|
| WO | 9602561 A1 | 2/1996 |
| WO | 9735979 A1 | 10/1997 |
| WO | 03099778 A2 | 12/2003 |

OTHER PUBLICATIONS

International Search Report, dated Jul. 12, 2010, from corresponding PCT application.
Baines et al., "Peptide aptamers as guides for small-molecule drug discovery", Drug Discovery Today, Apr. 2006, vol. 11, Nos. 7/8, pp. 334-341.
Baldwin et al., "Multiple Microalterations Detected at High Frequency in Oral Cancer", Cancer Research, 2005, vol. 65, No. 17, pp. 7561-7567.
Bellanger et al., "The two guanine nucleotide exchange factor domains of Trio link the Rac1 and the RhoA pathways in vivo", Oncogene, 1998, vol. 16, pp. 147-152.
Bellanger et al., "Different regulation of the Trio Dbl-Homology domains by their associated PH domains", Biology of the Cell, 2003, vol. 95, pp. 625-634.
Blangy et al., "TrioGEF1 controls Rac- and Cdc42-dependent cell structures through the direct activation of RhoG", Journal of Cell Science, 2000, vol. 113, pp. 729-739.
Blangy et al., "Identification of TRIO-GEFD1 chemical inhibitors using the yeast exchange assay", Biology of the Cell, 2006, vol. 98, No. 9, pp. 511-522.
Borghouts et al., "Peptide aptamers: recent developments for cancer therapy", Expert Opin. Biol. Ther., 2005, vol. 5, No. 6, pp. 783-797.
Bos et al., "GEFs and GAPs: Critical Elements in the Control of Small G Proteins", Cell, 2007, vol. 129, pp. 865-877.
Bouquier et al., "Aptamer-Derived Peptides as Potent Inhibitors of the Oncogenic RhoGEF Tgat", Chemistry and Biology, Apr. 24, 2009, vol. 16., pp. 391-400.
Briancon-Marjollet et al., "Trio Mediates Netrin-1-Induced Rac1 Activation in Axon Outgrowth and Guidance", Molecular and Cellular Biology, 2008, vol. 28, No. 7, pp. 2314-2323.
Butz et al., "Induction of apoptosis in human papillomavirus-positive cancer cells by peptide aptamers targeting the viral E6 oncoprotein", PNAS, 2000, vol. 97, No. 12, pp. 6693-6697.
Calaf et al., "Gene and Protein Expressions Induced by 17β-estradiol and Parathion in Cultured Breast Epithelial Cells", Mol Med, 2007, vol. 13, Nos. 5-6, pp. 255-265.
Calaf et al., "Gene Expression Signature of Parathion-transformed human breast epithelial cells", International Journal of Molecular Medicine, 2007, vol. 19, pp. 741-750.
Chhatriwala et al., "The DH and PH Domains of Trio Coordinately Engage Rho GTPases for their Efficient Activation", J. Mol Biol., 2007, vol. 368, No. 5, pp. 1307-1320.
Colas et al., "Genetic Selection of Peptide Aptamers that recognize and inhibit cyclin-dependent kinase 2", Nature, 1996, vol. 380, pp. 548-550.
Crnkovic-Mertens et al., "Induction of apoptosis in tumor cells by siRNA-mediated silencing of the livin/ML-IAP/KIAP gene", Oncogene, 2003, vol. 22, pp. 8330-8336.
Debant et al., "The multidomain protein Trio binds the Lar transmembrane tyrosine phosphatase, contains a protein kinase domain, and has separate rac-specific and rho-specific guanine nucleotide exchange factor domains", Proc. Natl. Acad. Sci., Biochemistry, 1996, vol. 93, pp. 5466-5471.
Desire et al., "RAC1 Inhibition Targets Amyloid Precursor Protein Processing by γ-Secretase and Decreases Aβ Production in Vitro and in Vivo", The Journal of Biological Chemistry, 2005, vol. 280, No. 45, pp. 37516-37525.
Estrach et al., "The Human Rho-GEF Trio and Its Target GTPase RhoG Are Involved in the NGF Pathway, Leading to Neurite Outgrowth", Current Biology, 2002, vol. 12, 99. 307-312.
Etienne-Manneville et al., "Rho GTPases in cell biology", Nature, 2002, vol. 420, pp. 629-635.

(Continued)

*Primary Examiner* — Sean Aeder
*Assistant Examiner* — Julie Wu
(74) *Attorney, Agent, or Firm* — Young and Thompson

(57) ABSTRACT

A peptide including the amino acids sequence $X_9$ CGYX$_{13}$X$_{14}$AX$_{16}$X$_{17}$X$_{18}$MX$_{20}$X$_{21}$X$_{22}$X$_{23}$X$_{24}$X$_{25}$X$_{26}$X$_{27}$ CPLCX$_{32}$X$_{33}$, a nucleic acid coding for the peptide, and/or a recombinant vector including the nucleic acid for the preparation of a drug intended for the treatment of cancer.

5 Claims, 7 Drawing Sheets

(56) References Cited

OTHER PUBLICATIONS

Eva et al., "Isolation of a new human oncogene from a diffuse B-cell lymphoma", 1985, Nature, vol. 316, pp. 273-275.
Fabbrizio et al., "Inhibition of mammalian cell proliferation by genetically selected peptide aptamers that functionally antagonize E2F activity", Oncogene, 1999, vol. 18, pp. 4357-4363.
Forozan et al., "Comparative Genomic Hybridization Analysis of 38 Breast Cancer Cell Lines: A Basis for Interpreting Complementary DNA Microarray Data", Cancer Research, 2000, vol. 60, pp. 4519-4525.
Gao et al., "Rational design and characterization of a Rac GTPase-specific small molecule inhibitor", PNAS, 2004, vol. 101, No. 20, pp. 7618-7623.
Garnis et al., "Chromosome 5p aberrations are early events in lung cancer: implication of glial cell line-derived neurotrophic factor in disease progression", Oncogene, 2005, vol. 24, pp. 4806-4812.
Greenman et al., "Patterns of somatic mutation in human cancer genomes", Nature, 2007, vol. 446, No. 7132, pp. 153-158.
Hafner et al., "Inhibition of cytohesins by SecinH3 leads to hepatic insulin resistance", Nature, vol. 444, pp. 941-944, (2006).
Katzav et al., "vav, a Novel Human Oncogene Derived from a Locus Ubiquitously Expressed in Hematopoietic Cells", The EMBO Journal, 1989, vol. 8, No. 8, pp. 2283-2290.
Kloth et al., "Combined array-comparative genomic hybridization and single-nucleotide polymorphism-loss of heterozygosity analysis reveals complex genetic alterations in cervical cancer", BMC Genomics, 2007, vol. 8, No. 53, pp. 1-13.
Lane et al., "The expression and prognostic value of the guanine nucleotide exchange factors (GEFs) Trio, Vav1 and TIAM-1 in human breast cancer", International Seminars in Surgical Oncology, Oct. 16, 2008, p. 23, vol. 5, No. 1.
Lutz et al., "Structure of Gαq-p63RhoGEF-RhoA Complex Reveals a Pathway for the Activation of RhoA by GPCRs", Science, 2007, vol. 318, pp. 1923-1927.
Martel et al., "p53-dependent inhibition of mammalian cell survival by a genetically selected peptide aptamer that targets the regulatory subunit of protein kinase CK2", Oncogene, 2006, vol. 25, pp. 7343-7353.
Mayer et al., "Controlling small guanine-nucleotide-exchange factor function through cytoplasmic RNA intramers", PNAS, 2001, vol. 98, No. 9, pp. 4961-4965.
Mhawech-Fauceglia et al., "Genetic Alterations in Urothelial Bladder Carcinoma", Cancer, 2006, vol. 106, No. 6, pp. 1205-1216.
Miki et al., "Oncogene ect2 is related to regulators of small GTP-binding proteins", Nature, 1993, vol. 362, pp. 462-465.
Newsome et al., "Trio Combines with Dock to Regulate Pak Activity Pathfinding in *Drosophila*", Cell, 2000, vol. 101, pp. 283-294.
Ng et al., "Gain and overexpression of the oncostatin M receptor occur frequently in cervical squamous cell carcinoma and are associated with adverse clinical outcome", Journal of Pathology, 2007, vol. 212, pp. 325-334.
Nouvion et al., "Modulation of Nr-13 antideath activity by peptide aptamers", Oncogene, 2007, vol. 26, pp. 701-710.
Rojas et al., "Gαq Directly Activates p63RhoGEF and Trio via a Conserved Extension of the Dbl Homology-associated Pleckstrin Homology Domain", J Biol Chem., 2007, vol. 282, No. 40, pp. 1-19.
Rossman et al., "Multifunctional Roles for the PH Domain of Dbs in Regulating Rho GTPase Activation", The Journal of Biological Chemistry, 2003, vol. 278, No. 20, pp. 18393-18400.
Rossman et al., "GEF Means Go: Turning on RHO GTPases With Guanine Nucleotide-Exchange Factors", Nature Reviews, Molecular Cell Biology, 2005, vol. 6, pp. 167-180.
Salhia et al., "The Guanine Nucleotide Exchange Factors Trio, Ect2, and Vav3 Mediate the Invasive Behavior of Glioblastoma", The American Journal of Pathology, 2008, vol. 173, No. 6.
Sardet et al., "E2F-4 and E2F-5, two members of the E2F family, are expressed in the early phases of the cell cycle", Proc. Natl. Acad. Sci, 1995, vol. 92, pp. 2403-2407.

Schmidt et al., "Functional Study of the RHO-GEF Domains of Trio by Selecting Novel Peptide Inhibitors", Biology of the Cell, 2000, vol. 92, No. 2, p. 172, XP001145963.
Schmidt et al., "Identification of the first RHO-GEF inhibitor, TRIPα, which targets the RhoA-specific GEF domain of Trio", FEBS Letters, 2002, vol. 523, pp. 35-42.
Shutes et al., "Specificity and Mechanism of Action of Eht 1864, a Novel Small Molecule Inhibitor of Rac Family Small GTPases", The Journal of Biological Chemistry, 2007, vol. 282, No. 49, pp. 35666-35678.
Sirvent et al., "The tyrosine kinase Abl is required for Src-transforming activity in mouse fibroblasts and human breast cancer cells", Oncogene, 2007, vol. 26, pp. 7313-7323.
Souchet et al., "Human p63RhoGEF, a novel RhoA-specific guanine nucleotide exchange factor, is localized in cardiac sarcomere", Journal of Cell Science, vol. 115, No. 3, pp. 629-640, (2002).
Steven et al., "UNC-73 Activates the Rac GTPase and is Required for Cell and Growth Cone Migrations in C. elegans", Cell, 1998, vol. 92, pp. 785-795.
Toksoz et al., "The Rho Small GTPase: Functions in Health and Disease", Histology Histopathology, 2002, vol. 17, pp. 915-927.
Viaud et al., "Structure-based discovery of an inhibitor of an activation by Sec7 domains through targeting of protein-protein complexes", PNAS, 2007, vol. 104, No. 25, pp. 10370-10375.
Whitehead et al., "Expression Cloning of lfc, a Novel Oncogene with Structural Similarities to Guanine Nucleotide Exchange Factors and to the Regulatory Region of Protein Kinase C", The Journal of Biological Chemistry, 1995, vol. 270, No. 31, pp. 18388-18395.
Whitehead et al., "Expression Cloning of 1se, a Novel Oncogene with Structural Similarities to the Dbl Family of Guanine Nucleotide Exchange Factors", The Journal of Biological Chemistry, 1996, vol. 271, No. 31, pp. 18643-18650.
Yoshizuka et al., "An Alternative Transcript Derived from the Trio Locus Encodes a Guanosine Nucleotide Exchange Factor with Mouse Cell-transforming Potential", The Journal of Biological Chemistry, 2004, vol. 279, No. 42, pp. 43998-44004, XP002588121.
Zeeh et al., "Dual Spedificity of the Interfacial Inhibitor Brefeldin a for an Proteins and Sec7 Domains", The Journal of Biological Chemistry, 2006, vol. 281, No. 17, pp. 11805-11814.
Zheng et al., "Trio Amplification and Abundant mRNA Expression is Associated with Invasive Tumor Growth and Rapid Tumor Cell Proliferation in Urinary Bladder Cancer", American Journal of Pathology, 2004, vol. 165, No. 1, pp. 63-69.
Adamowicz et al., "Frequent Amplifications and Abundant Expression of TRIO, NKD2, and IRX2 in Soft Tissue Sarcomas", Genes, Chromosomes & Cancer, 2006, vol. 45, pp. 829-838.
Bardou et al., "Peptide Aptamers for Small Molecule Drug Discovery", vol. 535, pp. 373-388, Methods in Molecular Biology, 2009.
Bickle et al., "Selection and characterization of large collections of peptide aptamers through optimized yeast two-hybrid procedures", Nature Protocols, 2006, vol. 1, No. 3, pp. 1066-1091.
Borghouts et al., "Current strategies for the development of peptide-based anti-cancer therapeutics", Journal of Peptide Science, 2005, vol. 11, pp. 713-726.
Coe et al., "High-Resolution Chromosome Arm 5p Array CGH Analysis of Small Cell Lung Carcinoma Cell Lines", Genes, Chromosomes & Cancer, 2005, vol. 42, pp. 308-313.
Hoppe-Seyler et al., "Peptide Aptamers: Specific Inhibitors of Protein Function", Current Molecular Medicine, 2004, vol. 4, pp. 529-538.
Mori et al., "Tgat oncoprotein functions as a inhibitor of RECK by association of the unique C-terminal region", Biochemical and Biophysical Research Communications, 2007, vol. 355, pp. 937-943.
Oleksy et al., "Preliminary crystallographic analysis of the complex of the human GTPase RhoA with the DH/PH tandem of PDZ-RhoGEF", Acta Cryst., 2004, D60, pp. 740-742.
Yamada et al., "Tgat, a Rho-specific guanine nucleotide exchange factor, activates NF-kB via physical association with IkB kinase complexes", Biochemical and Biophysical Research Communications, 2007, doi:10.1016/j.bbrc.2007.01.147.

* cited by examiner

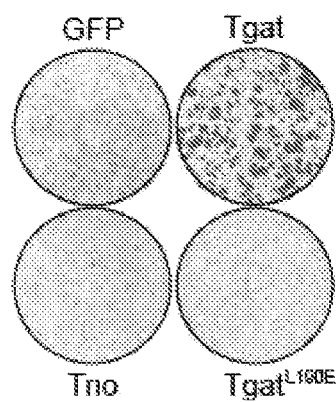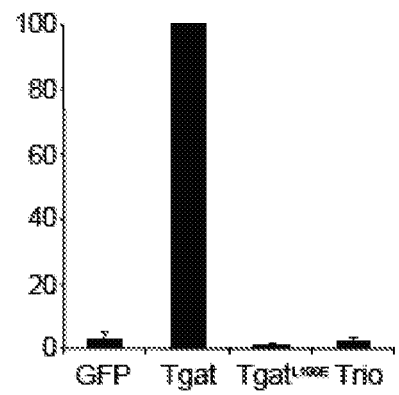
Figure 3A
Figure 3B
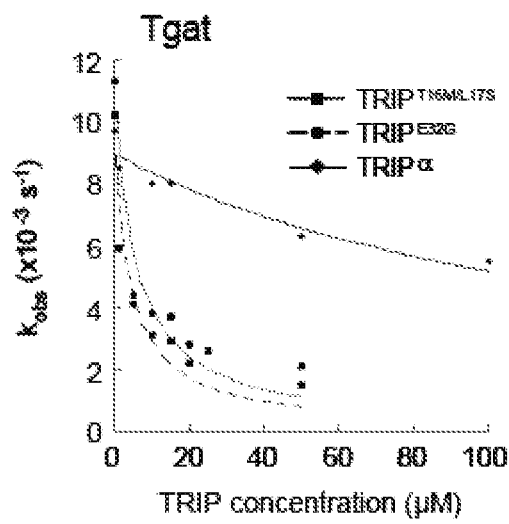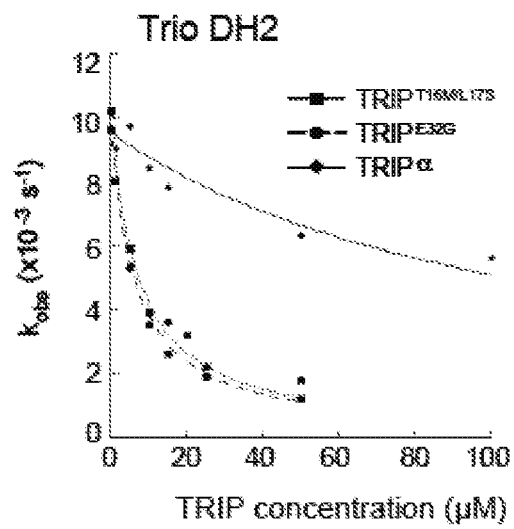
Figure 4

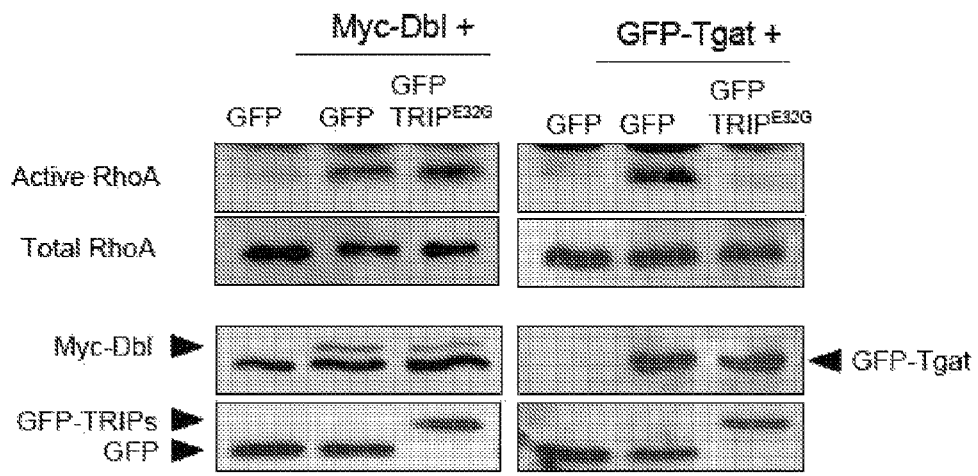
Figures 8
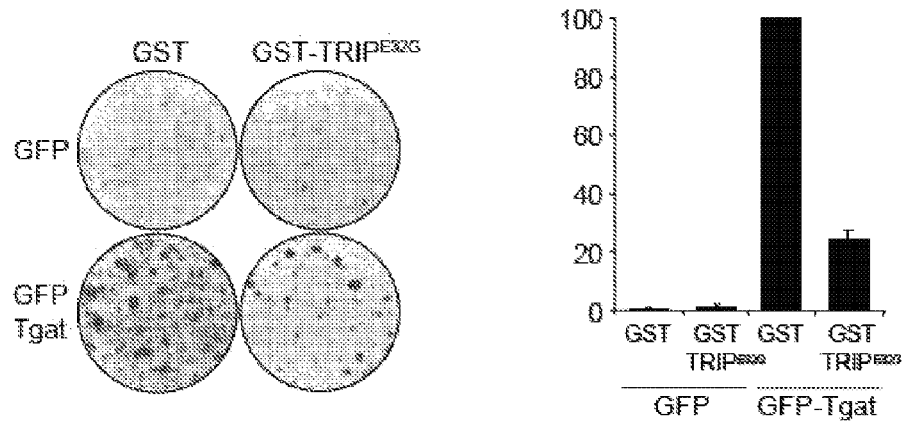
Figures 9A  Figures 9B

INHIBITORS OF GUANINE EXCHANGE FACTORS AND THEIR USE AS ANTICANCER DRUGS

FIELD OF THE INVENTION

The present invention relates to inhibitors of guanine exchange factor, and their use as anticancer drugs.

BACKGROUND OF THE INVENTION

By remodeling the actin cytoskeleton, Rho GTPases regulate various cellular processes, such as proliferation, migration, cell adhesion and cell shape (Etienne-Manneville and Hall, 2002). They are activated by the Dbl family of Rho Guanine Nucleotide Exchange Factors (RhoGEFs), which accelerates their GDP/GTP exchange rate (Rossman et al., 2005). RhoGEFs represent a large family (over seventy members in mammals) of complex proteins with numerous signaling domains, but they almost invariably contain a functional tandem, including a Dbl Homology (DH) domain responsible for guanine nucleotide exchange, followed by a Pleckstrin Homology (PH) domain, which targets the GEF to the plasma membrane and/or regulates nucleotide exchange (Chhatriwala et al., 2007; Lutz et al., 2007; Rojas et al., 2007; Rossman et al., 2003; Rossman et al., 2005). Deregulation of Rho GTPase function has been associated with various human disorders, including cancer and metastasis, (Sahai and Marshall, 2002; Toksoz and Merdek, 2002). Indeed, an increase in RhoGTPase activation due to overexpression of Rac1 or RhoA and C has been associated with tumor proliferation and metastasis. In addition, many Dbl family RhoGEFs have been isolated based on their oncogenic potency, which often results from a truncation of the protein, leading to uncontrolled GEF activity and subsequent aberrant Rho GTPase activation (Eva and Aaronson, 1985; Katzav et al., 1989; Miki et al., 1993; Whitehead et al., 1995; Whitehead et al., 1996).

Trio belongs to the RhoGEF family and is a complex protein harboring two GEF domains (GEFD1 and GEFD2), activating the GTPases Rac1/RhoG and RhoA, respectively, and thus potentially linking several Rho-GTPase signaling pathways in vivo (Blangy et al., 2000; Debant et al., 1996; Bellanger et al., 1998). Studies on invertebrate Trio orthologs have established a central role for Trio in cell migration and axon guidance, mainly through the activation of Rac1 by the GEFD1 domain (Steven et al., 1998; Newsome et al., 2000). Trio knock-out mice are embryonic lethal (E15 to birth) and show defects in brain organization and secondary myogenesis, suggesting a major role for mammalian Trio in these developmental processes (O'Brien et al., 2000). Consistently, we have shown that Trio is required for RhoG-mediated neurite outgrowth in PC12 cells in response to NGF (Estrach et al., 2002) and that Trio is the GEF responsible for Rac1 activation during netrin/DCC-induced axon outgrowth and guidance (Briançon-Marjollet et al., 2008). Recently, an oncogenic isoform of Trio, called Tgat, has been identified from Adult T-Cell Leukemia patient cells and encodes only the RhoA-specific GEF domain. Tgat induces cell transformation and tumor formation in nude mice, mainly via activation of RhoA (Yoshizuka et al., 2004).

Rho GTPases and their GEFs thus represent attractive targets for inhibition, not only to understand their function but also in pathology, to develop anti-cancer drugs.

When trying to inhibit signalling pathways controlled by small G proteins and their activating GEFs, the challenge is that these are not mere enzymes with a well-defined active site that can be blocked. Rather, protein-protein interactions have to be targeted and the lack of reactive pockets to which inhibitors could bind is a challenging issue. This might in part explain why, although oncogenic Ras has been discovered more than 20 years ago, no inhibitor with clinical validation has been identified. Therefore, research has focused on trying to inhibit the guanine nucleotide exchange factors instead, and recent studies report the successful identification of such inhibitors.

For instance, the international application WO/2003/099778 discloses a peptide inhibitor that specifically inhibits the Trio GEFD2 domain, and its use for modulating axon retraction.

However, to date, only one specific inhibitor of GEFD2 domain of Trio has been described, but said inhibitor has never been used for treating other pathologies than neural retraction.

Thus, there is a need to provide new inhibitors that can be used in cancer therapy that selectively inhibit specific GEF domains.

SUMMARY OF THE INVENTION

One aim of the invention is to provide new peptides for treating cancer, or alternatively nucleic acid sequences coding said peptides.

Another aim of the invention is to provide peptides inhibiting Rho-GEF protein with a high efficiency.

Another aim of the invention is to provide specific in vivo inhibitors of a Rho-GEF family member, and their oncogenic forms.

Another aim of the invention is to provide specific in vivo inhibitors of a Rho-GEF family member, blocking specifically the RhoA pathway.

Still another aim of the invention is to provide pharmaceutical compositions for treating cancer.

DETAILED DESCRIPTION OF THE INVENTION

The invention relates to the use of a peptide, possibly at least one peptide, comprising or consisting of the following amino acid sequence SEQ ID NO: 2, Nter-$X_9$CGY$X_{13}X_{14}$A$X_{16}X_{17}X_{18}$M$X_{20}X_{21}X_{22}X_{23}X_{24}X_{25}X_{26}$ $X_{27}$CPLC$X_{32}X_{33}$-Cter wherein bold underlined amino acids represent essential amino acids for the activity of said peptide, and wherein $X_9$, $X_{13}$, $X_{14}$, $X_{16}$, $X_{17}$, $X_{18}$, $X_{20}$, $X_{21}$, $X_{22}$, $X_{23}$, $X_{24}$, $X_{25}$, $X_{26}$, $X_{27}$, $X_{32}$ and $X_{33}$ represent any amino acids, with the proviso that said peptide does not comprise or consist of the amino acid sequence SEQ ID NO: 1, for the preparation of a drug intended for the treatment of cancer.

The peptides according to the invention are able to specifically inhibit the RhoA GEF activity of Trio and the RhoA GEF activity of the oncogenic form of Trio, i.e. Tgat. Tgat retains only the RhoA-specific DH2 domain of Trio and, instead of the associated PH2 domain, carries a unique C-terminal sequence of 15 amino acids, not found in Trio. Said peptides have inhibiting properties at least 2 fold, preferably 3 fold, more preferably 5 fold higher compared to the inhibiting activity of TRIPα (SEQ ID NO: 197).

The peptide TRIPα consisting of the amino acid sequence SEQ ID NO: 197 comprises the peptide consisting of the amino acid sequence SEQ ID NO: 1, excluded from the object of the invention. SEQ ID NO 1 corresponds to the peptidic sequence delimited by the amino acids from the position 9 to the position 33 of TRIPα.

The invention also relates to a method for treating cancer, comprising the administration to a person in a need thereof of a pharmaceutically effective amount of a peptide comprising or consisting of the following amino acids sequence SEQ ID NO: 2, $$X_9\textbf{\underline{CGY}}X_{13}X_{14}\textbf{\underline{A}}X_{16}X_{17}X_{18}\textbf{\underline{M}}X_{20}X_{21}X_{22}X_{23}X_{24}X_{25}X_{26}X_{27}\textbf{\underline{CPLC}}$$
$$X_{32}X_{33}$$

wherein bold underlined amino acids represent essential amino acids for the activity of said peptide, and wherein $X_9$, $X_{13}$, $X_{14}$, $X_{16}$, $X_{17}$, $X_{18}$, $X_{20}$, $X_{21}$, $X_{22}$, $X_{23}$, $X_{24}$, $X_{25}$, $X_{26}$, $X_{27}$, $X_{32}$ and $X_{33}$ represent any amino acids, said peptide being able to specifically inhibit the RhoA GEF activity of Trio and the RhoA GEF activity of the oncogenic form of Trio, i.e. Tgat, said peptide having inhibiting properties at least 2 fold, preferably 3 fold, more preferably 5 fold higher compared to the inhibiting activity of TRIPα.

with the proviso that said peptide does not comprise or consist of the amino acid sequence SEQ ID NO: 1.

The present invention is based on the unexpected observation made by the Inventors that the peptides according to the invention are able to inhibit Tgat, an oncogenic isoform of Trio, and have an inhibitory effect similar to or higher than the inhibitory effect of TRIPα represented by the amino acid sequence SEQ ID NO:1.

According to the invention, the amino acid residues represented by $X_9$, $X_{13}$, $X_{14}$, $X_{16}$, $X_{17}$, $X_{18}$, $X_{20}$, $X_{21}$, $X_{22}$, $X_{23}$, $X_{24}$, $X_{25}$, $X_{26}$, $X_{27}$, $X_{32}$ and $X_{33}$ represent "any amino acid". This means that $X_9$, $X_{13}$, $X_{14}$, $X_{16}$, $X_{17}$, $X_{18}$, $X_{20}$, $X_{21}$, $X_{22}$, $X_{23}$, $X_{24}$, $X_{25}$, $X_{26}$, $X_{27}$, $X_{32}$ and $X_{33}$ can be any of the twenty natural amino acids, or any non-natural amino acid commonly used by a skilled person.

All the peptides according to the invention are able to specifically inhibit Trio GEFD2 domain which means that said peptides inhibit only the TrioGEFD2 domain of Trio and have neither effect on the activity of Trio GEFD1 domain, nor effect on the activity of other GEF domains contained in GEF proteins such as p63RhoGEF, p115RhoGEF, Lbc, Vav, or Dbl. In other words, the peptides according to the invention inhibit only the RhoA GEF domain (GEFD2) contained in Trio and Tgat.

Moreover, the GEFD2 domain of Trio contained in Tgat oncoprotein is also a target of the peptides according to the invention, and said Tgat GEF domain is inhibited by said peptides.

Also, the peptides according to the invention have an increased inhibitory efficiency of the GEF activity of both Trio GEFD2 and Tgat, compared to TRIPα (SEQ ID NO: 197), or its active fragments (for instance fragment 9-33 of TRIPα as set forth by SEQ ID NO: 1). The following properties of the peptides according to the invention have been demonstrated:

first, the underlined bold residues are essential for the inhibitory activity of said peptides, as determined by ALA-Scan (see example section)

second, some variation in other amino acids can enhance significantly the inhibitory efficiency of said peptides.

The determination of the inhibitory efficiency of the peptides according to the invention on the exchange activity of the GEFD2 domain of Trio and of Tgat, as well as their in vitro and in vivo activities, are illustrated in the Example section hereafter.

The peptides according to the invention are artificial, isolated, purified, and have never been described in the art, prior to the characterization by the Inventors.

Another advantageous embodiment of the invention relates to the above-mentioned method or use, wherein said peptide comprises or consists of the amino acid sequence SEQ ID NO: 3, $$I\textbf{\underline{CGY}}X_{13}L\textbf{\underline{A}}X_{16}X_{17}X_{18}\textbf{\underline{M}}LGPX_{23}X_{24}RVX_{27}\textbf{\underline{CPLC}}X_{32}P$$

wherein bold underlined amino acids represent essential amino acids for the activity of said peptide, and wherein $X_{13}$, $X_{16}$, $X_{17}$, $X_{18}$, $X_{23}$, $X_{24}$, $X_{27}$ and $X_{32}$ represent any amino acids, said peptide being able to specifically inhibit the RhoA GEF activity of Trio and the RhoA GEF activity of the oncogenic form of Trio, i.e. Tgat, said peptide having inhibiting properties at least 2 fold, preferably 3 fold, more preferably 5 fold higher compared to the inhibiting activity of TRIPα.

with the proviso that said amino acids sequence does not comprises or consist of the amino acids sequence SEQ ID NO: 1.

The invention relates, in one other advantageous embodiment, to the above-mentioned method or use, wherein said peptide comprises or consists of the amino acid sequence SEQ ID NO: 3 having at least one of the following features:

$X_{13}$ is D,
$X_{16}$ is M or A,
$X_{17}$ is S,
$X_{18}$ is D, G or A,
$X_{23}$ is G,
$X_{24}$ is A,
$X_{27}$ is L, and
$X_{32}$ is G.

According to the invention, the peptide comprising or consisting of the amino acid sequence SEQ ID NO: 3 can be for instance the peptide SEQ ID NO: 3 wherein $X_{13}$ is D, and $X_{16}$, $X_{17}$, $X_{18}$, $X_{23}$, $X_{24}$, $X_{27}$ and $X_{32}$ represent any amino acid, or the peptide SEQ ID NO: 3 wherein $X_{13}$ is D, $X_{17}$ is S, and $X_{16}$, $X_{18}$, $X_{23}$, $X_{24}$, $X_{27}$ and $X_{32}$ represent any amino acid, . . . .

The skilled person would easily reproduce all the peptides according to the invention, taking into account the above mentioned conditions regarding the definitions of amino acid residues $X_{13}$, $X_{16}$, $X_{17}$, $X_{18}$, $X_{23}$, $X_{24}$, $X_{27}$ and $X_{32}$.

The invention relates, in one other advantageous embodiment, to the above-mentioned method or use, wherein said peptide comprises or consists of the amino acid sequences chosen among the group comprising SEQ ID NO: 4 to SEQ ID NO: 51.

For instance, the peptides consisting of the amino acid sequences SEQ ID NO: 4 to SEQ ID NO: 15 are specifically defined hereafter.

The peptide consisting in the amino acid sequence SEQ ID NO: 4 corresponds to the amino acid sequence SEQ ID NO: 3, wherein $X_{13}$ is N, $X_{16}$ is T, $X_{17}$ is L, $X_{18}$ is V, $X_{23}$ is 5, $X_{24}$ is E, $X_{27}$ is F, and $X_{32}$ is G.

The peptide consisting in the amino acid sequence SEQ ID NO: 5 corresponds to the amino acid sequence SEQ ID NO: 3, wherein $X_{13}$ is N, $X_{16}$ is M, $X_{17}$ is 5, $X_{18}$ is V, $X_{23}$ is 5, $X_{24}$ is E, $X_{27}$ is F, and $X_{32}$ is E.

The peptide consisting in the amino acid sequence SEQ ID NO: 6 corresponds to the amino acid sequence SEQ ID NO: 3, wherein $X_{13}$ is N, $X_{16}$ is M, $X_{17}$ is L, $X_{18}$ is V, $X_{23}$ is S, $X_{24}$ is E, $X_{27}$ is F, and $X_{32}$ is E.

The peptide consisting in the amino acid sequence SEQ ID NO: 7 corresponds to the amino acid sequence SEQ ID NO: 3, wherein $X_{13}$ is N, $X_{16}$ is T, $X_{17}$ is S, $X_{18}$ is V, $X_{23}$ is S, $X_{24}$ is E, $X_{27}$ is F, and $X_{32}$ is E.

The peptide consisting in the amino acid sequence SEQ ID NO: 8 corresponds to the amino acid sequence SEQ ID NO: 3, wherein $X_{13}$ is N, $X_{16}$ is M, $X_{17}$ is L, $X_{18}$ is V, $X_{23}$ is G, $X_{24}$ is E, $X_{27}$ is F, and $X_{32}$ is E.

The peptide consisting in the amino acid sequence SEQ ID NO: 9 corresponds to the amino acid sequence SEQ ID NO: 3, wherein $X_{13}$ is N, $X_{16}$ is T, $X_{17}$ is L, $X_{18}$ is D, $X_{23}$ is S, $X_{24}$ is E, $X_{27}$ is L, and $X_{32}$ is E.

The peptide consisting in the amino acid sequence SEQ ID NO: 10 corresponds to the amino acid sequence SEQ ID NO: 3, wherein $X_{13}$ is N, $X_{16}$ is T, $X_{17}$ is L, $X_{18}$ is V, $X_{23}$ is S, $X_{24}$ is E, $X_{27}$ is F, and $X_{32}$ is G.

The peptide consisting in the amino acid sequence SEQ ID NO: 11 corresponds to the amino acid sequence SEQ ID NO: 3, wherein $X_{13}$ is N, $X_{16}$ is A $X_{17}$ is L, $X_{18}$ is G, $X_{23}$ is S, $X_{24}$ is E, $X_{27}$ is F, and $X_{32}$ is G.

The peptide consisting in the amino acid sequence SEQ ID NO: 12 corresponds to the amino acid sequence SEQ ID NO: 3, wherein $X_{13}$ is N, $X_{16}$ is T, $X_{17}$ is L, $X_{18}$ is A, $X_{23}$ is S, $X_{24}$ is A, $X_{27}$ is F, and $X_{32}$ is G.

The peptide consisting in the amino acid sequence SEQ ID NO: 13 corresponds to the amino acid sequence SEQ ID NO: 3, wherein $X_{13}$ is D, $X_{16}$ is M, $X_{17}$ is L, $X_{18}$ is V, $X_{23}$ is S, $X_{24}$ is E, $X_{27}$ is F, and $X_{32}$ is E.

The peptide consisting in the amino acid sequence SEQ ID NO: 14 corresponds to the amino acid sequence SEQ ID NO: 3, wherein $X_{13}$ is N, $X_{16}$ is A, $X_{17}$ is S, $X_{18}$ is V, $X_{23}$ is S, $X_{24}$ is E, $X_{27}$ is F, and $X_{32}$ is E.

The peptide consisting in the amino acid sequence SEQ ID NO: 15 corresponds to the amino acid sequence SEQ ID NO: 3, wherein $X_{13}$ is N, $X_{16}$ is T, $X_{17}$ is L, $X_{18}$ is D, $X_{23}$ is S, $X_{24}$ is E, $X_{27}$ is F, and $X_{32}$ is E.

In one other advantageous embodiment, the invention relates to the use or the method mentioned-above, wherein said peptide comprises or consists of the amino acid sequences chosen among the group comprising SEQ ID NO: 4 to SEQ ID NO: 10, SEQ ID NO: 16 to SEQ ID NO: 21, SEQ ID NO: 28 to SEQ ID NO: 34 and SEQ ID NO: 40 to SEQ ID NO: 46.

In one other advantageous embodiment, the invention relates to the use or the method mentioned-above, wherein said peptide comprises or consists of the amino acid sequences chosen among the group comprising SEQ ID NO: 4 to SEQ ID NO: 6, SEQ ID NO: 16 to SEQ ID NO: 18, SEQ ID NO: 28 to SEQ ID NO: 30 and SEQ ID NO: 40 to SEQ ID NO: 42.

Peptides defined above, and consisting of the amino acid sequences SEQ ID NO: 4 to SEQ ID NO: 6, SEQ ID NO: 16 to SEQ ID NO: 18, SEQ ID NO: 28 to SEQ ID NO: 30 and SEQ ID NO: 40 to SEQ ID NO: 42 are such that:

the peptide consisting of the amino acid sequence SEQ ID NO: 40 corresponds to the peptide consisting in the amino acid sequence SEQ ID NO: 197 in which the Glutamate (E) in position 32 is substituted by a Glycine (G), the peptide consisting of the amino acid sequence SEQ ID NO: 41 corresponds to the peptide consisting in the amino acid sequence SEQ ID NO: 197 in which the Threonine (T) in position 16 is substituted by a Methionine (M), and the Leucine (L) in position 17 is substituted by a Serine (S), the peptide consisting of the amino acid sequence SEQ ID NO: 42 corresponds to the peptide consisting in the amino acid sequence SEQ ID NO: 197 in which the Leucine (L) in position 17 is substituted by a Serine (S), the peptide consisting of the amino acid sequence SEQ ID NO: 4 corresponds to a fragment delimited by the amino acids from the position 9 to the position 33 of the amino acid sequence SEQ ID NO: 40, the peptide consisting of the amino acid sequence SEQ ID NO: 5 corresponds to a fragment delimited by the amino acids from the position 9 to the position 33 of the amino acid sequence SEQ ID NO: 41, the peptide consisting of the amino acid sequence SEQ ID NO: 6 corresponds to a fragment delimited by the amino acids from the position 9 to the position 33 of the amino acid sequence SEQ ID NO: 42, the peptide consisting of the amino acid sequence SEQ ID NO: 16 corresponds to a fragment delimited by the amino acids from the position 1 to the position 33 of the amino acid sequence SEQ ID NO: 40, the peptide consisting of the amino acid sequence SEQ ID NO: 17 corresponds to a fragment delimited by the amino acids from the position 1 to the position 33 of the amino acid sequence SEQ ID NO: 41, the peptide consisting of the amino acid sequence SEQ ID NO: 18 corresponds to a fragment delimited by the amino acids from the position 1 to the position 33 of the amino acid sequence SEQ ID NO: 42, the peptide consisting of the amino acid sequence SEQ ID NO: 28 corresponds to a fragment delimited by the amino acids from the position 9 to the position 42 of the amino acid sequence SEQ ID NO: 40, the peptide consisting of the amino acid sequence SEQ ID NO: 29 corresponds to a fragment delimited by the amino acids from the position 9 to the position 42 of the amino acid sequence SEQ ID NO: 41, the peptide consisting of the amino acid sequence SEQ ID NO: 30 corresponds to a fragment delimited by the amino acids from the position 9 to the position 42 of the amino acid sequence SEQ ID NO: 42.

In one another preferred embodiment, the invention relates to the above-defined use or method, wherein said peptide contains flanking parts consisting of fragments of thioredoxin A.

The peptides according to the invention can be inserted into the active site (residue 35) of the *E. coli* thioredoxin A, as disclosed in Colas et al. [Colas et al. 1996, *Nature* 380, 548-50] and the international application n° WO 96/02561.

*E. coli* thioredoxin A is a small, very stable protein which can be produced at high levels. Thioredoxin contains a Cys-Cys active loop where peptides can be inserted and subjected to conformational constraint, since both cysteines can form a disulphide bond under appropriate conditions.

The expression "flanking parts consisting of fragments of the thioredoxin" can mean either that the N-terminal and C-terminal flanking parts when considered together correspond to the complete sequence of thioredoxin (in such a case the above-mentioned amino sequences are inserted in thioredoxin), or that the N-terminal and C-terminal flanking parts are themselves fragments of thioredoxin, the size of said fragment advantageously being from about 20 to about 60 amino acids.

In still another advantageous embodiment, the invention relates to the above-mentioned use or method, wherein said peptide comprises or consists in the amino acid sequences selected from SEQ ID NO: 52 to SEQ ID NO: 99.

The peptides consisting of SEQ ID NO: 52 to SEQ ID NO: 99 correspond respectively to the peptides consisting of SEQ ID NO: 4 to SEQ ID NO: 51 inserted between the amino acid at the position 35 and 36 of the *E. coli* Thioredoxin A.

In another advantageous embodiment, the invention relates to the use or the method previously defined wherein said cancer comprises leukemia, including T-cell acute Leukemia, sarcoma, lung cancer and breast cancer.

All the above cancers concern abnormal proliferation, differentiation, migration of cells that abnormally express Trio protein, for instance by gene amplification, translocation or transcriptional deregulation, or express an abnormal Trio protein form, for instance an "activated" mutant of Trio, due to a point mutation, or due to aberrant alternative splicing, generating an oncogenic isoform such as Tgat.

The invention also relates to an isolated peptide comprising or consisting of the amino acid sequence SEQ ID NO: 3, $$I\underline{\mathbf{CGY}}X_{13}L\underline{\mathbf{A}}X_{16}X_{17}X_{18}\underline{\mathbf{ML}}GPX_{23}X_{24}RVX_{27}\underline{\mathbf{CPLC}}X_{32}P$$

wherein bold underlined amino acids represent essential amino acids for the activity of said peptide, and wherein $X_{13}$, $X_{16}$, $X_{17}$, $X_{18}$, $X_{23}$, $X_{24}$, $X_{27}$ and $X_{32}$ represent any amino acids, said peptide being able to specifically inhibit the RhoA GEF activity of Trio and the RhoA GEF activity of the oncogenic form of Trio, i.e. Tgat, said peptide having inhibiting properties at least 2 fold preferably 3 fold, more preferably 5 fold higher compared to the inhibiting activity of TRIPα with the proviso that said amino acid sequence does not comprise or consist of the amino acid sequence SEQ ID NO: 1.

The above peptides are novel, and have never been referenced in any protein data bases known by the skilled person.

These peptides can be prepared by adapting common protocols known by a skilled person, such as described in the examples section, preferentially by site directed mutagenesis, or by random PCR-based mutagenesis.

In one advantageous embodiment, the invention relates to the isolated peptide previously defined, wherein said peptide comprises or consists of the amino acid sequence SEQ ID NO: 3 having at least one of the following features: $X_{13}$ is D, $X_{16}$ is M or A, $X_{17}$ is 5, $X_{18}$ is D, G or A, $X_{23}$ is G, $X_{24}$ is A, $X_{27}$ is L, and $X_{32}$ is G.

In one advantageous embodiment, the invention relates to the isolated peptide previously defined, wherein said peptide comprises or consists of the amino acid sequences chosen among the group comprising SEQ ID NO: 4 to SEQ ID NO: 51.

In one advantageous embodiment, the invention relates to the isolated peptide previously defined, wherein said peptide contains flanking parts consisting of fragments of the thioredoxin A.

In one advantageous embodiment, the invention relates to the isolated peptide previously defined, wherein said peptide comprises or consists in the amino acid sequences selected from SEQ ID NO: 52 to SEQ ID NO: 99.

The following table 1 recapitulates the correspondence between the peptides according to the invention:

TABLE 1 correspondence between peptides according to the invention.

| SEQ ID NO: 197 (TRIP α) Peptide derived from TRIPα 1-42 | SEQ ID NO: 1 (TRIPα 9-33) Corresponding fragments 9-33 | Corresponding fragments 1-33 | Corresponding fragments 9-42 |
| --- | --- | --- | --- |
| SEQ ID NO: 40 | SEQ ID NO: 4 | SEQ ID NO: 16 | SEQ ID NO: 28 |
| SEQ ID NO: 41 | SEQ ID NO: 5 | SEQ ID NO: 17 | SEQ ID NO: 29 |
| SEQ ID NO: 42 | SEQ ID NO: 6 | SEQ ID NO: 18 | SEQ ID NO: 30 |
| SEQ ID NO: 43 | SEQ ID NO: 7 | SEQ ID NO: 19 | SEQ ID NO: 31 |
| SEQ ID NO: 44 | SEQ ID NO: 8 | SEQ ID NO: 20 | SEQ ID NO: 32 |
| SEQ ID NO: 45 | SEQ ID NO: 9 | SEQ ID NO: 21 | SEQ ID NO: 33 |
| SEQ ID NO: 46 | SEQ ID NO: 10 | SEQ ID NO: 22 | SEQ ID NO: 34 |
| SEQ ID NO: 47 | SEQ ID NO: 11 | SEQ ID NO: 23 | SEQ ID NO: 35 |
| SEQ ID NO: 48 | SEQ ID NO: 12 | SEQ ID NO: 24 | SEQ ID NO: 36 |
| SEQ ID NO: 49 | SEQ ID NO: 13 | SEQ ID NO: 25 | SEQ ID NO: 37 |
| SEQ ID NO: 50 | SEQ ID NO: 14 | SEQ ID NO: 26 | SEQ ID NO: 38 |
| SEQ ID NO: 51 | SEQ ID NO: 15 | SEQ ID NO: 27 | SEQ ID NO: 39 |

The Invention also relates to an isolated nucleic acid comprising or consisting of a nucleic acid sequence coding for a peptide as previously defined.

The Invention also relates to an isolated nucleic acid comprising or consisting of a nucleic acid sequence coding for a peptide, an isolated peptide, comprising or consisting of the amino acid sequence SEQ ID NO: 3, $$I\underline{\mathbf{CGY}}X_{13}L\underline{\mathbf{A}}X_{16}X_{17}X_{18}\underline{\mathbf{ML}}GPX_{23}X_{24}RVX_{27}\underline{\mathbf{CPLC}}X_{32}P$$

wherein bold underlined amino acids represent essential amino acids for the activity of said peptide, and wherein $X_{13}$, $X_{16}$, $X_{17}$, $X_{18}$, $X_{23}$, $X_{24}$, $X_{27}$ and $X_{32}$ represent any amino acids, said peptide being able to specifically inhibit the RhoA GEF activity of Trio and the RhoA GEF activity of the oncogenic form of Trio, i.e. Tgat, said peptide having inhibiting properties at least 2 fold, preferably 3 fold, more preferably 5 fold higher compared to the inhibiting activity of TRIPα (SEQ ID NO:197)

with the proviso that said amino acid sequence does not comprise or consist of the amino acid sequence SEQ ID NO: 1.

In one advantageous embodiment, the invention relates to an isolated nucleic acid as defined above, comprising or consisting of a nucleic acid sequence selected from SEQ ID NO: 100 to SEQ ID NO: 196.

The following table 2 recapitulates the correspondence between the nucleic acid molecules according to the invention and their corresponding peptides which are encoded by them:

TABLE 2

Correspondences between nucleic acid sequences and amino acid sequences.

| peptide consisting of: | is coded by the nucleic acid consisting of: |
|---|---|
| SEQ ID NO: 3 | SEQ ID NO: 100 |
| SEQ ID NO: 4 | SEQ ID NO: 101 |
| SEQ ID NO: 5 | SEQ ID NO: 102 |
| SEQ ID NO: 6 | SEQ ID NO: 103 |
| SEQ ID NO: 7 | SEQ ID NO: 104 |
| SEQ ID NO: 8 | SEQ ID NO: 105 |
| SEQ ID NO: 9 | SEQ ID NO: 106 |
| SEQ ID NO: 10 | SEQ ID NO: 107 |
| SEQ ID NO: 11 | SEQ ID NO: 108 |
| SEQ ID NO: 12 | SEQ ID NO: 109 |
| SEQ ID NO: 13 | SEQ ID NO: 110 |
| SEQ ID NO: 14 | SEQ ID NO: 111 |
| SEQ ID NO: 15 | SEQ ID NO: 112 |
| SEQ ID NO: 16 | SEQ ID NO: 113 |
| SEQ ID NO: 17 | SEQ ID NO: 114 |
| SEQ ID NO: 18 | SEQ ID NO: 115 |
| SEQ ID NO: 19 | SEQ ID NO: 116 |
| SEQ ID NO: 20 | SEQ ID NO: 117 |
| SEQ ID NO: 21 | SEQ ID NO: 118 |
| SEQ ID NO: 22 | SEQ ID NO: 119 |
| SEQ ID NO: 23 | SEQ ID NO: 120 |
| SEQ ID NO: 24 | SEQ ID NO: 121 |
| SEQ ID NO: 25 | SEQ ID NO: 122 |
| SEQ ID NO: 26 | SEQ ID NO: 123 |
| SEQ ID NO: 27 | SEQ ID NO: 124 |
| SEQ ID NO: 28 | SEQ ID NO: 125 |
| SEQ ID NO: 29 | SEQ ID NO: 126 |
| SEQ ID NO: 30 | SEQ ID NO: 127 |
| SEQ ID NO: 31 | SEQ ID NO: 128 |
| SEQ ID NO: 32 | SEQ ID NO: 129 |
| SEQ ID NO: 33 | SEQ ID NO: 130 |
| SEQ ID NO: 34 | SEQ ID NO: 131 |
| SEQ ID NO: 35 | SEQ ID NO: 132 |
| SEQ ID NO: 36 | SEQ ID NO: 133 |
| SEQ ID NO: 37 | SEQ ID NO: 134 |
| SEQ ID NO: 38 | SEQ ID NO: 135 |
| SEQ ID NO: 39 | SEQ ID NO: 136 |
| SEQ ID NO: 40 | SEQ ID NO: 137 |
| SEQ ID NO: 41 | SEQ ID NO: 138 |
| SEQ ID NO: 42 | SEQ ID NO: 139 |
| SEQ ID NO: 43 | SEQ ID NO: 140 |
| SEQ ID NO: 44 | SEQ ID NO: 141 |
| SEQ ID NO: 45 | SEQ ID NO: 142 |
| SEQ ID NO: 46 | SEQ ID NO: 143 |
| SEQ ID NO: 47 | SEQ ID NO: 144 |
| SEQ ID NO: 48 | SEQ ID NO: 145 |
| SEQ ID NO: 49 | SEQ ID NO: 146 |
| SEQ ID NO: 50 | SEQ ID NO: 147 |
| SEQ ID NO: 51 | SEQ ID NO: 148 |
| SEQ ID NO: 52 | SEQ ID NO: 149 |
| SEQ ID NO: 53 | SEQ ID NO: 150 |
| SEQ ID NO: 54 | SEQ ID NO: 151 |
| SEQ ID NO: 55 | SEQ ID NO: 152 |
| SEQ ID NO: 56 | SEQ ID NO: 153 |
| SEQ ID NO: 57 | SEQ ID NO: 154 |
| SEQ ID NO: 58 | SEQ ID NO: 155 |
| SEQ ID NO: 59 | SEQ ID NO: 156 |
| SEQ ID NO: 60 | SEQ ID NO: 157 |
| SEQ ID NO: 61 | SEQ ID NO: 158 |
| SEQ ID NO: 62 | SEQ ID NO: 159 |
| SEQ ID NO: 63 | SEQ ID NO: 160 |
| SEQ ID NO: 64 | SEQ ID NO: 161 |
| SEQ ID NO: 65 | SEQ ID NO: 162 |
| SEQ ID NO: 66 | SEQ ID NO: 163 |
| SEQ ID NO: 67 | SEQ ID NO: 164 |
| SEQ ID NO: 68 | SEQ ID NO: 165 |
| SEQ ID NO: 69 | SEQ ID NO: 166 |
| SEQ ID NO: 70 | SEQ ID NO: 167 |
| SEQ ID NO: 71 | SEQ ID NO: 168 |
| SEQ ID NO: 72 | SEQ ID NO: 169 |
| SEQ ID NO: 73 | SEQ ID NO: 170 |
| SEQ ID NO: 74 | SEQ ID NO: 171 |
| SEQ ID NO: 75 | SEQ ID NO: 172 |
| SEQ ID NO: 76 | SEQ ID NO: 173 |
| SEQ ID NO: 77 | SEQ ID NO: 174 |
| SEQ ID NO: 78 | SEQ ID NO: 175 |
| SEQ ID NO: 79 | SEQ ID NO: 176 |
| SEQ ID NO: 80 | SEQ ID NO: 177 |
| SEQ ID NO: 81 | SEQ ID NO: 178 |
| SEQ ID NO: 82 | SEQ ID NO: 179 |
| SEQ ID NO: 83 | SEQ ID NO: 180 |
| SEQ ID NO: 84 | SEQ ID NO: 181 |
| SEQ ID NO: 85 | SEQ ID NO: 182 |
| SEQ ID NO: 86 | SEQ ID NO: 183 |
| SEQ ID NO: 87 | SEQ ID NO: 184 |
| SEQ ID NO: 88 | SEQ ID NO: 185 |
| SEQ ID NO: 89 | SEQ ID NO: 186 |
| SEQ ID NO: 90 | SEQ ID NO: 187 |
| SEQ ID NO: 91 | SEQ ID NO: 188 |
| SEQ ID NO: 92 | SEQ ID NO: 189 |
| SEQ ID NO: 93 | SEQ ID NO: 190 |
| SEQ ID NO: 94 | SEQ ID NO: 191 |
| SEQ ID NO: 95 | SEQ ID NO: 192 |
| SEQ ID NO: 96 | SEQ ID NO: 193 |
| SEQ ID NO: 97 | SEQ ID NO: 194 |
| SEQ ID NO: 98 | SEQ ID NO: 195 |
| SEQ ID NO: 99 | SEQ ID NO: 196 |

The Invention also relates to a recombinant vector, especially a plasmid, a cosmid, a phage or a DNA virus, containing a nucleotide sequence as defined above, more preferably containing a nucleotide sequence coding for a peptide, especially an isolated peptide, comprising or consisting of the amino acid sequence SEQ ID NO: 3, ICGYX$_{13}$LAX$_{16}$X$_{17}$X$_{18}$MLGPX$_{23}$X$_{24}$RVX$_{27}$CPLCX$_{32}$P wherein bold underlined amino acids represent essential amino acids for the activity of said peptide, and wherein X$_{13}$, X$_{16}$, X$_{17}$, X$_{18}$, X$_{23}$, X$_{24}$, X$_{27}$ and X$_{32}$ represent any amino acids, said peptide being able to specifically inhibit the RhoA GEF activity of Trio and the RhoA GEF activity of the oncogenic form of Trio, i.e. Tgat, said peptide having inhibiting properties at least 2 fold, preferably 3 fold, more preferably 5 fold higher compared to the inhibiting activity of TRIPα (SEQ ID NO:197)

with the proviso that said amino acid sequence does not comprise or consist of the amino acid sequence SEQ ID NO: 1.

In one advantageous embodiment, the invention relates to the recombinant vector previously defined, containing the elements necessary for the expression in a host cell of the polypeptides, or peptide, coded by the nucleic acids above defined, inserted in said vector.

In one advantageous embodiment, the invention relates to the recombinant vector previously defined, containing the elements necessary for the expression in a host cell of the polypeptides, or peptide, coded by the nucleic acid sequence coding for a peptide, an isolated peptide, comprising or consisting of the amino acid sequence SEQ ID NO: 3, ICGYX$_{13}$LAX$_{16}$X$_{17}$X$_{18}$MLGPX$_{23}$X$_{24}$RVX$_{27}$CPLCX$_{32}$P wherein bold underlined amino acids represent essential amino acids for the activity of said peptide, and wherein X$_{13}$, X$_{16}$, X$_{17}$, X$_{18}$, X$_{23}$, X$_{24}$, X$_{27}$ and X$_{32}$ represent any amino acids, said peptide being able to specifically inhibit the RhoA GEF activity of Trio and the RhoA GEF activity of the oncogenic form of Trio, i.e. Tgat, said peptide having inhibiting properties at least 2 fold, preferably 3 fold higher, more preferably 5 fold higher compared to the inhibiting activity of TRIPα (SEQ ID NO:197)

with the proviso that said amino acid sequence does not comprise or consist of the amino acid sequence SEQ ID NO: 1, said nucleic acid sequence being inserted in said vector.

The invention also relates to a host cell, in particular chosen from bacteria, viruses, yeasts, fungi, plants or mammalian cells, the said host cell being transformed, especially by means of a vector defined above, in such a way that its genome contains a nucleotide sequence defined above.

The invention also relates to a pharmaceutical composition comprising at least one of the following active ingredients, at least one of the following ones:

at least a peptide as defined above, preferably a peptide comprising or consisting of the amino acid sequence SEQ ID NO: 3,

wherein bold underlined amino acids represent essential amino acids for the activity of said peptide, and wherein $X_{13}, X_{16}, X_{17}, X_{18}, X_{23}, X_{24}, X_{27}$ and $X_{32}$ represent any amino acids, said peptide being able to specifically inhibit the RhoA GEF activity of Trio and the RhoA GEF activity of the oncogenic form of Trio, i.e. Tgat, said peptide having inhibiting properties at least 2 fold, preferably 3 fold, more preferably 5 fold higher compared to the inhibiting activity of TRIPα (SEQ ID NO:1), with the proviso that said amino acid sequence does not comprise or consist of the amino acid sequence SEQ ID NO: 1, at least a nucleic acid as defined above, preferably a nucleic acid coding for the above peptide, and at least a recombinant vector as defined above, preferably a recombinant vector comprising the above mentioned nucleic acid molecule coding for the above mentioned peptide, or their pharmaceutically acceptable salts thereof,
in association with a pharmaceutically acceptable vehicle.

Dosage of the active substance depends on the administration route, and can be easily determined by a skilled person. The pharmaceutical composition according to the invention can be administered by intravenous route, sub-cutaneous route, systemic route, or can be administered locally by infiltration, or per os.

The invention relates, in one advantageous embodiment, to the pharmaceutical composition as defined above, characterized in that it contains from about 1 μg to about 10 mg, preferably from about 700 μg to about 80 mg, more preferably from about 7 to about 40 mg, as a unit dose, of the above mentioned peptide and/or nucleic acid and/or recombinant vector.

The invention relates, in one advantageous embodiment, to the pharmaceutical composition previously defined, in association with at least a chemotherapy agent, said chemotherapy agent being in particular a. chosen from the group comprising or consisting of: doxorubicin, methotrexate, vinblastine, vincristine, cladribine, fluorouracil, cytarabine, anthracyclines, cisplatin, cyclophosphamide, fludarabine, gemcitabine, aromatase inhibitors, irinotecan, navelbine, oxaliplatin, taxol, and docetaxel, or b. chosen from the group comprising or consisting of: bevacizumab, pegaptanib, and ranibizumab, which are anti angiogenic agents.

In one another embodiment, the invention relates to the pharmaceutical composition previously defined, for a simultaneous, separated or sequential use for the treatment of cancer.

In the invention, "cancer" designates benign tumors or malignant tumors.

Malignant tumors are a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancer differentiate them from benign tumors, which are self-limited, and do not invade or metastasize.

Cancer according to the invention includes solid tumors, leukemia and lymphomas.

The invention also relates to the use of the recombinant vector as defined above, for the preparation of a drug intended for the treatment of cancer.

The invention also relates to the use of the isolated nucleic acid as defined above, for the preparation of a drug intended for the treatment of cancer.

The invention will be better understood with the following figures and examples, but in any case have to be limited to them.

BRIEF DESCRIPTION OF THE DRAWINGS

FIG. 2A represents a RhoA activation assay. Lysates of NIH3T3 cells stably expressing GFP, GFP-Tgat, or GFP-TgatL190E were subjected to GST-pulldown using recombinant RBD (RhoA binding domain of Rhotekin). The levels of GTP-bound RhoA (top panel) and total RhoA protein (middle panel) were assessed by Western Blot with a monoclonal anti-RhoA antibody. All GEF constructs were expressed at a similar level as shown by Western blotting using an anti-GFP antibody (lower panel).

FIG. 2B represents the quantification of the RhoA activation assay from at least three independent experiments. Y-axis represents Fold RhoA activation. "Fold RhoA activation" means the amount of RhoA-GTP in the sample, as compared to the amount in the GFP control, which was set to 1.

FIGS. 3A and 3B show the ex vivo transforming properties of Tgat.

FIG. 3A represents a focus formation assay of NIH3T3 cells stably expressing GFP, GFP-Tgat, GFP-TgatL190E or GFPTrio.

FIG. 3B represents Quantification of three independent focus formation assays. The Y-axis represents the foci formation expressed in %. The number of foci induced by Tgat was set to 100%. Error bars represent standard deviation.

FIG. 4 represents the inhibition of Tgat GEF activity by TRIPT16M/L17S (SEQ ID NO: 41) and TRIPE32G (SEQ ID NO: 40) in vitro. FRET fluorescence exchange assays were performed using constant concentrations of RhoA (1 μM), equal amounts (0.5 μM) of Tgat (left panel) or Trio DH2 (right panel), and increasing concentrations of GST-TRIP peptides, up to 100 μM. Results were expressed as kobs values plotted as a function of the indicated TRIP inhibitor concentration.

Figures represent the comparison of TRIPE32G and TRIPT16M/L17S inhibition efficiency on different GTPase/RhoGEF systems, using 1 μM GTPase and 0.5 μM GEF as follows:

FIG. 6A. RhoA/Tgat;
FIG. 6B. RhoA/p63RhoGEF;
FIG. 6C. RhoA/p115RhoGEF;
FIG. 6D. RhoA/Lbc;
FIG. 6E. RhoA/Dbl;
FIG. 6F. RhoG/Trio DH1PH1.

In each assay, the peptides were used at a concentration of 20 μM, corresponding to a 40 fold molar excess of inhibitor versus GEF. All fluorescence kinetics assays were performed using 1 μM mant-GTP. Results are expressed as Relative Fluorescence Units (RFU) versus time. The reaction performed in the absence of GEF reflects the spontaneous exchange activity of the GTPase.

Curves with squares (■) represents experiments with GEF+GST, curves with triangles (▲) represent experiments with GEF+GST-TRIPE32G, curves with reverse triangles (▼) represent experiments with GEF+GST-TRIPT16M/L17S, and curves with reverse lozenges (♦) represent experiments with no GEF+GST.

Figure 7A:
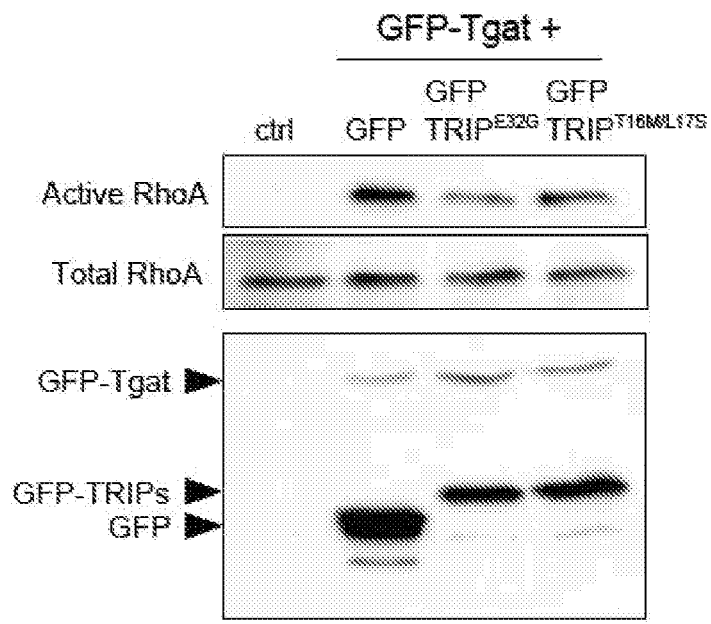
Figure 7B:
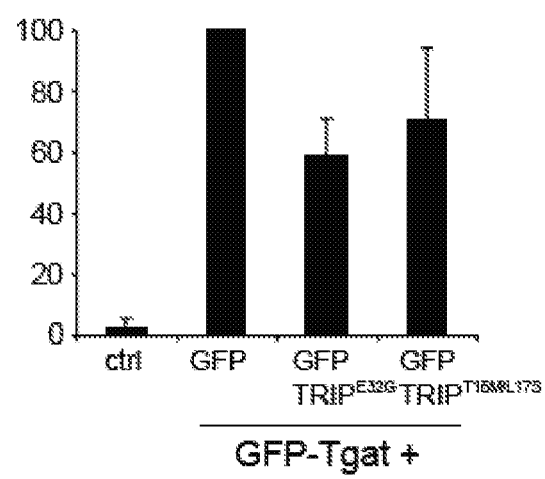

FIGS. 7A and 7B represent the Tgat GEF inhibition by TRIPE32G in cells.

Figure 2A:
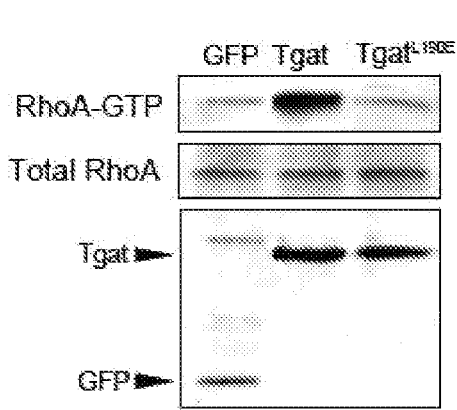
FIGS. 2A and 2B show that the transforming activity of Tgat requires its GEF activity towards RhoA.

The RhoA activation in NIH3T3-Tgat cells stably transfected with GFP, GFP-TRIPE32G or GFPTRIP T16M/L17S was assayed by the GST-RBD-pulldown assay as described in FIG. 2A.

FIG. 7A represents the levels of GTP-bound and total RhoA protein, shown in the upper two panels. Expression levels of all GFP-tagged proteins are shown in the lower panel.

FIG. 7B represents a quantification of the RhoA activity assay from at least three independent experiments. Error bars represent standard deviation.

FIG. 8 represents the effect of GFP-TRIPE32G on RhoA activation induced by Dbl (left panel) or Tgat (right panel) in NIH3T3 cells, assayed by GST-RBD pulldown. The levels of GTP-bound and total RhoA protein are shown in the upper two panels. Expression levels of Myc-Dbl and of all GFP-tagged proteins are shown in the lower two panels.

FIGS. 9A and 9B represent TRIPE32G mediated inhibition of the transforming activity of Tgat ex vivo.

FIG. 9A represents the focus formation assay of NIH3T3 cells, stably expressing GFP or GFP-Tgat, together with GST or GST-TRIPE32G.

FIG. 9B represents the quantification of three independent focus formation assays. The number of foci formed by Tgat/GST expressing cells was set to 100%.

Figure 10A:
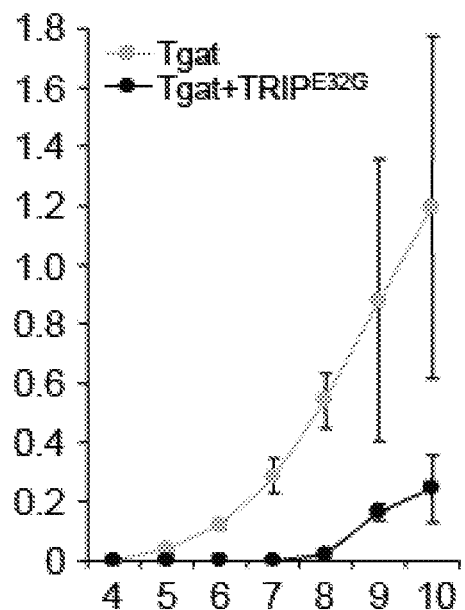
Figure 10B:
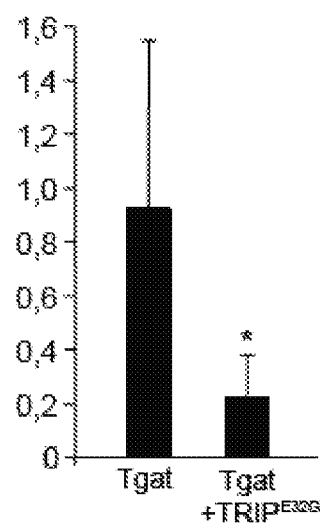

FIGS. 10A and 10B represent the TRIPE32G inhibition of the transforming activity of Tgat in vivo.

FIG. 10A represents tumor formation in Balb/c nude mice. NIH3T3 cells stably expressing GFP-Tgat/GST or GFP-Tgat/GSTTRIP E32G were injected subcutaneously into the flanks of Balb/c nude mice and tumor volume was measured every week. The graph is representative of the three independent assays that were performed.

FIG. 10B represents the tumor weights (in grams) after the experiments. Ten weeks post graft, mice were euthanised, tumors were excised and weighed, and the mean tumor weight was plotted on the graph. (*) A paired Student's t-test was performed, matching the samples for each mouse, and the P value was 0.019. Error bars represent standard deviation in all graphs.

EXAMPLES

Example 1

TRIPα Derived Peptides Target an Oncogenic RhoGEF

Rho GTPases and their GEFs represent challenging targets for inhibition, not only to understand their function but also in pathology, and strategies to inhibit their function are actively being sought (Bos et al., 2007). The main issue when trying to inhibit RhoGEFs is to achieve a high degree of specificity within such a complex and large family of related proteins, and to target protein-protein interactions which are not yet well characterized. To date only few strategies have been devised successfully, allowing the discovery of chemical and peptidic RhoGEF inhibitors, that block the activation of Rho GTPases by their cognate GEFs (Blangy et al., 2006; Gao et al., 2004; Schmidt et al., 2002). The inventors described previously peptide aptamer screening as such a strategy, which enabled them to discover the first RhoGEF inhibitor (Schmidt et al., 2002). Peptide aptamers are short peptides constrained by a bacterial Thioredoxin (TrxA) scaffold, which bind to their protein targets with high affinity (Baines and Colas, 2006; Hoppe-Seyler et al., 2004). This technology has been applied initially to the discovery of inhibitors against various intracellular targets, involved mainly in cell-cycle control or cell survival (Butz et al., 2000; Colas et al., 1996; Crnkovic-Mertens et al., 2003; Fabbrizio et al., 1999; Martel et al., 2006; Nouvion et al., 2007). Peptide aptamers present interesting advantages over other classes of inhibitory molecules, mainly because of their simple design and their high degree of binding specificity, which enables them to discriminate between closely related proteins within a functional family. But most remarkably, these highly combinatorial proteins are screened and designed to function inside living cells and allow the study of protein function within complex regulatory networks (Bickle et al., 2006). The RhoGEF inhibitor the inventors have isolated using this aptamer screening strategy, called TRIPα (Trio Inhibitory Peptide α), targets specifically the DH2-PH2 tandem of the RhoGEF Trio and inhibits its activation of RhoA both in vitro and in intact cells, reverting the neurite retraction phenotype induced by Trio DH2-PH2 in PC12 cells (Schmidt et al., 2002). Most interestingly, although TRIPα was initially selected with the TrxA scaffold, it remained equally active as a linear peptide (Schmidt et al., 2002). The recently identified oncogenic RhoGEF Tgat is an interesting novel candidate target for such peptidic inhibitors. Indeed, Tgat has been identified from Adult T-Cell Leukemia (ATL) patient cells as a gene with oncogenic potency and originates from an alternate splicing of the trio gene (hence the name Tgat, for Trio-related transforming Gene in ATL Tumor cells) (Yoshizuka et al., 2004). Tgat retains only the RhoA-specific DH2 domain of Trio and, instead of the associated PH2 domain, carries a unique C-terminal sequence of 15 amino acids. It induces cell transformation and tumor formation in nude mice (Yoshizuka et al., 2004) and has been proposed to enhance tumor invasion by stimulating Matrix MetalloProteinases (MMPs) via the RECK protein (Mori et al., 2007) and by activating the transcription factor NF-κB, which plays a crucial role in tumorigenesis, including ATL (Yamada et al., 2007).

In this context, designing peptide inhibitors against the RhoGEF Tgat is very challenging from a pathological point of view. In this study the inventors devised a screen to identify optimized peptides based on the TRIPα peptide. This screen allowed them to identify a novel peptide that is active as a Tgat inhibitor, targeting its GEF activity in vitro in a highly specific manner. Moreover, it strongly reduces its oncogenic properties in vivo, most remarkably by decreasing foci formation and tumor development in nude mice. The peptide optimization strategy identifies the first inhibitor of the Tgat oncogene, and demonstrates that aptamers can be used to interfere with RhoGEF functions in vivo with exquisite specificity.

Results

The GEF Activity of the DH Domain is Required for Tgat-Induced Transformation.

Figure 1:
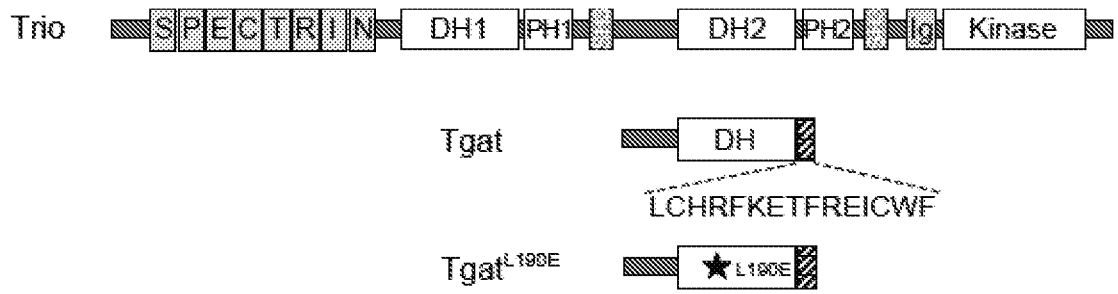
FIG. 1 shows a schematic representation of Trio and its splice variant Tgat, and the Tgat mutants
Figure 2B:
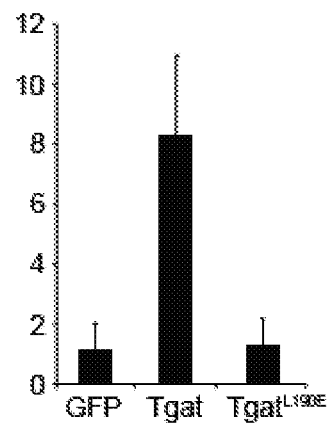

In order to design inhibitors that would target Tgat oncogenic activity, the inventors first established whether the GEF activity of Tgat is involved in transformation. To do so, the inventors designed a Tgat mutant, called TgatL190E, which harbors a point mutation in its DH domain, the equivalent mutation in Trio DH2-PH2 being known to abolish its exchange activity on RhoA (FIG. 1) (Bellanger et al., 2003). The inventors established NIH3T3 cell lines stably expressing similar levels of GFP or GFP-tagged Tgat or TgatL190E (FIG. 2A, lower panel), and analyzed the ability of these constructs to activate RhoA and to induce transformation. The inventors measured RhoA activation in intact cells by pull-down of RhoA-GTP, using the RhoA-binding domain (RBD) of its effector Rhotekin fused to GST (FIG. 2A-B). Tgat strongly stimulated RhoA activation (8-fold over control), while the GEF-impairing mutation completely abolished the formation RhoA-GTP in cells. The inventors then tested the oncogenic properties of the different Tgat constructs, by scoring the formation of foci in the different cell lines (FIG. 3A-B). While Tgat-expressing cells formed numerous foci, TgatL190E-expressing cells presented no foci after 3 weeks in culture, showing that the GEF activity of the DH domain is required for the transforming potential of Tgat. In addition, NIH3T3 cells stably expressing full length Trio did not exhibit any foci, showing that the transforming potential is not inherent to Trio but only to its oncogenic isoform Tgat (FIG. 3A-B).

Strategy to Identify a Tgat Inhibitor.

Since the GEF activity of Tgat is necessary for transformation, molecules that block this biochemical activity could also inhibit its transforming potential. The inventors previously identified a peptide aptamer, TRIPα, which targets the RhoA-specific DH2-PH2 tandem of Trio (Schmidt et al., 2002). As Tgat harbors the DH2 domain of Trio, the inventors tested whether Tgat activity was also inhibited by TRIPα. However, and very surprisingly, when tested in a [3H]-GDP dissociation inhibition assay in vitro, TRIPα was only a weak inhibitor of Tgat (Kiapp=89±33 μM; see below).

The inventors thus sought to optimize TRIPα inhibition efficiency, by first determining which amino acids are essential for its inhibition, using an Ala-Scan analysis.

Each residue of the active core of TRIPα (amino acids 9-36; Schmidt et al., 2002) was mutated to alanine, except cysteines which were changed into serines. All TRIPα mutants were then tested for their inhibitory activity on Trio DH2-PH2 in [3H]-GDP dissociation assays. This analysis mapped two essential regions of TRIPα, amino acids 9-20 and 28-33, where single mutations were sufficient to impair inhibition (see table 3).

TABLE 3

Alanine-scanning of the active core of TRIPα.

(SEQ ID NO: 197)
Active core analysed
by ALA-Scan

```
         9                                  36
  1        10        20        30        40
AREGADGA CGYNLA LVM G SERVFCPLC CSSDIYELM
  1        9       20      28    33
```

Inhibition efficiency of the mutated peptides was measured by [3H]-GDP dissociation assays using Trio DH2-PH2, and compared to the original TRIPα peptide.
Black bold letters (C, G, Y, A, M, C, P, L, and C) correspond to residues strictly required for inhibition;
Grey bold underlined letters ( ) correspond to residues retaining a weak inhibitory potential.
All the other residues are non essential.
Shaded residues (grey boxes ) correspond to regions (aa 9-20 and 28-33) that emerge as being essential for TRIPα activity.

However, none of the mutants exhibited stronger inhibition towards Trio DH2-PH2 and were not further investigated on Tgat.

The inventors next reasoned that peptides that would bind stronger to the GEF domain may also be better at inhibiting its activity. The inventors thus generated a library of peptide aptamers derived from TRIPα by random mutagenesis, which the inventors screened for GEF binding in a yeast two-hybrid assay. The inventors chose a system in which the threshold of interaction detection can be modulated by the concentration of the 3-aminotriazole (3-AT) drug (Sardet et al., 1995). Since Tgat is toxic in yeast, the inventors used Trio DH2-PH2 to screen this TRIP-like peptide library. Thirty-five independent clones bound to Trio DH2-PH2 at concentrations of 3-AT at which no interaction with TRIPα was detected anymore (80-120 mM). These clones were then produced as GST fusions and analyzed for their inhibition of Trio DH2-PH2, using the [3H]-GDP dissociation assay.

Table 4 represents the 11 peptides being stronger inhibitors than TRIPα. In particular, the peptides according to the invention have an increase of activity from about 3 fold to about 6 fold compared to TRIPα. Inhibition efficiency was measured on Trio DH2-PH2 and compared to TRIPα, as described in Table 3.

Analysis of their sequence revealed that they contained one to four mutations per peptide, and that, consistently, most of them resided within the two regions identified as crucial for the inhibitory properties of TRIPα.

TABLE 4 represents the amino acid sequence of the optimized TRIP-like peptides according to the invention, obtained by random mutagenesis of the original TRIPα peptide.

| Name | SEQ ID NO: | SEQUENCE |
|---|---|---|
| TRIPα | 197 | AREGADGA CGYNLA LVM G SERVFCPLC CSSDIYELM<br>\|    \|    \|    \|    \|    \|    \|    \|    \|<br>1    5   10   15   20   25   30   35   40 |

TABLE 4-continued represents the amino acid sequence of the optimized TRIP-like peptides according to the invention, obtained by random mutagenesis of the original TRIPα peptide.

| Name | SEQ ID NO: | SEQUENCE |
|---|---|---|
| E³²G | 40 | ----------------------G--------- |
| T¹⁶M/L¹⁷S | 41 | ----------MS------------------- |
| T¹⁶M | 42 | -----------M-------------------- |
| T¹⁶M/S³²G | 44 | -----------M-----G-------------- |
| A¹T/V¹⁸D/F²⁷L | 45 | T-----------D-------L---------- |
| E³²G/S³⁶T | 46 | ----------------------G---T------ |
| T¹⁶A/V¹⁸G/E³²G/I³⁸N | 47 | -----------A-G-----------G-----N---- |
| V¹⁸A/E²⁴A/E³²G | 48 | -----------A-----A----G--------- |
| N¹³D/T¹⁶M/C³⁴R | 49 | --------D--M------------R-------- |
| T¹⁶A/L¹⁷S/C³⁴R/S³⁶P | 50 | -----------AS-----------R-P------ |
| V¹⁸D/I³⁸S | 51 | -----------D----------------S---- |

Figure 5:
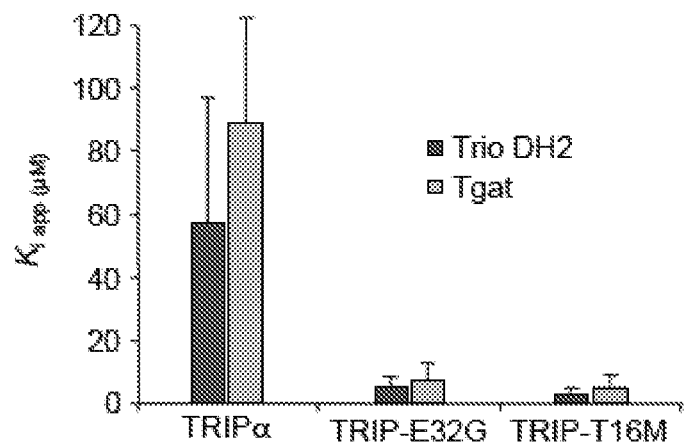
FIG. 5 represents a histogram showing the apparent inhibition constants (Ki app) of the TRIP peptides for Tgat and Trio DH2, as indicated. The values and error bars are calculated from at least three independent experiments. Error bars represent standard deviation

The inventors then analyzed the inhibitory activity towards Tgat of TRIPE32G and TRIPT16M/L17S, the two TRIP-like peptides that displayed the highest inhibition on Trio DH2-PH2 (Table 4). Both peptides inhibited Tgat GEF activity in a dose-dependent manner in a kinetics fluorescence assay, while GST alone (not shown) or GST-TRIPα, at the same concentrations, had no effect (FIG. 4). Accordingly, the apparent inhibition constant (Kiapp) of TRIPα towards Tgat was 89±33 μM, and decreased to 7.4±5 μM for TRIPE32G and 5.1±4 μM for TRIPT16M/L17S (FIG. 5). These data show that TRIPE32G and TRIPT16M/L17S are both about 15 times more efficient than TRIPα at inhibiting the exchange activity of Tgat. Interestingly, the optimized peptides were equally efficient on Tgat and on Trio DH2, as shown by their similar Kiapp values (FIGS. 4 and 5). This suggests that the unique Cterminal extension of Tgat is not involved in the inhibitory mechanism of the optimized peptides, and is consistent with the fact that this sequence does not interfere with the GEF activity in vitro (data not shown).

Similar results were obtained with the mutant TRIPT16M.

Inhibition by TRIP Peptides is Specific for Tgat.

Figure 6:
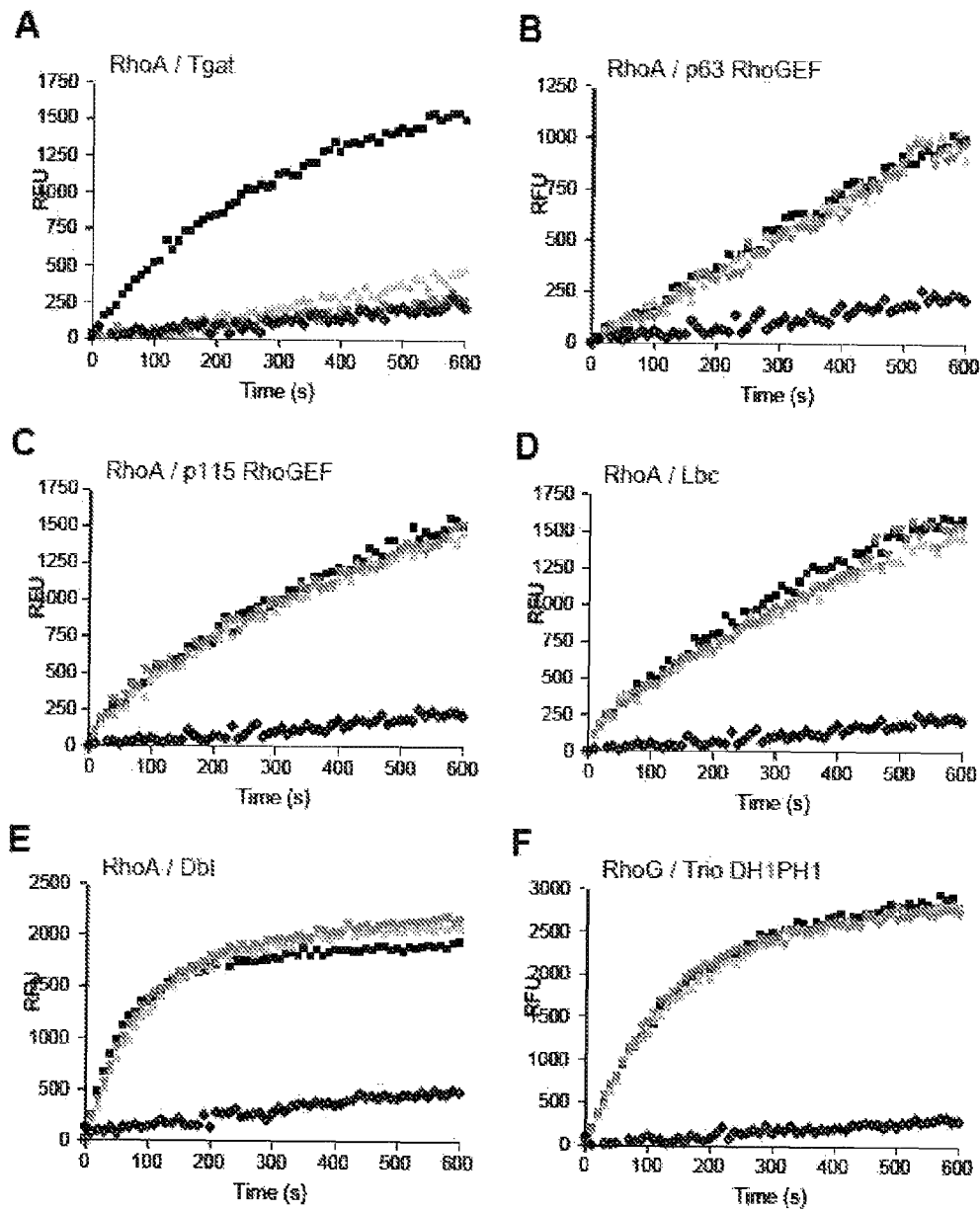
FIGS. 6A-6F represent the specificity of the optimized inhibitory peptides according to the invention TRIPT16M/L17S (SEQ ID NO: 41) and TRIPE32G (SEQ ID NO: 40).

The inventors then analyzed the specificity of the optimized TRIP peptides, by testing their inhibitory properties on other related RhoGEFs. The inventors had shown previously that TRIPα is not active on the RhoA-specific GEFs p115RhoGEF, Lbc, p63RhoGEF, nor on Dbl (Schmidt et al., 2002 and unpublished results). Similarly, when tested in mant-GTP fluorescence kinetics at a concentration at which Tgat is fully inhibited, TRIPE32G and TRIPT16M/L17S had no effect on the exchange activities of these closely related RhoGEF/Rho-GTPase tandems, p115RhoGEF/RhoA, Lbc/RhoA, Dbl/RhoA, and even the very closely Trio-related p63RhoGEF/RhoA (70% identity within the DH-PH module), or Trio DH1-PH1/RhoG (40% identity with Tgat) (FIG. 6). Taken together, these data show that the optimized TRIP peptides are highly specific for Tgat and Trio DH2.

TRIPE32G Inhibits the Transforming Activity of Tgat In Vivo.

The inventors next analyzed whether their TRIP-like peptides inhibited Tgat-mediated RhoA activation in intact cells. For that purpose, NIH3T3 cells stably expressing Tgat were transfected with the GFP-tagged TRIP-like peptides or GFP alone, and RhoA activation levels were assessed by the GST-RBD pull-down assay. Although TRIPE32G and TRIPT16M/L17S inhibited the in vitro GEF activity of Tgat to a similar extent, TRIPE32G was more efficient than TRIPT16M/L17S at inhibiting Tgat-mediated activation of RhoA in cells (FIG. 7A-B). These data show that, in addition to its effect on in vitro guanine nucleotide exchange, TRIPE32G inhibits Tgat GEF activity also in intact cells. In order to verify the exquisite specificity of the peptide towards Tgat/DH2 in vivo, the inventors analyzed by GST-RBD pull-down assay whether TRIPE32G could inhibit oncogenic Dbl mediated RhoA activation in intact cells. FIG. 8 shows that, in contrast to its effect on Tgat activity, TRIPE32G was not able to inhibit RhoA activation by Dbl, confirming the in vitro specificity of TRIPE32G towards Tgat. The inventors then investigated whether TRIPE32G was able to inhibit Tgat-induced transformation. To do so, the inventors stably expressed GST or GST-TRIPE32G in Tgat-expressing NIH3T3 cells and characterized their transforming potential. After 3 weeks of culture, the foci present in Tgat expressing cells were severely reduced when co-expressing TRIPE32G (FIG. 9A-B). This reduction is not due to a non-specific effect of TRIPE32G on cell proliferation or apoptosis (data not shown). These data show therefore that targeting Tgat GEF activity with TRIPE32G is sufficient to impair Tgat transforming activity. To further establish the inhibitory effect of TRIPE32G on Tgat transforming activity in vivo, the inventors subcutaneously inoculated Balb/c nude mice with NIH3T3 cells expressing either Tgat, or Tgat and TRIPE32G, and analyzed their effect on tumor formation. Tgat-transformed cells produced tumors in ten out of twelve mice. Remarkably, when TRIPE32G was co-expressed with Tgat, only seven mice had tumors and the inventors observed a delay of about three weeks in the formation of tumors (FIG. 10A). In addition, even though tumor formation was not abolished, the weight of the tumors was significantly reduced when TRIPE32G was expressed (FIG. 10B). Altogether, these data show that expression of TRIPE32G strongly reduces Tgat transformation activity in cells and affects tumor formation in nude mice, most likely by inhibiting Tgat-mediated GTP loading of RhoA.

Interpretation

Peptide Aptamers as New Inhibitors of RhoGEFs.

Because of their deregulation in many human disorders including cancer, Rho GTPases and their activating GEFs represent challenging targets for inhibition. In humans there are only 20 Rho GTPases but more than 70 RhoGEFs, and it appears that signaling specificity is mostly determined by the GEFs, which activate the GTPases at defined timing and location. RhoGEF inhibitors therefore represent an emerging field of investigation. Here the inventors developed a peptide aptamer screening strategy to inhibit the RhoGEF Tgat, a potential target in the ATL disease. Since Tgat is an isoform of the RhoGEF Trio, which includes the RhoA-specific DH2 domain plus a unique C-terminal sequence, the inventors based their screen on their previously identified Trio inhibitor TRIPα, the first peptidic RhoGEF inhibitor described, which targets the DH2-PH2 domain of Trio (Schmidt et al., 2002). Intriguingly, despite the fact that Tgat harbors the Trio DH2 domain, their original TRIPα inhibitor was rather ineffective at inhibiting Tgat. This suggests that the PH2 domain of Trio is involved in the mechanism of action of TRIPα, and that its replacement by the C-terminal extension decreases TRIPα's ability to inhibit the GEF activity of Tgat.

The inventors show here that GEF inhibitors selected with the peptide aptamer screening approach are readily amenable to structure-activity relationship analysis and optimization. Of the 28 residues located in the active core of TRIPα, alanine scanning mapped 9 residues in two regions (residues 9-20 and 28-33) that were critical for the catalytic activity, while 6 had a moderate effect and the others had no effect. The inventors also show that peptide aptamer optimization can be achieved by random mutagenesis combined with a selection screen based on interaction strength. At least one third of the isolated clones yielded stronger inhibition, thus validating the rationale of the screen. The two selected peptides, TRIPE32G and TRIPT16M/L17S, were 15-fold more efficient than TRIPα and inhibited Tgat GEF activity at concentrations lying in the low micromolar range. Interestingly, mutations found in these clones also fell within the two important regions identified by the Ala-scan. Furthermore, this approach allowed us to turn TRIPα into a Tgat inhibitor, which could be achieved with as few as one mutation, E32G. It remains to be determined whether these different amino acids are important for binding to the GEF and/or for inhibition of the exchange reaction. It should be emphasized that the screening and optimization method of the inventors is effective, irrespective of the inhibitory mechanism, which is of big advantage for the discovery of inhibitors of protein-protein interactions. The way the original screen was performed, i.e. two-hybrid screening with the GEF as bait in the absence of GTPase, strongly suggests that the target of the peptides is the GEF itself, rather than the GTPase. This is reinforced by the fact that the peptides do not inhibit spontaneous GDP release from RhoA using [3H]-GDP-loaded RhoA (data not shown), and by their specificity data in vitro and in intact cells, which show that other GEF activities towards RhoA are not inhibited (FIGS. 6 to 8).

Peptide Aptamers are Functional In Vivo

The screening method of the inventors demonstrates that TRIPE32G is not only effective and specific at inhibiting Tgat GEF activity in vitro, but that it also blocks Tgat-induced cell transformation and tumor formation in vivo. This is the first example of a peptidic RhoGEF inhibitor that is functional in vivo, and demonstrates that aptamers can be used as active peptides to perturb the function of GEFs in vivo. In this context, efficient in vivo delivery is a critical issue when working with peptides. To circumvent this problem, the use of recently developed cell penetrating peptides represents a good means of delivery for TRIPE32G, and could be an attractive strategy to investigate the contribution of Tgat in leukemogenesis. Indeed, to date, the incidence of Tgat in ATL leukemogenesis is unknown, but given the strong effect of Tgat on RhoA activation and transformation, the inventors can hypothesize that Tgat is involved in the progression of ATL by contributing to RhoA-mediated proliferation and/or metastasis. The inventor's series of TRIP peptides should now prove useful tools to decipher the cellular role of Tgat.

Peptide Aptamers Versus Other GEF Inhibitor Screening Strategies.

Besides the peptide aptamer screening approach of the inventors, other strategies have recently been devised to discover chemical inhibitors of Rho GTPase/GEF tandems, and also other classes of small G proteins, such as the Arf family and their activating GEFs (Blangy et al., 2006; Desire et al., 2005; Gao et al., 2004; Mayer et al., 2001; Shutes et al., 2007; Viaud et al., 2007). Computer-assisted virtual screening, for example, identified the NSC23766 compound, based on structure-function information of the Rac1/Tiam1 complex. This powerful molecule inhibits specifically Rac1-induced events in vitro and in vivo, however the targeted associated RhoGEFs include at least Tiam1 and Trio DH1-PH1 (Gao et al., 2004). In silico screening also yielded the LM11 compound, which inhibits specifically the ARNO/Arf1 interface in vitro and is active in cells (Viaud et al., 2007). Given their membrane permeability, both NSC23766 and LM11 have the advantage of being easily applied in vivo. The Yeast Exchange Assay is another screening method that allowed the identification of the TrioDH1-PH1 specific NPPD compound and its analogues (Blangy et al., 2006). Like peptide aptamer screening, this strategy has the advantage over virtual screening of identifying inhibitors directly in cells, and without any bias as to the targeted interaction site. Finally, in vitro RNA-aptamer screening selected the RNA aptamer M69 as an inhibitor of the Cytohesin/Arf1 tandem (Mayer et al., 2001). Like peptide-aptamers, these RNA aptamers are highly combinatorial and easily screened, but their application as potential drugs remains limited, due to difficult in vivo delivery. To circumvent this problem, RNA-aptamer displacement represents an elegant method, in which a small-molecule library is screened for compounds that displace the RNA-aptamer from its target and reproduce its inhibitory activity (Hafner et al., 2006).

The inventors' study shows that peptide aptamer screening represents a valid strategy for inhibitor identification that can be applied to a variety of different proteins, because of the in vivo screening method and the highly combinatorial libraries available, yielding strong affinity inhibitors. This is illustrated here by the identification of a highly specific peptidic RhoGEF inhibitor targeting the Tgat oncogene in vitro and in vivo.

Experimental Procedures

DNA Constructs—

Tgat (aa 1-255) was designed by ligating dimerized oligonucleotides coding for the specific C-terminus of Tgat (15 aa)

to the Trio DH2 domain (residues 1862-2101, corresponding to aa 1-240). The oligonucleotide sequences are available upon request. The TgatL190E mutant was obtained using the Quick Change Site Directed Mutagenesis Kit (Stratagene Inc.), according to the manufacturer's instructions. To create stable NIH3T3 cell lines, GFP-tagged Tgat, TgatL190E and full length Trio were cloned into the puromycin-resistant retroviral vector pBabePuro. GST-tagged TRIP peptides were cloned into the G418-resistant retroviral vector pLXSN. For transient transfections, both Tgat and TRIP peptides were cloned into the pEGFP vector (Clontech Inc.). Myc-Dbl was a kind gift of Michael Olson (Beatson Institute for Cancer Research, Glasgow). For in vitro GEF assays, Tgat (aa 1-255) was fused to maltose-binding protein (MBP) by cloning into a modified pMAL C2X vector (New England Biolabs Inc.). The TRIP peptides were fused to GST by cloning into the pGEX-5X2 vector (GE Healthcare Inc.). All constructs were checked by sequencing.

Expression and Purification of Recombinant Proteins—Tgat.

MBP-Tgat and MBP-DH2 expression in *E. coli* was induced for 24 h at 16° C. with 0.1 mM isopropylthiogalac-topyranoside (IPTG). After cell lysis (in 50 mM Tris pH 7.5, 1 mM EDTA, 2 mM MgCl2, 1 mM DTT), the suspension was centrifuged at 10,000 g for 20 min, then at 400,000 g for 1 h30. The supernatant was applied to a Q-Sepharose column fast flow (GE Healthcare) equilibrated with lysis buffer. The protein was eluted with a linear gradient of 0-250 mM NaCl in 50 mM Tris pH 7.5. Fractions containing the protein were adjusted to a concentration of 2 M NaCl and loaded on a Phenyl sepharose Fast flow High Sub (GE Healthcare Inc.). The protein was eluted with a linear gradient of 2-0 M NaCl in 50 mM Tris pH 7.5. The purified proteins were concentrated on a Vivaspin concentrator (Vivascience AG Inc.) at 18 mg/mL. Other proteins. Recombinant GST-Trio DH2-PH2, GST-Trio DH1-PH1, GST-Dbl (DH-PH domain), GST-Lbc (DH-PH), GST-p63RhoGEF (DH domain) and GST-RhoG were purified as described previously (Schmidt et al., 2002; Souchet et al., 2002). Expression and purification of GST-p115RhoGEF using the baculo virus system will be described elsewhere. GST-Peptides. GST-TRIP peptides were purified as described (Schmidt et al., 2002), except that the cell lysate was centrifuged as above, before loading on a GSTrap Fast Flow column (GE Healthcare Inc.) equilibrated with lysis buffer. Peptides were eluted with reduced glutathione (10 mM) in Tris 50 mM pH 7.5 and concentrated on Vivaspin concentrator at about 5-10 mg/mL.

Optimization of TRIPα—Alanine-Scanning of TRIPα.

Every amino acid of the active core of TRIPα (amino acids 9-36) was mutated to alanine (or serine for cysteine residues) by site directed mutagenesis of GST-TRIPα. Each TRIPα mutant was tested for its inhibitory activity on DH2-PH2 in [3H]-GDP dissociation assays.

Two-Hybrid Screening of TRIPα-Like Peptides.

An aptamer library derived from TRIPα was created by PCR-based random mutagenesis of TRIPα inserted into the yeast two-hybrid vector pPC86. Sequencing of a statistically representative number of clones yielded a mutation rate of ~3 mutations/clone. 6×10⁵ independent clones were screened for interactors, using Trio DH2-PH2 (in the pPC97 vector) as a bait, in the MAV 103 yeast strain, on high concentrations of 3-AT (3-amino-triazol, Sigma) (80-120 mM). Selected peptides were then produced as GST-fusions and analyzed for their inhibition of Trio DH2-PH2 using the [3H]-GDP dissociation assay.

Nucleotide Exchange Kinetics Assay—

Specific exchange rates of Tgat were measured with a fluorescence-based kinetics assay, using a 6His-RhoA construct (gift of Dr Derewenda, Charlottesville University, Virginia) purified as described (Oleksy et al., 2004). Exchange activities were followed by fluorescence resonance energy transfer (FRET) between the GTPase tryptophanes (λex=292 nm) and the methylanthranyloil group of mant-GTP (λem=440 nm) as described (Zeeh et al., 2006). All fluorescence measurements were performed with a CARY Eclipse fluorimeter (Varian). For each kobs determination, RhoA (1 µM) and Tgat (or Trio DH2) were preincubated 3 min at 25° C. in 700 µL reaction buffer (50 mM Tris pH 7.5, 50 mM NaCl, 2 mM MgCl2, 1 mM DTT). The exchange reaction was initiated by 10 µM mant-GTP and measured for 10 min until the plateau was reached. kobs were calculated by fitting the FRET fluorescence changes to a single exponential, using the Kaleidagraph software. Specific exchange activities were calculated by linear regression of kobs values determined for a range of GEF concentrations (0, 0.2, 0.3, 0.4, 0.5 and 1 µM).

Nucleotide Exchange Inhibition Assays—

Radioactive [3H]-GDP dissociation assays were performed as described (Schmidt et al., 2002). Briefly, 0.15 µM GST-Trio DH2-PH2 was preincubated for 15 min with 3 µM of GST-TRIP inhibitors. The reaction was started by addition of 0.4 µM [3H]-GDP-loaded RhoA and 1 mM GTP, and the reaction mix was filtered after 0 min and 15 min incubation at 25° C. Inhibition efficiency is expressed as the ratio between [3H]-GDP-bound RhoA at 15 and 0 min. Apparent inhibition constants (Kiapp) of TRIP-like peptides were determined from kobs values obtained at increasing peptide concentrations using the above fluorescence nucleotide exchange assay. Kiapp was calculated from the hyperbolic fit of kobs values as a function of the inhibitor concentration as described (Zeeh et al., 2006). TRIP-like peptide specificity was assayed using mant-GTP fluorescence kinetics (λex=360 nm, λem=460 nm) in a FLX800 Microplate Fluorescence Reader (BioTek Instruments). 0.5 µM Tgat, p63RhoGEF, Lbc, and p115RhoGEF, or 0.1 µM Dbl and Trio DH1-PH1 were preincubated 5 min at 25° C. in the presence of 20 µM GST, GST-TRIPE32G or TRIPT16M/L17S and 1 µM mant-GTP. The exchange reaction was initiated by addition of 1 µM RhoA or RhoG and monitored for 10 min.

Cell Lines, Transfection and Focus Formation Assay—

NIH3T3 cells were maintained as described previously (Sirvent et al., 2007). Transient transfection experiments were performed using the Jet PEI reagent, according to the manufacturer's protocol (QBiogene Inc.). NIH3T3 cell lines stably expressing GFP-Tgat, GFP-TgatL190E, or GFP-Trio, with or without the GST-TRIP peptides, were generated as follows: the indicated retroviral constructs were transfected into BOSC packaging cells, using the Lipofectamine reagent (Invitrogen Inc.). Forty-eight hours after transfection, virus containing supernatants were collected and used to infect NIH3T3 cells. Infected cells were selected with 6 µg/mL puromycin and/or 1 mg/mL G418 and stable transfectants were pooled after selection. Tgat or TRIP mRNA levels in the different cell lines were monitored by RTPCR, and protein expression levels by Western blot analysis using a polyclonal anti-GFP antibody (Toney Pines Laboratories). Focus formation assays were performed using stable NIH3T3 cell lines as indicated, seeded at 5×10⁴ cells in 6-well plates and maintained for 15 to 21 days in 10% FBS. Medium was renewed every two days. After staining with Crystal Violet (1%), plates were photographed and foci were scored using the Metamorph software. All experiments were done in triplicate.

RhoA Activation Assay in Cells—

The level of GTP-bound RhoA was measured by a GST pulldown assay as described (Schmidt et al., 2002). Briefly, cell lysates were incubated with glutathione beads coated with the recombinant Rho-binding domain (RBD) of the RhoA specific effector Rhotekin (Cytoskeleton Inc.). Total or GTP-bound RhoA in the samples was revealed by Western blot analysis, using a monoclonal anti-RhoA antibody (Santa-Cruz Biotechnology Inc.).

Mice and Xenografting—

Female Balb/c nu/nu mice were purchased from Charles River France and used at 6-8 weeks of age. 12 Balb/c nu/nu mice were subcutaneously grafted with 2×106 cells of each cell line on both sides (Tgat on the left and Tgat+TRIPE32G on the right flank of the leg). The appearance of tumors was scored visually every week. 10 weeks post graft, mice were euthanized and tumors excised and weighed. mRNA and protein levels in the tumors were verified by RT-PCR and Western blot (data not shown).

Example 2

Targeting Trio Amplification in Human Cancer

The Trio gene has been found amplified in a variety of human cancers, including glioblastoma, breast cancer, soft tissue sarcoma, urinary bladder cancer, cervical carcinoma, oral squamous cell carcinoma and lung cancer (Adamowicz et al., 2006; Baldwin et al., 2005; Calaf and Roy, 2007a, b; Coe et al., 2005; Garnis et al., 2005; Kloth et al., 2007; Lane et al., 2008; Mhawech-Fauceglia et al., 2006; Ng et al., 2007; Salhia et al., 2008; Zheng et al., 2004). CGH array studies, aimed at characterizing the genetics of these various cancer types, revealed amplification of chromosome 5p and of the trio gene in particular, which, in many cases, was correlated to an increase in its transcript. In addition, in urinary bladder cancer for example, Trio amplification was strongly associated with invasive tumor phenotype, high tumor grade and rapid tumor cell proliferation. In other cases, like glioblastoma or breast cancer, Trio overexpression was associated with poor prognosis and poor patient survival. This suggests a potential implication of Trio in the aggressive phenotype of these cancers, most probably by activating Rho GTPase signaling. In addition, an oncogenic Trio isoform, Tgat (harboring only the RhoA-activating GEF2 domain of Trio), has been identified in patients with Acute T-cell leukemia (ATL).

Trio thus appears as an attractive target for drug design and the TRIP peptides according to the invention, which manipulate its cellular activity with high specificity, are therefore of enormous therapeutic potential.

In this context, the inventors have analyzed the contribution of Trio and/or its oncogenic isoform Tgat in the proliferative/motile/invasive properties of tumor-derived cell lines, and have evaluated the inhibitory potential of the TRIP peptides to inhibit these phenotypes.

A. Using available tumor-derived cell lines originating from various cancer types where Trio is overexpressed, the inventors have first analysed if high levels of Trio protein correlate with an over-activation of its target GTPases, Rac1 and RhoA. To do so, the inventors have performed Rho-activation pulldown assays as described earlier (Bouquier et al., 2009), on the following cell lines (but not limited to):

Bladder tumor cell lines that show Trio amplification: 5-HTB, RT11-D21, RT112 and CRL-7930, compared to other bladder cell lines without Trio amplification (3-HTB, 4-HTB), Cervical squamous cell carcinoma with Trio upregulation: CasKi, SiHa, HeLa, compared to cell lines without Trio amplification (CSCCI, CSCC7, CCB, CC10A, CC10B, CCII− and CCII+), Small cell lung carcinoma SCLC cell lines: NCI-H187, NCI-H378, NCI-H889, NCI-H1184, NCI-H1607, NCI-H1672, NCI-H1963, NCI-H2141, NCI-H2171, NCI-H2195, NCI-H2227, HCC33, NCI-H82, NCI-H289 and NCI-H526.

Breast cancer cell lines: MCF7, MDA-435 and SKBR3.

B. In those cell lines where RhoA activation is enhanced, the inventors have assessed proliferation, motility and invasive properties, compared to cell lines with basal level RhoA activation. Theses experiments have been done by cell growth and focus formation assays, anchorage-independent growth assays and wound-healing assays, as well as cell invasion assays in Boyden Chambers (see Example 5).

C. In the cell lines which show Trio amplification, RhoA activation and one or more of the phenotypes analyzed in (B), the inventors have targeted Trio directly, using the TRIP$^{E32G}$ peptide. Cell lines have been transfected with a GFP-tagged-TRIP$^{E32G}$ plasmid or infected using retroviral vectors (see (Bouquier et al., 2009). The inventors have evaluated the effect of Trio inhibition on RhoA activation, proliferation, motility and invasiveness using the assays mentioned above. When successful, in vivo assays have been achieved, using mouse models for the various cancer types. For example, to assess invasion, the inventors have used a lung colonization mouse model, where breast cancer cell lines (Forozan et al., 2000), stably expressing TRIP$^{E32G}$ (or a control plasmid), have been injected into the mouse tail and the number/size of lung metastases have been measured three weeks later (see example 5).

Example 3

Targeting Trio Mutations in Human Cancer

A large number (210) of diverse human cancers (including breast, lung, colorectal, gastric, testis, ovarian, renal, melanoma, glioma, ALL cancers) have been screened by systematic sequencing for the presence of mutations in the 518 kinases of the entire genome (Greenman et al., 2007). Thus, 7 recurrent mutations have been found in the Trio gene, among which are 5 point mutations (1 in GEF1, 1 in GEF2, 2 in the kinase, 1 just after ATG), 1 insertion and 1 deletion mutant: TrioG53E, Trio A97(InsP), Trio T1258M, TrioV1920M, TrioG2795D, TrioR2817C, TrioA2983V.

In order to further investigate the potential relevance of these Trio mutations in tumorigenesis, the inventors have introduced each one of these mutations (by site directed mutagenesis) in the Trio gene and have created stable NIH3T3 cell lines expressing these mutants. The inventors have measured the proliferative, migratory and invasive properties of the cell lines (see above and Materials and Methods). The inventors are particularly focusing on the V1920M mutation, which lies in the GEF2 domain of Trio.

The inventors have infected the NIH3T3 cell lines stably expressing the Trio mutants with a retroviral vector expressing the TRIP$^{E32G}$ peptide, and have analyzed its inhibitory effect, using the above assays as readouts.

In parallel the inventors have tested if Trio GEF activity was modified due to the mutations, especially in the GEF2 domain mutant (V1920M), which could lead to deregulated RhoA activity. To do so, the inventors have inserted the mutation V1920M (by site directed mutagenesis) in the GEF2 domain of Trio or in Tgat, and have produced recombinant GST-fusion proteins. In vitro nucleotide exchange assays have been performed as described (Bouquier et al., 2009) in order to assess the GEF activity of the mutant.

Example 4

Delivery of the Peptides into the Cells

Therapeutic peptides have great potential as anticancer agents, owing to their ease of rational design and target specificity. However, the main hurdle to their in vivo application for cancer therapy is their low stability and poor tumor penetration. Therefore, successful development of various strategies for efficient peptide delivery could make possible the use of this new and very promising class of anticancer agents.

In this context the inventors have developed different approaches in order to increase the stability and deliverability of the TRIP peptides. The inventors will take advantage of the advances in peptide chemistry and delivery that have been made recently (Borghouts et al., 2005b).
  A. Increasing peptide stability
    Stability of the peptide is an important issue to be addressed. There are technologies available to increase the half-life of peptides, like for example the use of fused-recombinant proteins or the use of non-natural amino acids (for more details see Borghouts et al., 2005a).
    The inventors have then produced such construction comprising non-natural amino acids, without affecting the essential residues defined in example 1 (Black bold residues)
  B. Delivery of the peptides across the cell membrane.
    To date there are mainly two ways of getting peptides efficiently into cells: fusing the peptide to a second, cell-permeable, peptide or using a lentiviral vector that carries a gene encoding the peptide.
    A variety of cell-penetrating peptides have been described in the past few years, including Penetratin™ (the third helix of the *Drosophila* Antennapedia homeodomain) and TAT-derived sequences (the protein transduction domain of the HIV virus), which are able to transduce fused proteins across the plasma membrane, without cytotoxicity or immunogenicity. In this context, the inventors will fuse the TAT-derived peptide to $TRIP^{E32G}$ peptide (for instance SEQ ID NO: 4), and apply it directly to cells in the culture medium. The above mentioned readouts will be used to assess the efficient delivery and effect of the peptide in the cell.
    Lentiviral vectors are also a promising alternative for the in vivo use of peptides aptamers. The inventors have used retroviral vectors (Bouquier et al., 2009), and have also improved the use of such vectors with new generation lentiviral vectors.
  C. Aptamer-displacement screen
    An alternative, elegant, method to circumvent the problem of in vivo delivery is the use of an aptamer-displacement screen, in which a small-molecule library is screened for compounds that displace the aptamer from its target and reproduce its inhibitory activity, thus converting an aptamer into a small compound inhibitor (Baines and Colas, 2006). The advantage is that the corresponding compound targets the same site and shares the same properties as the already characterized peptide, and shows cell-permeable features. To perform such an aptamer-displacement screen, the inventors have used the high-throughput screening assay as described (Bardou et al., 2009). AptaScreen is a duplex yeast two-hybrid assay featuring two luciferase reporter genes. It can be performed in 96- or 384-well plates and can be fully automated. For details of the experimental procedure, see (Bardou et al., 2009). The library of compounds used is purchased from ChemBridge (San Diego, Calif., USA).

Example 5

Materials and Methods of Example 2

DNA Constructs—
The Trio mutants were obtained using the Quick Change Site Directed Mutagenesis Kit (Stratagene Inc.), according to the manufacturer's instructions. To create stable NIH3T3 cell lines, GFP-tagged Tgat and full length Trio were cloned into the puromycin-resistant retroviral vector pBabePuro.

Recombinant Proteins—
Recombinant GST-Trio DH2-PH2, GST-Tgat were purified as described previously (Bouquier et al., 2009; Schmidt et al., 2002).

RhoA Activation Assay in Cells—
The level of GTP-bound RhoA was measured by a GST pull-down assay as described (Bouquier et al., 2009). Briefly, cell lysates were incubated with glutathione beads coated with the recombinant Rho-binding domain (RBD) of the RhoA-specific effector Rhotekin (Cytoskeleton Inc.). Total or GTP-bound RhoA in the samples was revealed by Western blot analysis, using a monoclonal anti-RhoA antibody (Santa-Cruz Biotechnology Inc.).

Nucleotide Exchange Inhibition Assays—
Mant-GTP fluorescence nucleotide exchange assays are performed as described (Bouquier et al., 2009), in a $FL_X800$ Microplate Fluorescence Reader (BioTek Instruments). Briefly, 0.5 µM Tgat or Trio DH2-PH2 (wild type or mutated) are preincubated 5 min at 25° C. in the presence of 20 µM GST, $GST-TRIP^{E32G}$ and 1 µM mant-GTP. The exchange reaction is initiated by addition of 1 µM RhoA and monitored for 10 min.

Cell Lines, Transfection—
NIH3T3 cells were maintained as described previously (Sirvent et al., 2007). NIH3T3 cell lines stably expressing the different Trio mutants with or without the GST-TRIP peptides, were generated as follows: the indicated retroviral constructs were transfected into BOSC packaging cells, using the Jet PEI reagent, according to the manufacturer's protocol (QBiogene Inc.). Forty-eight hours after transfection, virus-containing supernatants were collected and used to infect NIH3T3 cells. Infected cells were selected with 6 µg/mL puromycin and/or 1 mg/mL G418 and stable transfectants were pooled after selection. mRNA levels in the different cell lines were monitored by RT-PCR, and protein expression levels by Western blot analysis using a polyclonal anti-GFP antibody (Torrey Pines Laboratories).

Cell Growth Assay:
the growth rate of the NIH3T3 cells stably expressing the different Trio mutants is measured by the CellTiter 96 Aqueous assay (Promega), according to the manufacturer's instructions. 1500 cells per well in 200 µl of 5% FBS medium were plated in 96-well plates and were grown under normal conditions.

Focus Formation Assays—
Focus formation assays are performed using stable NIH3T3 cell lines as indicated, seeded at $5 \times 10^4$ cells in 6-well plates and maintained for 15 to 21 days in 10% FBS. Medium is renewed every two days. After staining with Crystal Violet (1%), plates are photographed and foci are scored using the Metamorph software. All experiments are done in triplicate.

Anchorage-Independent Growth Assay—

NIH3T3 cells stably expressing the different Trio mutants ($1.25 \times 10^3$ per well) are grown in 0.3% agarose, in a six-well plate. Duplicate wells are tested for each condition. The cells are fed with 1 ml of top agar once every week. Colonies are scored after 3 to 5 weeks.

Wound-Healing Assay—

Confluent cells stably expressing the TRIP peptides in a 24-multiwell plate were wounded with a sterile pipette tip and exposed to 10% FBS-DMEM. Plates were kept at 37° C. in a 5% CO2 of a Zeiss inverted microscope equipped with a motorized stage. One field that includes the scratched path from each dish was selected and scanned sequentially every 15 min for 20 h.

Cell Invasion Assay—

Cell invasion assays are performed using the 6.4-mm Biocoat Matrigel invasion chambers equipped with the 8 µm pore sized PET membrane filters (BD Biosciences) according to the manufacturer's instructions. Briefly, $2.5 \times 10^4$ cells are suspended in 0.5 ml of culture medium and were added to the upper chamber. 10% FBS in the culture medium is plated in the lower chamber as chemoattractant. Cells in the invasion chambers are incubated in a humidified incubator. The cells that traversed the Matrigel matrix and the 8 µm membrane pores and spread to the lower surface of the filters are stained with 5% Giemsa solution for visualization. Each data point of the invasion test is derived from triplicate chambers, and error bars represent the mean standard error.

Lung Colonization Model—

Twenty 6- to 8-wk-old female nude mice are injected with a breast cancer cell line expressing, or not, TRIPE32G (Bouquier et al., 2009) ($2.5 \times 106$ cells in 100 µL of sterile PBS, 97% viability) in the tail vein. After 22 d, mice are weighted and sacrificed by cervical dislocation. Lungs are removed, sectioned, and fixed in buffered 4% formaldehyde and examined blindly. The number of lung metastases is assessed in three H&E-stained sections per mouse and expressed as mean metastases number/mm2. The extent of normal and tumor lung parenchyma is measured in three fields per sample on H&E-stained sections. Area of lung metastasis is assessed using the Axiovision 4.4 software. Right lower lobe from each lung is lysed, and 50 µg proteins/sample were analyzed by Western blot using 1 µg/mL anti-GFP antibody or 1 µg/mL anti-α-tubulin mAb (Sigma-Aldrich). Densitometry was done by AIDA software. Statistical analysis was done using the Student's t test. Differences were considered statistically significant if $P<0.05$.

Adamowicz, M., Radlwimmer, B., Rieker, R. J., Mertens, D., Schwarzbach, M., Schraml, P., Benner, A., Lichter, P., Mechtersheimer, G., and Joos, S. (2006). Frequent amplifications and abundant expression of TRIO, NKD2, and IRX2 in soft tissue sarcomas. Genes Chromosomes Cancer 45, 829-838.

Baines, I. C., and Colas, P. (2006). Peptide aptamers as guides for small-molecule drug discovery. Drug Discov Today 11, 334-341.

Baldwin, C., Garnis, C., Zhang, L., Rosin, M. P., and Lam, W. L. (2005). Multiple microalterations detected at high frequency in oral cancer. Cancer Res 65, 7561-7567.

Bardou, C., Borie, C., Bickle, M., Rudkin, B. B., and Colas, P. (2009). Peptide aptamers for small molecule drug discovery. Methods Mol Biol 535, 373-388.

Bellanger, J. M., Lazaro, J. B., Diriong, S., Fernandez, M., Lamb, N., and Debant, A. (1998). The two guanine nucleotide exchange factor domains of Trio link the Rac1 and the RhoA pathways in vivo. Oncogene 16, 147-152.

Bellanger, J. M., Estrach, S., Schmidt, S., Briancon-Marjollet, A., Zugasti, O., Fromont, S., and Debant, A. (2003). Different regulation of the Trio Dbl-Homology domains by their associated PH domains. Biol Cell 95, 625-634.

Bickle, M. B., Dusserre, E., Moncorge, O., Bottin, H., and Colas, P. (2006). Selection and characterization of large collections of peptide aptamers through optimized yeast two-hybrid procedures. Nat Protoc 1, 1066-1091.

Blangy, A., Vignal, E., Schmidt, S., Debant, A., Gauthier-Rouviere, C., and Fort, P. (2000). TrioGEF1 controls Rac- and Cdc42-dependent cell structures through the direct activation of RhoG. J Cell Sci 113, 729-739.

Blangy, A., Bouquier, N., Gauthier-Rouviere, C., Schmidt, S., Debant, A., Leonetti, J. P., and Fort, P. (2006). Identification of TRIO-GEFD1 chemical inhibitors using the yeast exchange assay. Biol Cell 98, 511-522.

Borghouts, C., Kunz, C., and Groner, B. (2005a). Current strategies for the development of peptide-based anti-cancer therapeutics. J Pept Sci 11, 713-726.

Borghouts, C., Kunz, C., and Groner, B. (2005b). Peptide aptamers: recent developments for cancer therapy. Expert Opin Biol Ther 5, 783-797.

Bos, J. L., Rehmann, H., and Wittinghofer, A. (2007). GEFs and GAPs: critical elements in the control of small G proteins. Cell 129, 865-877.

Bouquier, N., Fromont, S., Zeeh, J. C., Auziol, C., Larrousse, P., Robert, B., Zeghouf, M., Cherfils, J., Debant, A., and Schmidt, S. (2009). Aptamer-derived peptides as potent inhibitors of the oncogenic RhoGEF Tgat. Chem Biol 16, 391-400.

Briancon-Marjollet, A., Ghogha, A., Nawabi, H., Triki, I., Auziol, C., Fromont, S., Piche, C., Enslen, H., Chebli, K., Cloutier, J. F., et al. (2008). Trio mediates netrin-1-induced Rac1 activation in axon outgrowth and guidance. Mol Cell Biol 28, 2314-2323.

Butz, K., Denk, C., Ullmann, A., Scheffner, M., and Hoppe-Seyler, F. (2000). Induction of apoptosis in human papillomaviruspositive cancer cells by peptide aptamers targeting the viral E6 oncoprotein. Proc Natl Acad Sci USA 97, 6693-6697.

Calaf, G. M., and Roy, D. (2007a). Gene and protein expressions induced by 17beta-estradiol and parathion in cultured breast epithelial cells. Mol Med 13, 255-265.

Calaf, G. M., and Roy, D. (2007b). Gene expression signature of parathion-transformed human breast epithelial cells. Int J Mol Med 19, 741-750.

Chhatriwala, M. K., Betts, L., Worthylake, D. K., and Sondek, J. (2007). The DH and PH domains of Trio coordinately engage Rho GTPases for their efficient activation. J Mol Biol 368, 1307-1320.

Coe, B. P., Henderson, L. J., Garnis, C., Tsao, M. S., Gazdar, A. F., Minna, J., Lam, S., Macaulay, C., and Lam, W. L. (2005). High-resolution chromosome arm 5p array CGH analysis of small cell lung carcinoma cell lines. Genes Chromosomes Cancer 42, 308-313.

Colas, P., Cohen, B., Jessen, T., Grishina, I., McCoy, J., and Brent, R. (1996). Genetic selection of peptide aptamers that recognize and inhibit cyclin-dependent kinase 2. Nature 380, 548-550.

Crnkovic-Mertens, I., Hoppe-Seyler, F., and Butz, K. (2003). Induction of apoptosis in tumor cells by siRNA-mediated silencing of the livin/ML-IAP/KIAP gene. Oncogene 22, 8330-8336.

Desire, L., Bourdin, J., Loiseau, N., Peillon, H., Picard, V., De Oliveira, C., Bachelot, F., Leblond, B., Taverne, T., Beausoleil, E., et al. (2005). RAC1 inhibition targets amyloid precursor protein processing by gamma-secretase and decreases Abeta production in vitro and in vivo. J Biol Chem 280, 37516-37525.

Estrach, S., Schmidt, S., Diriong, S., Penna, A., Blangy, A., Fort, P., and Debant, A. (2002). The Human Rho-GEF trio and its target GTPase RhoG are involved in the NGF pathway, leading to neurite outgrowth. Curr Biol 12, 307-312.

Etienne-Manneville, S., and Hall, A. (2002). Rho GTPases in cell biology. Nature 420, 629-635.

Eva, A., and Aaronson, S. A. (1985). Isolation of a new human oncogene from a diffuse Bcell lymphoma. Nature 316, 273-275.

Fabbrizio, E., Le Cam, L., Polanowska, J., Kaczorek, M., Lamb, N., Brent, R., and Sardet, C. (1999). Inhibition of mammalian cell proliferation by genetically selected peptide aptamers that functionally antagonize E2F activity. Oncogene 18, 4357-4363.

Forozan, F., Mahlamaki, E. H., Monni, O., Chen, Y., Veldman, R., Jiang, Y., Gooden, G. C., Ethier, S. P., Kallioniemi, A., and Kallioniemi, O. P. (2000). Comparative genomic hybridization analysis of 38 breast cancer cell lines: a basis for interpreting complementary DNA microarray data. Cancer Res 60, 4519-4525.

Gao, Y., Dickerson, J. B., Guo, F., Zheng, J., and Zheng, Y. (2004). Rational design and characterization of a Rac GTPase-specific small molecule inhibitor. Proc Natl Acad Sci USA 101, 7618-7623.

Garnis, C., Davies, J. J., Buys, T. P., Tsao, M. S., MacAulay, C., Lam, S., and Lam, W. L. (2005). Chromosome 5p aberrations are early events in lung cancer: implication of glial cell line-derived neurotrophic factor in disease progression. Oncogene 24, 4806-4812.

Greenman, C., Stephens, P., Smith, R., Dalgliesh, G. L., Hunter, C., Bignell, G., Davies, H., Teague, J., Butler, A., Stevens, C., et al. (2007). Patterns of somatic mutation in human cancer genomes. Nature 446, 153-158.

Hafner, M., Schmitz, A., Grune, I., Srivatsan, S. G., Paul, B., Kolanus, W., Quast, T., Kremmer, E., Bauer, I., and Famulok, M. (2006). Inhibition of cytohesins by SecinH3 leads to hepatic insulin resistance. Nature 444, 941-944.

Hoppe-Seyler, F., Crnkovic-Mertens, I., Tomai, E., and Butz, K. (2004). Peptide aptamers: specific inhibitors of protein function. Curr Mol Med 4, 529-538.

Katzav, S., Martin-Zanca, D., and Barbacid, M. (1989). vav, a novel human oncogene derived from a locus ubiquitously expressed in hematopoietic cells. Embo J 8, 2283-2290.

Kloth, J. N., Oosting, J., van Wezel, T., Szuhai, K., Knijnenburg, J., Gorter, A., Kenter, G. G., Fleuren, G. J., and Jordanova, E. S. (2007). Combined array-comparative genomic hybridization and single-nucleotide polymorphism-loss of heterozygosity analysis reveals complex genetic alterations in cervical cancer. BMC Genomics 8, 53.

Lane, J., Martin, T. A., Mansel, R. E., and Jiang, W. G. (2008). The expression and prognostic value of the guanine nucleotide exchange factors (GEFs) Trio, Vav1 and TIAM-1 in human breast cancer. Int Semin Surg Oncol 5, 23.

Lutz, S., Shankaranarayanan, A., Coco, C., Ridilla, M., Nance, M. R., Vettel, C., Baltus, D., Evelyn, C. R., Neubig, R. R., Wieland, T., and Tesmer, J. J. (2007). Structure of Galphaqp63RhoGEF-RhoA complex reveals a pathway for the activation of RhoA by GPCRs. Science 318, 1923-1927.

Martel, V., Filhol, O., Colas, P., and Cochet, C. (2006). p53-dependent inhibition of mammalian cell survival by a genetically selected peptide aptamer that targets the regulatory subunit of protein kinase CK2. Oncogene 25, 7343-7353.

Mayer, G., Blind, M., Nagel, W., Bohm, T., Knorr, T., Jackson, C. L., Kolanus, W., and Famulok, M. (2001). Controlling small guanine-nucleotide-exchange factor function through cytoplasmic RNA intramers. Proc Natl Acad Sci USA 98, 4961-4965.

Mhawech-Fauceglia, P., Cheney, R. T., and Schwaller, J. (2006). Genetic alterations in urothelial bladder carcinoma: an updated review. Cancer 106, 1205-1216.

Miki, T., Smith, C. L., Long, J. E., Eva, A., and Fleming, T. P. (1993). Oncogene ect2 is related to regulators of small GTP-binding proteins. Nature 362, 462-465.

Mori, T., Moriuchi, R., Okazaki, E., Yamada, K., and Katamine, S. (2007). Tgat oncoprotein functions as a inhibitor of RECK by association of the unique C-terminal region. Biochem Biophys Res Commun 355, 937-943.

Newsome, T. P., Schmidt, S., Dietzl, G., Keleman, K., Asling, B., Debant, A., and Dickson, B. J. (2000). Trio combines with dock to regulate Pak activity during photoreceptor axon pathfinding in Drosophila. Cell 101, 283-294.

Ng, G., Winder, D., Muralidhar, B., Gooding, E., Roberts, I., Pett, M., Mukherjee, G., Huang, J., and Coleman, N. (2007). Gain and overexpression of the oncostatin M receptor occur frequently in cervical squamous cell carcinoma and are associated with adverse clinical outcome. J Pathol 212, 325-334.

Nouvion, A. L., Thibaut, J., Lohez, O. D., Venet, S., Colas, P., Gillet, G., and Lalle, P. (2007). Modulation of Nr-13 antideath activity by peptide aptamers. Oncogene 26, 701-710.

Oleksy, A., Barton, H., Devedjiev, Y., Purdy, M., Derewenda, U., Otlewski, J., and Derewenda, Z. S. (2004). Preliminary crystallographic analysis of the complex of the human GTPase RhoA with the DH/PH tandem of PDZ-RhoGEF. Acta Crystallogr D Biol Crystallogr 60, 740-742.

Rojas, R. J., Yohe, M. E., Gershburg, S., Kawano, T., Kozasa, T., and Sondek, J. (2007). Galphaq directly activates p63RhoGEF and Trio via a conserved extension of the Dbl homology-associated pleckstrin homology domain. J Biol Chem 282, 29201-29210.

Rossman, K. L., Cheng, L., Mahon, G. M., Rojas, R. J., Snyder, J. T., Whitehead, I. P., and Sondek, J. (2003). Multifunctional roles for the PH domain of Dbs in regulating Rho GTPase activation. J Biol Chem 278, 18393-18400.

Rossman, K. L., Der, C. J., and Sondek, J. (2005). GEF means go: turning on RHO GTPases with guanine nucleotide-exchange factors. Nat Rev Mol Cell Biol 6, 167-180.

Salhia, B., Tran, N. L., Chan, A., Wolf, A., Nakada, M., Rutka, F., Ennis, M., McDonough, W. S., Berens, M. E., Symons, M., et al. (2008). The guanine nucleotide exchange factors trio, Ect2, and Vav3 mediate the invasive behavior of glioblastoma. Am J Pathol 173, 1828-1838.

Sardet, C., Vidal, M., Cobrinik, D., Geng, Y., Onufryk, C., Chen, A., and Weinberg, R. A. (1995). E2F-4 and E2F-5, two members of the E2F family, are expressed in the early phases of the cell cycle. Proc Natl Acad Sci USA 92, 2403-2407.

Schmidt, S., Diriong, S., Mery, J., Fabbrizio, E., and Debant, A. (2002). Identification of the first Rho-GEF inhibitor, TRIPalpha, which targets the RhoA-specific GEF domain of Trio. FEBS Lett 523, 35-42. Sahai, E., and Marshall, C. J. (2002). RHO-GTPases and cancer. Nat Rev Cancer 2, 133-142.

Shutes, A., Onesto, C., Picard, V., Leblond, B., Schweighoffer, F., and Der, C. J. (2007). Specificity and mechanism of action of EHT 1864, a novel small molecule inhibitor of Rac family small GTPases. J Biol Chem 282, 35666-35678.

Sirvent, A., Boureux, A., Simon, V., Leroy, C., and Roche, S. (2007). The tyrosine kinase Abl is required for Src-transforming activity in mouse fibroblasts and human breast cancer cells. Oncogene 26, 7313-7323.

Souchet, M., Portales-Casamar, E., Mazurais, D., Schmidt, S., Leger, I., Javre, J. L., Robert, P., Berrebi-Bertrand, I., Bril, A., Gout, B., et al. (2002). Human p63RhoGEF, a novel RhoAspecific guanine nucleotide exchange factor, is localized in cardiac sarcomere. J Cell Sci 115, 629-640.

Steven, R., Kubiseski, T. J., Zheng, H., Kulkarni, S., Mancillas, J., Ruiz Morales, A., Hogue, C. W., Pawson, T., and Culotti, J. (1998). UNC-73 activates the Rac GTPase and is required for cell and growth cone migrations in C. elegans. Cell 92, 785-795.

Toksoz, D., and Merdek, K. D. (2002). The Rho small GTPase: functions in health and disease. Histol Histopathol 17, 915-927.

Viaud, J., Zeghouf, M., Barelli, H., Zeeh, J. C., Padilla, A., Guibert, B., Chardin, P., Royer, C. A., Cherfils, J., and Chavanieu, A. (2007). Structure-based discovery of an inhibitor of Arf activation by Sec7 domains through targeting of protein-protein complexes. Proc Natl Acad Sci USA 104, 10370-10375.

Whitehead, I., Kirk, H., Tognon, C., Trigo-Gonzalez, G., and Kay, R. (1995). Expression cloning of lfc, a novel oncogene with structural similarities to guanine nucleotide exchange factors and to the regulatory region of protein kinase C. J Biol Chem 270, 18388-18395.

Whitehead, I. P., Khosravi-Far, R., Kirk, H., Trigo-Gonzalez, G., Der, C. J., and Kay, R. (1996). Expression cloning of lsc, a novel oncogene with structural similarities to the Dbl family of guanine nucleotide exchange factors. J Biol Chem 271, 18643-18650.

Yamada, K., Moriuchi, R., Mori, T., Okazaki, E., Kohno, T., Nagayasu, T., Matsuyama, T., and Katamine, S. (2007). Tgat, a Rho-specific guanine nucleotide exchange factor, activates NF-kappaB via physical association with IkappaB kinase complexes. Biochem Biophys Res Commun 355, 269-274.

Yoshizuka, N., Moriuchi, R., Mori, T., Yamada, K., Hasegawa, S., Maeda, T., Shimada, T., Yamada, Y., Kamihira, S., Tomonaga, M., and Katamine, S. (2004). An alternative transcript derived from the trio locus encodes a guanosine nucleotide exchange factor with mouse cell transforming potential. J Biol Chem 279, 43998-44004.

Zeeh, J. C., Zeghouf, M., Grauffel, C., Guibert, B., Martin, E., Dejaegere, A., and Cherfils, J. (2006). Dual specificity of the interfacial inhibitor brefeldin a for arf proteins and sec7 domains. J Biol Chem 281, 11805-11814.

Zheng, M., Simon, R., Mirlacher, M., Maurer, R., Gasser, T., Forster, T., Diener, P. A., Mihatsch, M. J., Sauter, G., and Schraml, P. (2004). TRIO amplification and abundant mRNA expression is associated with invasive tumor growth and rapid tumor cell proliferation in urinary bladder cancer. Am J Pathol 165, 63-69.

The invention claimed is:

1. A method for treating cancer, comprising administering to a subject in need thereof a therapeutically effective amount of an isolated peptide comprising the amino acid sequence SEQ ID NO: 3

$$ICGYX_{13}LAX_{16}X_{17}X_{18}MLGPX_{23}X_{24}RVX_{27}CPLCX_{32}P$$

wherein $X_{13}$, $X_{16}$, $X_{17}$, $X_{18}$, $X_{23}$, $X_{24}$, $X_{27}$ and $X_{32}$ represent any amino acids, and having at least one of the following features:

$X_{13}$ is D;
$X_{16}$ is M or A;
$X_{17}$ is S;
$X_{18}$ is D, G or A;
$X_{23}$ is G;
$X_{24}$ is A;
$X_{27}$ is L; and
$X_{32}$ is G.

2. The method according to claim 1, wherein said peptide comprises the amino acid sequence selected from the group consisting of SEQ ID NO: 4 to SEQ ID NO: 51.

3. The method according to claim 1, wherein said peptide further comprises fragments of thioredoxin A, said fragments flanking the N-terminal and C-terminal of said peptide of SEQ ID NO: 3.

4. The method according to claim 3, wherein said peptide comprises the amino acid sequence selected from the group consisting of SEQ ID NO: 52 to SEQ ID NO: 99.

5. The method according to claim 1, wherein the cancer is leukemia, T-cell acute Leukemia, sarcoma, lung cancer or breast cancer.

* * * * *

SEQUENCE LISTING

```
<160> NUMBER OF SEQ ID NOS: 197

<210> SEQ ID NO 1
<211> LENGTH: 25
<212> TYPE: PRT
<213> ORGANISM: Artificial sequence
<220> FEATURE:
<223> OTHER INFORMATION: fragment 9-33 of TRIP alpha

<400> SEQUENCE: 1

Ile Cys Gly Tyr Asn Leu Ala Thr Leu Val Met Leu Gly Pro Ser Glu
1               5                   10                  15

Arg Val Phe Cys Pro Leu Cys Glu Pro
            20                  25

<210> SEQ ID NO 2
<211> LENGTH: 25
<212> TYPE: PRT
<213> ORGANISM: Artificial sequence
<220> FEATURE:
<223> OTHER INFORMATION: peptide derived from TRIP alpha
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (12)..(19)
<223> OTHER INFORMATION: Xaa can be any naturally occurring amino acid
<220> FEATURE:
```

```
<221> NAME/KEY: misc_feature
<222> LOCATION: (24)..(25)
<223> OTHER INFORMATION: Xaa can be any naturally occurring amino acid

<400> SEQUENCE: 2

Xaa Cys Gly Tyr Xaa Xaa Ala Xaa Xaa Xaa Met Xaa Xaa Xaa Xaa Xaa
1               5                   10                  15

Xaa Xaa Xaa Cys Pro Leu Cys Xaa Xaa
            20                  25

<210> SEQ ID NO 3
<211> LENGTH: 25
<212> TYPE: PRT
<213> ORGANISM: Artificial sequence
<220> FEATURE:
<223> OTHER INFORMATION: peptide derived from TRIP alpha
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 3

Ile Cys Gly Tyr Asn Leu Ala Xaa Leu Xaa Met Leu Gly Pro Ser Glu
1               5                   10                  15

Arg Val Phe Cys Pro Leu Cys Xaa Pro
            20                  25

<210> SEQ ID NO 4
<211> LENGTH: 25
<212> TYPE: PRT
<213> ORGANISM: Artificial sequence
<220> FEATURE:
<223> OTHER INFORMATION: peptide derived from TRIP alpha

<400> SEQUENCE: 4

Ile Cys Gly Tyr Asn Leu Ala Thr Leu Val Met Leu Gly Pro Ser Glu
1               5                   10                  15

Arg Val Phe Cys Pro Leu Cys Gly Pro
            20                  25

<210> SEQ ID NO 5
<211> LENGTH: 25
<212> TYPE: PRT
<213> ORGANISM: Artificial sequence
<220> FEATURE:
<223> OTHER INFORMATION: peptide derived from TRIP alpha

<400> SEQUENCE: 5

Ile Cys Gly Tyr Asn Leu Ala Met Ser Val Met Leu Gly Pro Ser Glu
1               5                   10                  15

Arg Val Phe Cys Pro Leu Cys Glu Pro
            20                  25

<210> SEQ ID NO 6
<211> LENGTH: 25
<212> TYPE: PRT
<213> ORGANISM: Artificial sequence
<220> FEATURE:
<223> OTHER INFORMATION: peptide derived from TRIP alpha
```

```
<400> SEQUENCE: 6

Ile Cys Gly Tyr Asn Leu Ala Met Leu Val Met Leu Gly Pro Ser Glu
1               5                   10                  15

Arg Val Phe Cys Pro Leu Cys Glu Pro
            20                  25

<210> SEQ ID NO 7
<211> LENGTH: 25
<212> TYPE: PRT
<213> ORGANISM: Artificial sequence
<220> FEATURE:
<223> OTHER INFORMATION: peptide derived from TRIP alpha

<400> SEQUENCE: 7

Ile Cys Gly Tyr Asn Leu Ala Thr Ser Val Met Leu Gly Pro Ser Glu
1               5                   10                  15

Arg Val Phe Cys Pro Leu Cys Glu Pro
            20                  25

<210> SEQ ID NO 8
<211> LENGTH: 25
<212> TYPE: PRT
<213> ORGANISM: Artificial sequence
<220> FEATURE:
<223> OTHER INFORMATION: peptide derived from TRIP alpha

<400> SEQUENCE: 8

Ile Cys Gly Tyr Asn Leu Ala Met Leu Val Met Leu Gly Pro Gly Glu
1               5                   10                  15

Arg Val Phe Cys Pro Leu Cys Glu Pro
            20                  25

<210> SEQ ID NO 9
<211> LENGTH: 25
<212> TYPE: PRT
<213> ORGANISM: Artificial sequence
<220> FEATURE:
<223> OTHER INFORMATION: peptide derived from TRIP alpha

<400> SEQUENCE: 9

Ile Cys Gly Tyr Asn Leu Ala Thr Leu Asp Met Leu Gly Pro Ser Glu
1               5                   10                  15

Arg Val Leu Cys Pro Leu Cys Glu Pro
            20                  25

<210> SEQ ID NO 10
<211> LENGTH: 25
<212> TYPE: PRT
<213> ORGANISM: Artificial sequence
<220> FEATURE:
<223> OTHER INFORMATION: peptide derived from TRIP alpha

<400> SEQUENCE: 10

Ile Cys Gly Tyr Asn Leu Ala Thr Leu Val Met Leu Gly Pro Ser Glu
1               5                   10                  15

Arg Val Phe Cys Pro Leu Cys Gly Pro
            20                  25

<210> SEQ ID NO 11
<211> LENGTH: 25
<212> TYPE: PRT
<213> ORGANISM: Artificial sequence
<220> FEATURE:
```

<223> OTHER INFORMATION: peptide derived from TRIP alpha

<400> SEQUENCE: 11

Ile Cys Gly Tyr Asn Leu Ala Ala Leu Gly Met Leu Gly Pro Ser Glu
1               5                   10                  15

Arg Val Phe Cys Pro Leu Cys Gly Pro
            20                  25

<210> SEQ ID NO 12
<211> LENGTH: 25
<212> TYPE: PRT
<213> ORGANISM: Artificial sequence
<220> FEATURE:
<223> OTHER INFORMATION: peptide derived from TRIP alpha

<400> SEQUENCE: 12

Ile Cys Gly Tyr Asn Leu Ala Thr Leu Ala Met Leu Gly Pro Ser Ala
1               5                   10                  15

Arg Val Phe Cys Pro Leu Cys Gly Pro
            20                  25

<210> SEQ ID NO 13
<211> LENGTH: 25
<212> TYPE: PRT
<213> ORGANISM: Artificial sequence
<220> FEATURE:
<223> OTHER INFORMATION: peptide derived from TRIP alpha

<400> SEQUENCE: 13

Ile Cys Gly Tyr Asp Leu Ala Met Leu Val Met Leu Gly Pro Ser Glu
1               5                   10                  15

Arg Val Phe Cys Pro Leu Cys Glu Pro
            20                  25

<210> SEQ ID NO 14
<211> LENGTH: 25
<212> TYPE: PRT
<213> ORGANISM: Artificial sequence
<220> FEATURE:
<223> OTHER INFORMATION: peptide derived from TRIP alpha

<400> SEQUENCE: 14

Ile Cys Gly Tyr Asn Leu Ala Ala Ser Val Met Leu Gly Pro Ser Glu
1               5                   10                  15

Arg Val Phe Cys Pro Leu Cys Glu Pro
            20                  25

<210> SEQ ID NO 15
<211> LENGTH: 25
<212> TYPE: PRT
<213> ORGANISM: Artificial sequence
<220> FEATURE:
<223> OTHER INFORMATION: peptide derived from TRIP alpha

<400> SEQUENCE: 15

Ile Cys Gly Tyr Asn Leu Ala Thr Leu Asp Met Leu Gly Pro Ser Glu
1               5                   10                  15

Arg Val Phe Cys Pro Leu Cys Glu Pro
            20                  25

<210> SEQ ID NO 16
<211> LENGTH: 33
<212> TYPE: PRT
<213> ORGANISM: Artificial sequence

```
<220> FEATURE:
<223> OTHER INFORMATION: peptide derived from TRIP alpha

<400> SEQUENCE: 16

Ala Arg Glu Gly Ala Asp Gly Ala Ile Cys Gly Tyr Asn Leu Ala Thr
1               5                   10                  15

Leu Val Met Leu Gly Pro Ser Glu Arg Val Phe Cys Pro Leu Cys Gly
            20                  25                  30

Pro

<210> SEQ ID NO 17
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 17

Ala Arg Glu Gly Ala Asp Gly Ala Ile Cys Gly Tyr Asn Leu Ala Met
1               5                   10                  15

Ser Val Met Leu Gly Pro Ser Glu Arg Val Phe Cys Pro Leu Cys Glu
            20                  25                  30

Pro

<210> SEQ ID NO 18
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 18

Ala Arg Glu Gly Ala Asp Gly Ala Ile Cys Gly Tyr Asn Leu Ala Met
1               5                   10                  15

Leu Val Met Leu Gly Pro Ser Glu Arg Val Phe Cys Pro Leu Cys Glu
            20                  25                  30

Pro

<210> SEQ ID NO 19
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 19

Ala Arg Glu Gly Ala Asp Gly Ala Ile Cys Gly Tyr Asn Leu Ala Thr
1               5                   10                  15

Ser Val Met Leu Gly Pro Ser Glu Arg Val Phe Cys Pro Leu Cys Glu
            20                  25                  30

Pro

<210> SEQ ID NO 20
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 20

Ala Arg Glu Gly Ala Asp Gly Ala Ile Cys Gly Tyr Asn Leu Ala Met
1               5                   10                  15
```

Leu Val Met Leu Gly Pro Gly Glu Arg Val Phe Cys Pro Leu Cys Glu
            20                  25                  30

Pro

<210> SEQ ID NO 21
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 21

Thr Arg Glu Gly Ala Asp Gly Ala Ile Cys Gly Tyr Asn Leu Ala Thr
1               5                   10                  15

Leu Asp Met Leu Gly Pro Ser Glu Arg Val Leu Cys Pro Leu Cys Glu
            20                  25                  30

Pro

<210> SEQ ID NO 22
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 22

Ala Arg Glu Gly Ala Asp Gly Ala Ile Cys Gly Tyr Asn Leu Ala Thr
1               5                   10                  15

Leu Val Met Leu Gly Pro Ser Glu Arg Val Phe Cys Pro Leu Cys Gly
            20                  25                  30

Pro

<210> SEQ ID NO 23
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 23

Ala Arg Glu Gly Ala Asp Gly Ala Ile Cys Gly Tyr Asn Leu Ala Ala
1               5                   10                  15

Leu Gly Met Leu Gly Pro Ser Glu Arg Val Phe Cys Pro Leu Cys Gly
            20                  25                  30

Pro

<210> SEQ ID NO 24
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 24

Ala Arg Glu Gly Ala Asp Gly Ala Ile Cys Gly Tyr Asn Leu Ala Thr
1               5                   10                  15

Leu Ala Met Leu Gly Pro Ser Ala Arg Val Phe Cys Pro Leu Cys Gly
            20                  25                  30

Pro

```
<210> SEQ ID NO 25
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 25

Ala Arg Glu Gly Ala Asp Gly Ala Ile Cys Gly Tyr Asp Leu Ala Met
1               5                   10                  15

Leu Val Met Leu Gly Pro Ser Glu Arg Val Phe Cys Pro Leu Cys Glu
            20                  25                  30

Pro

<210> SEQ ID NO 26
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 26

Ala Arg Glu Gly Ala Asp Gly Ala Ile Cys Gly Tyr Asn Leu Ala Ala
1               5                   10                  15

Ser Val Met Leu Gly Pro Ser Glu Arg Val Phe Cys Pro Leu Cys Glu
            20                  25                  30

Pro

<210> SEQ ID NO 27
<211> LENGTH: 33
<212> TYPE: PRT
<213> ORGANISM: Artificial sequence
<220> FEATURE:
<223> OTHER INFORMATION: peptide derived from TRIP alpha

<400> SEQUENCE: 27

Ala Arg Glu Gly Ala Asp Gly Ala Ile Cys Gly Tyr Asn Leu Ala Thr
1               5                   10                  15

Leu Asp Met Leu Gly Pro Ser Glu Arg Val Phe Cys Pro Leu Cys Glu
            20                  25                  30

Pro

<210> SEQ ID NO 28
<211> LENGTH: 34
<212> TYPE: PRT
<213> ORGANISM: Artificial sequence
<220> FEATURE:
<223> OTHER INFORMATION: peptide derived from TRIP alpha

<400> SEQUENCE: 28

Ile Cys Gly Tyr Asn Leu Ala Thr Leu Val Met Leu Gly Pro Ser Glu
1               5                   10                  15

Arg Val Phe Cys Pro Leu Cys Gly Pro Cys Ser Ser Asp Ile Tyr Glu
            20                  25                  30

Leu Met

<210> SEQ ID NO 29
<211> LENGTH: 34
<212> TYPE: PRT
<213> ORGANISM: Artificial sequence
<220> FEATURE:
<223> OTHER INFORMATION: peptide derived from TRIP alpha
```

-continued

```
<400> SEQUENCE: 29

Ile Cys Gly Tyr Asn Leu Ala Met Ser Val Met Leu Gly Pro Ser Glu
1               5                   10                  15

Arg Val Phe Cys Pro Leu Cys Glu Pro Cys Ser Ser Asp Ile Tyr Glu
            20                  25                  30

Leu Met

<210> SEQ ID NO 30
<211> LENGTH: 34
<212> TYPE: PRT
<213> ORGANISM: Artificial sequence
<220> FEATURE:
<223> OTHER INFORMATION: peptide derived from TRIP alpha

<400> SEQUENCE: 30

Ile Cys Gly Tyr Asn Leu Ala Met Leu Val Met Leu Gly Pro Ser Glu
1               5                   10                  15

Arg Val Phe Cys Pro Leu Cys Glu Pro Cys Ser Ser Asp Ile Tyr Glu
            20                  25                  30

Leu Met

<210> SEQ ID NO 31
<211> LENGTH: 34
<212> TYPE: PRT
<213> ORGANISM: Artificial sequence
<220> FEATURE:
<223> OTHER INFORMATION: peptide derived from TRIP alpha

<400> SEQUENCE: 31

Ile Cys Gly Tyr Asn Leu Ala Thr Ser Val Met Leu Gly Pro Ser Glu
1               5                   10                  15

Arg Val Phe Cys Pro Leu Cys Glu Pro Cys Ser Ser Asp Ile Tyr Glu
            20                  25                  30

Leu Met

<210> SEQ ID NO 32
<211> LENGTH: 34
<212> TYPE: PRT
<213> ORGANISM: Artificial sequence
<220> FEATURE:
<223> OTHER INFORMATION: peptide derived from TRIP alpha

<400> SEQUENCE: 32

Ile Cys Gly Tyr Asn Leu Ala Met Leu Val Met Leu Gly Pro Gly Glu
1               5                   10                  15

Arg Val Phe Cys Pro Leu Cys Glu Pro Cys Ser Ser Asp Ile Tyr Glu
            20                  25                  30

Leu Met

<210> SEQ ID NO 33
<211> LENGTH: 34
<212> TYPE: PRT
<213> ORGANISM: Artificial sequence
<220> FEATURE:
<223> OTHER INFORMATION: peptide derived from TRIP alpha

<400> SEQUENCE: 33

Ile Cys Gly Tyr Asn Leu Ala Thr Leu Asp Met Leu Gly Pro Ser Glu
1               5                   10                  15

Arg Val Leu Cys Pro Leu Cys Glu Pro Cys Ser Ser Asp Ile Tyr Glu
            20                  25                  30
```

-continued

Leu Met

<210> SEQ ID NO 34
<211> LENGTH: 34
<212> TYPE: PRT
<213> ORGANISM: Artificial sequence
<220> FEATURE:
<223> OTHER INFORMATION: peptide derived from TRIP alpha

<400> SEQUENCE: 34

Ile Cys Gly Tyr Asn Leu Ala Thr Leu Val Met Leu Gly Pro Ser Glu
1               5                   10                  15

Arg Val Phe Cys Pro Leu Cys Gly Pro Cys Ser Thr Asp Ile Tyr Glu
            20                  25                  30

Leu Met

<210> SEQ ID NO 35
<211> LENGTH: 34
<212> TYPE: PRT
<213> ORGANISM: Artificial sequence
<220> FEATURE:
<223> OTHER INFORMATION: peptide derived from TRIP alpha

<400> SEQUENCE: 35

Ile Cys Gly Tyr Asn Leu Ala Ala Leu Gly Met Leu Gly Pro Ser Glu
1               5                   10                  15

Arg Val Phe Cys Pro Leu Cys Gly Pro Cys Ser Ser Asp Asn Tyr Glu
            20                  25                  30

Leu Met

<210> SEQ ID NO 36
<211> LENGTH: 34
<212> TYPE: PRT
<213> ORGANISM: Artificial sequence
<220> FEATURE:
<223> OTHER INFORMATION: peptide derived from TRIP alpha

<400> SEQUENCE: 36

Ile Cys Gly Tyr Asn Leu Ala Thr Leu Ala Met Leu Gly Pro Ser Ala
1               5                   10                  15

Arg Val Phe Cys Pro Leu Cys Gly Pro Cys Ser Ser Asp Ile Tyr Glu
            20                  25                  30

Leu Met

<210> SEQ ID NO 37
<211> LENGTH: 34
<212> TYPE: PRT
<213> ORGANISM: Artificial sequence
<220> FEATURE:
<223> OTHER INFORMATION: peptide derived from TRIP alpha

<400> SEQUENCE: 37

Ile Cys Gly Tyr Asp Leu Ala Met Leu Val Met Leu Gly Pro Ser Glu
1               5                   10                  15

Arg Val Phe Cys Pro Leu Cys Glu Pro Arg Ser Ser Asp Ile Tyr Glu
            20                  25                  30

Leu Met

<210> SEQ ID NO 38
<211> LENGTH: 34
<212> TYPE: PRT

```
<213> ORGANISM: Artificial sequence
<220> FEATURE:
<223> OTHER INFORMATION: peptide derived from TRIP alpha

<400> SEQUENCE: 38

Ile Cys Gly Tyr Asn Leu Ala Ala Ser Val Met Leu Gly Pro Ser Glu
1               5                   10                  15

Arg Val Phe Cys Pro Leu Cys Glu Pro Arg Ser Pro Asp Ile Tyr Glu
            20                  25                  30

Leu Met

<210> SEQ ID NO 39
<211> LENGTH: 34
<212> TYPE: PRT
<213> ORGANISM: Artificial sequence
<220> FEATURE:
<223> OTHER INFORMATION: peptide derived from TRIP alpha

<400> SEQUENCE: 39

Ile Cys Gly Tyr Asn Leu Ala Thr Leu Asp Met Leu Gly Pro Ser Glu
1               5                   10                  15

Arg Val Phe Cys Pro Leu Cys Glu Pro Cys Ser Ser Asp Ser Tyr Glu
            20                  25                  30

Leu Met

<210> SEQ ID NO 40
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 40

Ala Arg Glu Gly Ala Asp Gly Ala Ile Cys Gly Tyr Asn Leu Ala Thr
1               5                   10                  15

Leu Val Met Leu Gly Pro Ser Glu Arg Val Phe Cys Pro Leu Cys Gly
            20                  25                  30

Pro Cys Ser Ser Asp Ile Tyr Glu Leu Met
        35                  40

<210> SEQ ID NO 41
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 41

Ala Arg Glu Gly Ala Asp Gly Ala Ile Cys Gly Tyr Asn Leu Ala Met
1               5                   10                  15

Ser Val Met Leu Gly Pro Ser Glu Arg Val Phe Cys Pro Leu Cys Glu
            20                  25                  30

Pro Cys Ser Ser Asp Ile Tyr Glu Leu Met
        35                  40

<210> SEQ ID NO 42
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 42
```

Ala Arg Glu Gly Ala Asp Gly Ala Ile Cys Gly Tyr Asn Leu Ala Met
1               5                   10                  15

Leu Val Met Leu Gly Pro Ser Glu Arg Val Phe Cys Pro Leu Cys Glu
            20                  25                  30

Pro Cys Ser Ser Asp Ile Tyr Glu Leu Met
        35                  40

<210> SEQ ID NO 43
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 43

Ala Arg Glu Gly Ala Asp Gly Ala Ile Cys Gly Tyr Asn Leu Ala Thr
1               5                   10                  15

Ser Val Met Leu Gly Pro Ser Glu Arg Val Phe Cys Pro Leu Cys Glu
            20                  25                  30

Pro Cys Ser Ser Asp Ile Tyr Glu Leu Met
        35                  40

<210> SEQ ID NO 44
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 44

Ala Arg Glu Gly Ala Asp Gly Ala Ile Cys Gly Tyr Asn Leu Ala Met
1               5                   10                  15

Leu Val Met Leu Gly Pro Gly Glu Arg Val Phe Cys Pro Leu Cys Glu
            20                  25                  30

Pro Cys Ser Ser Asp Ile Tyr Glu Leu Met
        35                  40

<210> SEQ ID NO 45
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 45

Thr Arg Glu Gly Ala Asp Gly Ala Ile Cys Gly Tyr Asn Leu Ala Thr
1               5                   10                  15

Leu Asp Met Leu Gly Pro Ser Glu Arg Val Leu Cys Pro Leu Cys Glu
            20                  25                  30

Pro Cys Ser Ser Asp Ile Tyr Glu Leu Met
        35                  40

<210> SEQ ID NO 46
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 46

Ala Arg Glu Gly Ala Asp Gly Ala Ile Cys Gly Tyr Asn Leu Ala Thr
1               5                   10                  15

Leu Val Met Leu Gly Pro Ser Glu Arg Val Phe Cys Pro Leu Cys Gly
            20                  25                  30

Pro Cys Ser Thr Asp Ile Tyr Glu Leu Met
        35                  40

<210> SEQ ID NO 47
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 47

Ala Arg Glu Gly Ala Asp Gly Ala Ile Cys Gly Tyr Asn Leu Ala Ala
1               5                   10                  15

Leu Gly Met Leu Gly Pro Ser Glu Arg Val Phe Cys Pro Leu Cys Gly
            20                  25                  30

Pro Cys Ser Ser Asp Asn Tyr Glu Leu Met
        35                  40

<210> SEQ ID NO 48
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 48

Ala Arg Glu Gly Ala Asp Gly Ala Ile Cys Gly Tyr Asn Leu Ala Thr
1               5                   10                  15

Leu Ala Met Leu Gly Pro Ser Ala Arg Val Phe Cys Pro Leu Cys Gly
            20                  25                  30

Pro Cys Ser Ser Asp Ile Tyr Glu Leu Met
        35                  40

<210> SEQ ID NO 49
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 49

Ala Arg Glu Gly Ala Asp Gly Ala Ile Cys Gly Tyr Asp Leu Ala Met
1               5                   10                  15

Leu Val Met Leu Gly Pro Ser Glu Arg Val Phe Cys Pro Leu Cys Glu
            20                  25                  30

Pro Arg Ser Ser Asp Ile Tyr Glu Leu Met
        35                  40

<210> SEQ ID NO 50
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 50

Ala Arg Glu Gly Ala Asp Gly Ala Ile Cys Gly Tyr Asn Leu Ala Ala
1               5                   10                  15

Ser Val Met Leu Gly Pro Ser Glu Arg Val Phe Cys Pro Leu Cys Glu
            20                  25                  30

```
Pro Arg Ser Pro Asp Ile Tyr Glu Leu Met
         35                  40

<210> SEQ ID NO 51
<211> LENGTH: 42
<212> TYPE: PRT
<213> ORGANISM: Artificial sequence
<220> FEATURE:
<223> OTHER INFORMATION: peptide derived from TRIP alpha

<400> SEQUENCE: 51

Ala Arg Glu Gly Ala Asp Gly Ala Ile Cys Gly Tyr Asn Leu Ala Thr
1               5                   10                  15

Leu Asp Met Leu Gly Pro Ser Glu Arg Val Phe Cys Pro Leu Cys Glu
            20                  25                  30

Pro Cys Ser Ser Asp Ser Tyr Glu Leu Met
         35                  40

<210> SEQ ID NO 52
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 52

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
         35                  40                  45

Pro Ser Glu Arg Val Phe Cys Pro Leu Cys Gly Pro Gly Pro Cys Lys
     50                  55                  60

Met Ile Ala Pro Ile Leu Asp Glu Ile Ala Asp Glu Tyr Gln Gly Lys
65                  70                  75                  80

Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
            100                 105                 110

Glu Val Ala Ser Ala Thr Lys Val Gly Ala Leu Ser Lys Gly Gln Leu
        115                 120                 125

Lys Glu Phe Leu Asp Ala Asn Leu Ala
    130                 135

<210> SEQ ID NO 53
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 53

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Met Ser Val Met Leu Gly
         35                  40                  45
```

Pro Ser Glu Arg Val Phe Cys Pro Leu Cys Glu Pro Gly Pro Cys Lys
    50                  55                  60

Met Ile Ala Pro Ile Leu Asp Glu Ile Ala Asp Glu Tyr Gln Gly Lys
 65                  70                  75                  80

Leu Thr Val Ala Lys Leu Asn Ile Asp Gln Asn Pro Gly Thr Ala Pro
                 85                  90                  95

Lys Tyr Gly Ile Arg Gly Ile Pro Thr Leu Leu Phe Lys Asn Gly
                100                 105                 110

Glu Val Ala Ser Ala Thr Lys Val Gly Ala Leu Ser Lys Gly Gln Leu
                115                 120                 125

Lys Glu Phe Leu Asp Ala Asn Leu Ala
        130                 135

<210> SEQ ID NO 54
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 54

Met Ser Asp Lys Ile Ile His Leu Thr Asp Ser Phe Asp Thr Asp
 1               5                  10                  15

Val Leu Lys Ala Asp Gly Ala Ile Leu Val Asp Phe Trp Ala Glu Trp
                 20                  25                  30

Cys Gly Pro Ile Cys Gly Tyr Asn Leu Ala Met Leu Val Met Leu Gly
             35                  40                  45

Pro Ser Glu Arg Val Phe Cys Pro Leu Cys Glu Pro Gly Pro Cys Lys
    50                  55                  60

Met Ile Ala Pro Ile Leu Asp Glu Ile Ala Asp Glu Tyr Gln Gly Lys
 65                  70                  75                  80

Leu Thr Val Ala Lys Leu Asn Ile Asp Gln Asn Pro Gly Thr Ala Pro
                 85                  90                  95

Lys Tyr Gly Ile Arg Gly Ile Pro Thr Leu Leu Phe Lys Asn Gly
                100                 105                 110

Glu Val Ala Ser Ala Thr Lys Val Gly Ala Leu Ser Lys Gly Gln Leu
                115                 120                 125

Lys Glu Phe Leu Asp Ala Asn Leu Ala
        130                 135

<210> SEQ ID NO 55
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 55

Met Ser Asp Lys Ile Ile His Leu Thr Asp Ser Phe Asp Thr Asp
 1               5                  10                  15

Val Leu Lys Ala Asp Gly Ala Ile Leu Val Asp Phe Trp Ala Glu Trp
                 20                  25                  30

Cys Gly Pro Ile Cys Gly Tyr Asn Leu Ala Thr Ser Val Met Leu Gly
             35                  40                  45

Pro Ser Glu Arg Val Phe Cys Pro Leu Cys Glu Pro Gly Pro Cys Lys
    50                  55                  60

Met Ile Ala Pro Ile Leu Asp Glu Ile Ala Asp Glu Tyr Gln Gly Lys
 65                  70                  75                  80

```
Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
            100                 105                 110

Glu Val Ala Ser Ala Thr Lys Val Gly Ala Leu Ser Lys Gly Gln Leu
        115                 120                 125

Lys Glu Phe Leu Asp Ala Asn Leu Ala
    130                 135

<210> SEQ ID NO 56
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 56

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Met Leu Val Met Leu Gly
        35                  40                  45

Pro Gly Glu Arg Val Phe Cys Pro Leu Cys Pro Gly Pro Cys Lys
    50                  55                  60

Met Ile Ala Pro Ile Leu Asp Glu Ile Ala Asp Glu Tyr Gln Gly Lys
65                  70                  75                  80

Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
            100                 105                 110

Glu Val Ala Ser Ala Thr Lys Val Gly Ala Leu Ser Lys Gly Gln Leu
        115                 120                 125

Lys Glu Phe Leu Asp Ala Asn Leu Ala
    130                 135

<210> SEQ ID NO 57
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 57

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Asp Met Leu Gly
        35                  40                  45

Pro Ser Glu Arg Val Leu Cys Pro Leu Cys Glu Pro Gly Pro Cys Lys
    50                  55                  60

Met Ile Ala Pro Ile Leu Asp Glu Ile Ala Asp Glu Tyr Gln Gly Lys
65                  70                  75                  80

Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
```

```
                    100                 105                 110
Glu Val Ala Ser Ala Thr Lys Val Gly Ala Leu Ser Lys Gly Gln Leu
                115                 120                 125

Lys Glu Phe Leu Asp Ala Asn Leu Ala
            130                 135

<210> SEQ ID NO 58
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 58

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ile Cys Gly Tyr Asn Leu Ala Thr Leu Val Met Leu Gly
            35                  40                  45

Pro Ser Glu Arg Val Phe Cys Pro Leu Cys Gly Pro Gly Pro Cys Lys
50                  55                  60

Met Ile Ala Pro Ile Leu Asp Glu Ile Ala Asp Glu Tyr Gln Gly Lys
65                  70                  75                  80

Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
            100                 105                 110

Glu Val Ala Ser Ala Thr Lys Val Gly Ala Leu Ser Lys Gly Gln Leu
                115                 120                 125

Lys Glu Phe Leu Asp Ala Asn Leu Ala
            130                 135

<210> SEQ ID NO 59
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 59

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ile Cys Gly Tyr Asn Leu Ala Ala Leu Gly Met Leu Gly
            35                  40                  45

Pro Ser Glu Arg Val Phe Cys Pro Leu Cys Gly Pro Gly Pro Cys Lys
50                  55                  60

Met Ile Ala Pro Ile Leu Asp Glu Ile Ala Asp Glu Tyr Gln Gly Lys
65                  70                  75                  80

Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
            100                 105                 110

Glu Val Ala Ser Ala Thr Lys Val Gly Ala Leu Ser Lys Gly Gln Leu
                115                 120                 125
```

Lys Glu Phe Leu Asp Ala Asn Leu Ala
    130                 135

<210> SEQ ID NO 60
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 60

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Ala Met Leu Gly
        35                  40                  45

Pro Ser Ala Arg Val Phe Cys Pro Leu Cys Gly Pro Gly Pro Cys Lys
    50                  55                  60

Met Ile Ala Pro Ile Leu Asp Glu Ile Ala Asp Glu Tyr Gln Gly Lys
65                  70                  75                  80

Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
            100                 105                 110

Glu Val Ala Ser Ala Thr Lys Val Gly Ala Leu Ser Lys Gly Gln Leu
        115                 120                 125

Lys Glu Phe Leu Asp Ala Asn Leu Ala
    130                 135

<210> SEQ ID NO 61
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 61

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asp Leu Ala Met Leu Val Met Leu Gly
        35                  40                  45

Pro Ser Glu Arg Val Phe Cys Pro Leu Cys Glu Pro Gly Pro Cys Lys
    50                  55                  60

Met Ile Ala Pro Ile Leu Asp Glu Ile Ala Asp Glu Tyr Gln Gly Lys
65                  70                  75                  80

Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
            100                 105                 110

Glu Val Ala Ser Ala Thr Lys Val Gly Ala Leu Ser Lys Gly Gln Leu
        115                 120                 125

Lys Glu Phe Leu Asp Ala Asn Leu Ala
    130                 135

<210> SEQ ID NO 62

<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 62

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Ala Ser Val Met Leu Gly
        35                  40                  45

Pro Ser Glu Arg Val Phe Cys Pro Leu Cys Glu Pro Gly Pro Cys Lys
    50                  55                  60

Met Ile Ala Pro Ile Leu Asp Glu Ile Ala Asp Glu Tyr Gln Gly Lys
65                  70                  75                  80

Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
            100                 105                 110

Glu Val Ala Ser Ala Thr Lys Val Gly Ala Leu Ser Lys Gly Gln Leu
        115                 120                 125

Lys Glu Phe Leu Asp Ala Asn Leu Ala
    130                 135

<210> SEQ ID NO 63
<211> LENGTH: 137
<212> TYPE: PRT
<213> ORGANISM: Artificial sequence
<220> FEATURE:
<223> OTHER INFORMATION: peptide derived from TRIP alpha

<400> SEQUENCE: 63

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Asp Met Leu Gly
        35                  40                  45

Pro Ser Glu Arg Val Phe Cys Pro Leu Cys Glu Pro Gly Pro Cys Lys
    50                  55                  60

Met Ile Ala Pro Ile Leu Asp Glu Ile Ala Asp Glu Tyr Gln Gly Lys
65                  70                  75                  80

Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
            100                 105                 110

Glu Val Ala Ser Ala Thr Lys Val Gly Ala Leu Ser Lys Gly Gln Leu
        115                 120                 125

Lys Glu Phe Leu Asp Ala Asn Leu Ala
    130                 135

<210> SEQ ID NO 64
<211> LENGTH: 145
<212> TYPE: PRT
<213> ORGANISM: Artificial sequence
<220> FEATURE:
<223> OTHER INFORMATION: peptide derived from TRIP alpha

<400> SEQUENCE: 64

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ala Arg Glu Gly Ala Asp Gly Ala Ile Cys Gly Tyr Asn
            35                  40                  45

Leu Ala Thr Leu Val Met Leu Gly Pro Ser Glu Arg Val Phe Cys Pro
    50                  55                  60

Leu Cys Gly Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
                100                 105                 110

Thr Leu Leu Leu Phe Lys Asn Gly Glu Val Ala Ser Ala Thr Lys Val
            115                 120                 125

Gly Ala Leu Ser Lys Gly Gln Leu Lys Glu Phe Leu Asp Ala Asn Leu
    130                 135                 140

Ala
145
```

<210> SEQ ID NO 65
<211> LENGTH: 145
<212> TYPE: PRT
<213> ORGANISM: Artificial sequence
<220> FEATURE:
<223> OTHER INFORMATION: peptide derived from TRIP alpha

<400> SEQUENCE: 65

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ala Arg Glu Gly Ala Asp Gly Ala Ile Cys Gly Tyr Asn
            35                  40                  45

Leu Ala Met Ser Val Met Leu Gly Pro Ser Glu Arg Val Phe Cys Pro
    50                  55                  60

Leu Cys Glu Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
                100                 105                 110

Thr Leu Leu Leu Phe Lys Asn Gly Glu Val Ala Ser Ala Thr Lys Val
            115                 120                 125

Gly Ala Leu Ser Lys Gly Gln Leu Lys Glu Phe Leu Asp Ala Asn Leu
    130                 135                 140

Ala
145
```

<210> SEQ ID NO 66
<211> LENGTH: 145
<212> TYPE: PRT
<213> ORGANISM: Artificial sequence
<220> FEATURE:

<223> OTHER INFORMATION: peptide derived from TRIP alpha

<400> SEQUENCE: 66

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ala Arg Glu Gly Ala Asp Gly Ala Ile Cys Gly Tyr Asn
            35                  40                  45

Leu Ala Met Leu Val Met Leu Gly Pro Ser Glu Arg Val Phe Cys Pro
        50                  55                  60

Leu Cys Glu Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
            100                 105                 110

Thr Leu Leu Leu Phe Lys Asn Gly Glu Val Ala Ser Ala Thr Lys Val
        115                 120                 125

Gly Ala Leu Ser Lys Gly Gln Leu Lys Glu Phe Leu Asp Ala Asn Leu
    130                 135                 140

Ala
145

<210> SEQ ID NO 67
<211> LENGTH: 145
<212> TYPE: PRT
<213> ORGANISM: Artificial sequence
<220> FEATURE:
<223> OTHER INFORMATION: peptide derived from TRIP alpha

<400> SEQUENCE: 67

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ala Arg Glu Gly Ala Asp Gly Ala Ile Cys Gly Tyr Asn
            35                  40                  45

Leu Ala Thr Ser Val Met Leu Gly Pro Ser Glu Arg Val Phe Cys Pro
        50                  55                  60

Leu Cys Glu Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
            100                 105                 110

Thr Leu Leu Leu Phe Lys Asn Gly Glu Val Ala Ser Ala Thr Lys Val
        115                 120                 125

Gly Ala Leu Ser Lys Gly Gln Leu Lys Glu Phe Leu Asp Ala Asn Leu
    130                 135                 140

Ala
145

<210> SEQ ID NO 68
<211> LENGTH: 145
<212> TYPE: PRT
<213> ORGANISM: Artificial sequence
<220> FEATURE:
<223> OTHER INFORMATION: peptide derived from TRIP alpha

<400> SEQUENCE: 68

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
        35                  40                  45

Leu Ala Met Leu Val Met Leu Gly Pro Gly Glu Arg Val Phe Cys Pro
    50                  55                  60

Leu Cys Glu Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
            100                 105                 110

Thr Leu Leu Leu Phe Lys Asn Gly Glu Val Ala Ser Ala Thr Lys Val
        115                 120                 125

Gly Ala Leu Ser Lys Gly Gln Leu Lys Glu Phe Leu Asp Ala Asn Leu
    130                 135                 140

Ala
145
```

<210> SEQ ID NO 69
<211> LENGTH: 145
<212> TYPE: PRT
<213> ORGANISM: Artificial sequence
<220> FEATURE:
<223> OTHER INFORMATION: peptide derived from TRIP alpha

<400> SEQUENCE: 69

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Thr Arg Glu Gly Ala Asp Gly Ala Ile Cys Gly Tyr Asn
        35                  40                  45

Leu Ala Thr Leu Asp Met Leu Gly Pro Ser Glu Arg Val Leu Cys Pro
    50                  55                  60

Leu Cys Glu Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
            100                 105                 110

Thr Leu Leu Leu Phe Lys Asn Gly Glu Val Ala Ser Ala Thr Lys Val
        115                 120                 125

Gly Ala Leu Ser Lys Gly Gln Leu Lys Glu Phe Leu Asp Ala Asn Leu
    130                 135                 140

Ala
145
```

<210> SEQ ID NO 70
<211> LENGTH: 145
<212> TYPE: PRT

<213> ORGANISM: Artificial sequence
<220> FEATURE:
<223> OTHER INFORMATION: peptide derived from TRIP alpha

<400> SEQUENCE: 70

```
Met Ser Asp Lys Ile Ile His Leu Thr Asp Asp Ser Phe Asp Thr Asp
1               5                   10                  15
Val Leu Lys Ala Asp Gly Ala Ile Leu Val Asp Phe Trp Ala Glu Trp
                20                  25                  30
Cys Gly Pro Ala Arg Glu Gly Ala Asp Gly Ala Ile Cys Gly Tyr Asn
                35                  40                  45
Leu Ala Thr Leu Val Met Leu Gly Pro Ser Glu Arg Val Phe Cys Pro
        50                  55                  60
Leu Cys Gly Pro Gly Pro Cys Lys Met Ile Ala Pro Ile Leu Asp Glu
65                  70                  75                  80
Ile Ala Asp Glu Tyr Gln Gly Lys Leu Thr Val Ala Lys Leu Asn Ile
                85                  90                  95
Asp Gln Asn Pro Gly Thr Ala Pro Lys Tyr Gly Ile Arg Gly Ile Pro
                100                 105                 110
Thr Leu Leu Leu Phe Lys Asn Gly Glu Val Ala Ser Ala Thr Lys Val
                115                 120                 125
Gly Ala Leu Ser Lys Gly Gln Leu Lys Glu Phe Leu Asp Ala Asn Leu
        130                 135                 140
Ala
145
```

<210> SEQ ID NO 71
<211> LENGTH: 145
<212> TYPE: PRT
<213> ORGANISM: Artificial sequence
<220> FEATURE:
<223> OTHER INFORMATION: peptide derived from TRIP alpha

<400> SEQUENCE: 71

```
Met Ser Asp Lys Ile Ile His Leu Thr Asp Asp Ser Phe Asp Thr Asp
1               5                   10                  15
Val Leu Lys Ala Asp Gly Ala Ile Leu Val Asp Phe Trp Ala Glu Trp
                20                  25                  30
Cys Gly Pro Ala Arg Glu Gly Ala Asp Gly Ala Ile Cys Gly Tyr Asn
                35                  40                  45
Leu Ala Ala Leu Gly Met Leu Gly Pro Ser Glu Arg Val Phe Cys Pro
        50                  55                  60
Leu Cys Gly Pro Gly Pro Cys Lys Met Ile Ala Pro Ile Leu Asp Glu
65                  70                  75                  80
Ile Ala Asp Glu Tyr Gln Gly Lys Leu Thr Val Ala Lys Leu Asn Ile
                85                  90                  95
Asp Gln Asn Pro Gly Thr Ala Pro Lys Tyr Gly Ile Arg Gly Ile Pro
                100                 105                 110
Thr Leu Leu Leu Phe Lys Asn Gly Glu Val Ala Ser Ala Thr Lys Val
                115                 120                 125
Gly Ala Leu Ser Lys Gly Gln Leu Lys Glu Phe Leu Asp Ala Asn Leu
        130                 135                 140
Ala
145
```

<210> SEQ ID NO 72
<211> LENGTH: 145

```
<212> TYPE: PRT
<213> ORGANISM: Artificial sequence
<220> FEATURE:
<223> OTHER INFORMATION: peptide derived from TRIP alpha

<400> SEQUENCE: 72

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
        35                  40                  45

Leu Ala Thr Leu Ala Met Leu Gly Pro Ser Ala Arg Val Phe Cys Pro
    50                  55                  60

Leu Cys Gly Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
            100                 105                 110

Thr Leu Leu Leu Phe Lys Asn Gly Glu Val Ala Ser Ala Thr Lys Val
        115                 120                 125

Gly Ala Leu Ser Lys Gly Gln Leu Lys Glu Phe Leu Asp Ala Asn Leu
    130                 135                 140

Ala
145

<210> SEQ ID NO 73
<211> LENGTH: 145
<212> TYPE: PRT
<213> ORGANISM: Artificial sequence
<220> FEATURE:
<223> OTHER INFORMATION: peptide derived from TRIP alpha

<400> SEQUENCE: 73

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asp
        35                  40                  45

Leu Ala Met Leu Val Met Leu Gly Pro Ser Glu Arg Val Phe Cys Pro
    50                  55                  60

Leu Cys Glu Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
            100                 105                 110

Thr Leu Leu Leu Phe Lys Asn Gly Glu Val Ala Ser Ala Thr Lys Val
        115                 120                 125

Gly Ala Leu Ser Lys Gly Gln Leu Lys Glu Phe Leu Asp Ala Asn Leu
    130                 135                 140

Ala
145

<210> SEQ ID NO 74
```

```
<211> LENGTH: 145
<212> TYPE: PRT
<213> ORGANISM: Artificial sequence
<220> FEATURE:
<223> OTHER INFORMATION: peptide derived from TRIP alpha

<400> SEQUENCE: 74
```

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
        35                  40                  45

Leu Ala Ala Ser Val Met Leu Gly Pro Ser Glu Arg Val Phe Cys Pro
    50                  55                  60

Leu Cys Glu Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
            100                 105                 110

Thr Leu Leu Leu Phe Lys Asn Gly Glu Val Ala Ser Ala Thr Lys Val
        115                 120                 125

Gly Ala Leu Ser Lys Gly Gln Leu Lys Glu Phe Leu Asp Ala Asn Leu
    130                 135                 140

Ala
145

```
<210> SEQ ID NO 75
<211> LENGTH: 145
<212> TYPE: PRT
<213> ORGANISM: Artificial sequence
<220> FEATURE:
<223> OTHER INFORMATION: peptide derived from TRIP alpha

<400> SEQUENCE: 75
```

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
        35                  40                  45

Leu Ala Thr Leu Asp Met Leu Gly Pro Ser Glu Arg Val Phe Cys Pro
    50                  55                  60

Leu Cys Glu Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
            100                 105                 110

Thr Leu Leu Leu Phe Lys Asn Gly Glu Val Ala Ser Ala Thr Lys Val
        115                 120                 125

Gly Ala Leu Ser Lys Gly Gln Leu Lys Glu Phe Leu Asp Ala Asn Leu
    130                 135                 140

Ala
145

```
<210> SEQ ID NO 76
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 76

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
        35                  40                  45

Pro Ser Glu Arg Val Phe Cys Pro Leu Cys Gly Pro Cys Ser Ser Asp
    50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
            100                 105                 110

Pro Thr Leu Leu Leu Phe Lys Asn Gly Glu Val Ala Ser Ala Thr Lys
        115                 120                 125

Val Gly Ala Leu Ser Lys Gly Gln Leu Lys Glu Phe Leu Asp Ala Asn
    130                 135                 140

Leu Ala
145

<210> SEQ ID NO 77
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 77

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Met Ser Val Met Leu Gly
        35                  40                  45

Pro Ser Glu Arg Val Phe Cys Pro Leu Cys Glu Pro Cys Ser Ser Asp
    50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
            100                 105                 110

Pro Thr Leu Leu Leu Phe Lys Asn Gly Glu Val Ala Ser Ala Thr Lys
        115                 120                 125

Val Gly Ala Leu Ser Lys Gly Gln Leu Lys Glu Phe Leu Asp Ala Asn
    130                 135                 140

Leu Ala
145
```

```
<210> SEQ ID NO 78
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 78

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ile Cys Gly Tyr Asn Leu Ala Met Leu Val Met Leu Gly
            35                  40                  45

Pro Ser Glu Arg Val Phe Cys Pro Leu Cys Glu Pro Cys Ser Ser Asp
        50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
            100                 105                 110

Pro Thr Leu Leu Leu Phe Lys Asn Gly Glu Val Ala Ser Ala Thr Lys
        115                 120                 125

Val Gly Ala Leu Ser Lys Gly Gln Leu Lys Glu Phe Leu Asp Ala Asn
    130                 135                 140

Leu Ala
145

<210> SEQ ID NO 79
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 79

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ile Cys Gly Tyr Asn Leu Ala Thr Ser Val Met Leu Gly
            35                  40                  45

Pro Ser Glu Arg Val Phe Cys Pro Leu Cys Glu Pro Cys Ser Ser Asp
        50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
            100                 105                 110

Pro Thr Leu Leu Leu Phe Lys Asn Gly Glu Val Ala Ser Ala Thr Lys
        115                 120                 125

Val Gly Ala Leu Ser Lys Gly Gln Leu Lys Glu Phe Leu Asp Ala Asn
    130                 135                 140

Leu Ala
145
```

```
<210> SEQ ID NO 80
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 80

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Met Leu Val Met Leu Gly
        35                  40                  45

Pro Gly Glu Arg Val Phe Cys Pro Leu Cys Glu Pro Cys Ser Ser Asp
    50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
            100                 105                 110

Pro Thr Leu Leu Leu Phe Lys Asn Gly Glu Val Ala Ser Ala Thr Lys
        115                 120                 125

Val Gly Ala Leu Ser Lys Gly Gln Leu Lys Glu Phe Leu Asp Ala Asn
    130                 135                 140

Leu Ala
145

<210> SEQ ID NO 81
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 81

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Asp Met Leu Gly
        35                  40                  45

Pro Ser Glu Arg Val Leu Cys Pro Leu Cys Glu Pro Cys Ser Ser Asp
    50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
            100                 105                 110

Pro Thr Leu Leu Leu Phe Lys Asn Gly Glu Val Ala Ser Ala Thr Lys
        115                 120                 125

Val Gly Ala Leu Ser Lys Gly Gln Leu Lys Glu Phe Leu Asp Ala Asn
    130                 135                 140

Leu Ala
```

```
<210> SEQ ID NO 82
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 82

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
        35                  40                  45

Pro Ser Glu Arg Val Phe Cys Pro Leu Cys Gly Pro Cys Ser Thr Asp
    50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
            100                 105                 110

Pro Thr Leu Leu Leu Phe Lys Asn Gly Glu Val Ala Ser Ala Thr Lys
        115                 120                 125

Val Gly Ala Leu Ser Lys Gly Gln Leu Lys Glu Phe Leu Asp Ala Asn
    130                 135                 140

Leu Ala
145

<210> SEQ ID NO 83
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 83

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Ala Leu Gly Met Leu Gly
        35                  40                  45

Pro Ser Glu Arg Val Phe Cys Pro Leu Cys Gly Pro Cys Ser Ser Asp
    50                  55                  60

Asn Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
            100                 105                 110

Pro Thr Leu Leu Leu Phe Lys Asn Gly Glu Val Ala Ser Ala Thr Lys
        115                 120                 125

Val Gly Ala Leu Ser Lys Gly Gln Leu Lys Glu Phe Leu Asp Ala Asn
    130                 135                 140
```

Leu Ala
145

<210> SEQ ID NO 84
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 84

Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ile Cys Gly Tyr Asn Leu Ala Thr Leu Ala Met Leu Gly
            35                  40                  45

Pro Ser Ala Arg Val Phe Cys Pro Leu Cys Gly Pro Cys Ser Ser Asp
        50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
            100                 105                 110

Pro Thr Leu Leu Leu Phe Lys Asn Gly Glu Val Ala Ser Ala Thr Lys
        115                 120                 125

Val Gly Ala Leu Ser Lys Gly Gln Leu Lys Glu Phe Leu Asp Ala Asn
    130                 135                 140

Leu Ala
145

<210> SEQ ID NO 85
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 85

Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ile Cys Gly Tyr Asp Leu Ala Met Leu Val Met Leu Gly
            35                  40                  45

Pro Ser Glu Arg Val Phe Cys Pro Leu Cys Glu Pro Arg Ser Ser Asp
        50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
            100                 105                 110

Pro Thr Leu Leu Leu Phe Lys Asn Gly Glu Val Ala Ser Ala Thr Lys
        115                 120                 125

Val Gly Ala Leu Ser Lys Gly Gln Leu Lys Glu Phe Leu Asp Ala Asn
    130                 135                 140

Leu Ala
145

<210> SEQ ID NO 86
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 86

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ile Cys Gly Tyr Asn Leu Ala Ala Ser Val Met Leu Gly
                35                  40                  45

Pro Ser Glu Arg Val Phe Cys Pro Leu Cys Glu Pro Arg Ser Pro Asp
        50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
                100                 105                 110

Pro Thr Leu Leu Leu Phe Lys Asn Gly Glu Val Ala Ser Ala Thr Lys
            115                 120                 125

Val Gly Ala Leu Ser Lys Gly Gln Leu Lys Glu Phe Leu Asp Ala Asn
    130                 135                 140

Leu Ala
145

<210> SEQ ID NO 87
<211> LENGTH: 146
<212> TYPE: PRT
<213> ORGANISM: Artificial sequence
<220> FEATURE:
<223> OTHER INFORMATION: peptide derived from TRIP alpha

<400> SEQUENCE: 87

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ile Cys Gly Tyr Asn Leu Ala Thr Leu Asp Met Leu Gly
                35                  40                  45

Pro Ser Glu Arg Val Phe Cys Pro Leu Cys Glu Pro Cys Ser Ser Asp
        50                  55                  60

Ser Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
                100                 105                 110

Pro Thr Leu Leu Leu Phe Lys Asn Gly Glu Val Ala Ser Ala Thr Lys
            115                 120                 125

Val Gly Ala Leu Ser Lys Gly Gln Leu Lys Glu Phe Leu Asp Ala Asn

```
                130               135               140
Leu Ala
145

<210> SEQ ID NO 88
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 88

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ala Arg Glu Gly Ala Asp Gly Ala Ile Cys Gly Tyr Asn
            35                  40                  45

Leu Ala Thr Leu Val Met Leu Gly Pro Ser Glu Arg Val Phe Cys Pro
    50                  55                  60

Leu Cys Gly Pro Cys Ser Ser Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Leu Phe Lys Asn
        115                 120                 125

Gly Glu Val Ala Ser Ala Thr Lys Val Gly Ala Leu Ser Lys Gly Gln
    130                 135                 140

Leu Lys Glu Phe Leu Asp Ala Asn Leu Ala
145                 150

<210> SEQ ID NO 89
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 89

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ala Arg Glu Gly Ala Asp Gly Ala Ile Cys Gly Tyr Asn
            35                  40                  45

Leu Ala Met Ser Val Met Leu Gly Pro Ser Glu Arg Val Phe Cys Pro
    50                  55                  60

Leu Cys Glu Pro Cys Ser Ser Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Leu Phe Lys Asn
        115                 120                 125
```

```
Gly Glu Val Ala Ser Ala Thr Lys Val Gly Ala Leu Ser Lys Gly Gln
            130                 135                 140

Leu Lys Glu Phe Leu Asp Ala Asn Leu Ala
145                 150
```

<210> SEQ ID NO 90
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 90

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
        35                  40                  45

Leu Ala Met Leu Val Met Leu Gly Pro Ser Glu Arg Val Phe Cys Pro
    50                  55                  60

Leu Cys Glu Pro Cys Ser Ser Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Leu Phe Lys Asn
        115                 120                 125

Gly Glu Val Ala Ser Ala Thr Lys Val Gly Ala Leu Ser Lys Gly Gln
    130                 135                 140

Leu Lys Glu Phe Leu Asp Ala Asn Leu Ala
145                 150
```

<210> SEQ ID NO 91
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 91

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
        35                  40                  45

Leu Ala Thr Ser Val Met Leu Gly Pro Ser Glu Arg Val Phe Cys Pro
    50                  55                  60

Leu Cys Glu Pro Cys Ser Ser Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Leu Phe Lys Asn
        115                 120                 125
```

Gly Glu Val Ala Ser Ala Thr Lys Val Gly Ala Leu Ser Lys Gly Gln
            130                 135                 140

Leu Lys Glu Phe Leu Asp Ala Asn Leu Ala
145                 150

<210> SEQ ID NO 92
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 92

Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
            35                  40                  45

Leu Ala Met Leu Val Met Leu Gly Pro Gly Glu Arg Val Phe Cys Pro
50                  55                  60

Leu Cys Glu Pro Cys Ser Ser Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Leu Phe Lys Asn
            115                 120                 125

Gly Glu Val Ala Ser Ala Thr Lys Val Gly Ala Leu Ser Lys Gly Gln
            130                 135                 140

Leu Lys Glu Phe Leu Asp Ala Asn Leu Ala
145                 150

<210> SEQ ID NO 93
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 93

Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Thr Arg Glu Gly Ala Asp Gly Ala Ile Cys Gly Tyr Asn
            35                  40                  45

Leu Ala Thr Leu Asp Met Leu Gly Pro Ser Glu Arg Val Leu Cys Pro
50                  55                  60

Leu Cys Glu Pro Cys Ser Ser Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Leu Phe Lys Asn 115                 120                 125

Gly Glu Val Ala Ser Ala Thr Lys Val Gly Ala Leu Ser Lys Gly Gln
            130                 135                 140

Leu Lys Glu Phe Leu Asp Ala Asn Leu Ala
145                 150

<210> SEQ ID NO 94
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 94

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ala Arg Glu Gly Ala Asp Gly Ala Ile Cys Gly Tyr Asn
            35                  40                  45

Leu Ala Thr Leu Val Met Leu Gly Pro Ser Glu Arg Val Phe Cys Pro
        50                  55                  60

Leu Cys Gly Pro Cys Ser Thr Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Leu Phe Lys Asn
        115                 120                 125

Gly Glu Val Ala Ser Ala Thr Lys Val Gly Ala Leu Ser Lys Gly Gln
    130                 135                 140

Leu Lys Glu Phe Leu Asp Ala Asn Leu Ala
145                 150

<210> SEQ ID NO 95
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 95

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ala Arg Glu Gly Ala Asp Gly Ala Ile Cys Gly Tyr Asn
            35                  40                  45

Leu Ala Ala Leu Gly Met Leu Gly Pro Ser Glu Arg Val Phe Cys Pro
        50                  55                  60

Leu Cys Gly Pro Cys Ser Ser Asp Asn Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Phe Lys Asn
            115                 120                 125

Gly Glu Val Ala Ser Ala Thr Lys Val Gly Ala Leu Ser Lys Gly Gln
        130                 135                 140

Leu Lys Glu Phe Leu Asp Ala Asn Leu Ala
145                 150

<210> SEQ ID NO 96
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 96

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
        35                  40                  45

Leu Ala Thr Leu Ala Met Leu Gly Pro Ser Ala Arg Val Phe Cys Pro
    50                  55                  60

Leu Cys Gly Pro Cys Ser Ser Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Phe Lys Asn
        115                 120                 125

Gly Glu Val Ala Ser Ala Thr Lys Val Gly Ala Leu Ser Lys Gly Gln
    130                 135                 140

Leu Lys Glu Phe Leu Asp Ala Asn Leu Ala
145                 150

<210> SEQ ID NO 97
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 97

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asp
        35                  40                  45

Leu Ala Met Leu Val Met Leu Gly Pro Ser Glu Arg Val Phe Cys Pro
    50                  55                  60

Leu Cys Glu Pro Arg Ser Ser Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Phe Lys Asn
            115                 120                 125

Gly Glu Val Ala Ser Ala Thr Lys Val Gly Ala Leu Ser Lys Gly Gln
    130                 135                 140

Leu Lys Glu Phe Leu Asp Ala Asn Leu Ala
145                 150

<210> SEQ ID NO 98
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 98

Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
        35                  40                  45

Leu Ala Ala Ser Val Met Leu Gly Pro Ser Glu Arg Val Phe Cys Pro
    50                  55                  60

Leu Cys Glu Pro Arg Ser Pro Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Phe Lys Asn
        115                 120                 125

Gly Glu Val Ala Ser Ala Thr Lys Val Gly Ala Leu Ser Lys Gly Gln
    130                 135                 140

Leu Lys Glu Phe Leu Asp Ala Asn Leu Ala
145                 150

<210> SEQ ID NO 99
<211> LENGTH: 154
<212> TYPE: PRT
<213> ORGANISM: Artificial sequence
<220> FEATURE:
<223> OTHER INFORMATION: peptide derived from TRIP alpha

<400> SEQUENCE: 99

Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
        35                  40                  45

Leu Ala Thr Leu Asp Met Leu Gly Pro Ser Glu Arg Val Phe Cys Pro
    50                  55                  60

Leu Cys Glu Pro Cys Ser Ser Asp Ser Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala

```
                    100                 105                 110
Pro Lys Tyr Gly Ile Arg Gly Ile Pro Thr Leu Leu Phe Lys Asn
        115                 120                 125

Gly Glu Val Ala Ser Ala Thr Lys Val Gly Ala Leu Ser Lys Gly Gln
    130                 135                 140

Leu Lys Glu Phe Leu Asp Ala Asn Leu Ala
145                 150
```

```
<210> SEQ ID NO 100
<211> LENGTH: 75
<212> TYPE: DNA
<213> ORGANISM: Artificial sequence
<220> FEATURE:
<223> OTHER INFORMATION: derived from TRIP alpha
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t

<400> SEQUENCE: 100
atttgtggtt atnnkttggc tnnknnknnk atgctgggtc cgnnknnkcg ggtgnnktgt    60
ccgctttgtn nkcct                                                    75

<210> SEQ ID NO 101
<211> LENGTH: 75
<212> TYPE: DNA
<213> ORGANISM: Artificial sequence
<220> FEATURE:
<223> OTHER INFORMATION: derived from TRIP alpha

<400> SEQUENCE: 101
atttgtggtt ataatttggc tacgttggtt atgctgggtc cgagtgagcg ggtgttttgt    60
ccgctttgtg ggcct                                                    75

<210> SEQ ID NO 102
<211> LENGTH: 75
<212> TYPE: DNA
<213> ORGANISM: Artificial sequence
<220> FEATURE:
<223> OTHER INFORMATION: derived from TRIP alpha
```

```
<400> SEQUENCE: 102
atttgtggtt ataatttggc tatgtcggtt atgctgggtc cgagtgagcg ggtgttttgt      60
ccgctttgtg agcct                                                      75

<210> SEQ ID NO 103
<211> LENGTH: 75
<212> TYPE: DNA
<213> ORGANISM: Artificial sequence
<220> FEATURE:
<223> OTHER INFORMATION: derived from TRIP alpha

<400> SEQUENCE: 103
atttgtggtt ataatttggc tatgttggtt atgctgggtc cgagtgagcg ggtgttttgt      60
ccgctttgtg agcct                                                      75

<210> SEQ ID NO 104
<211> LENGTH: 75
<212> TYPE: DNA
<213> ORGANISM: Artificial sequence
<220> FEATURE:
<223> OTHER INFORMATION: derived from TRIP alpha

<400> SEQUENCE: 104
atttgtggtt ataatttggc tacgtcggtt atgctgggtc cgagtgagcg ggtgttttgt      60
ccgctttgtg agcct                                                      75

<210> SEQ ID NO 105
<211> LENGTH: 75
<212> TYPE: DNA
<213> ORGANISM: Artificial sequence
<220> FEATURE:
<223> OTHER INFORMATION: derived from TRIP alpha

<400> SEQUENCE: 105
atttgtggtt ataatttggc tatgttggtt atgctgggtc cgggtgagcg ggtgttttgt      60
ccgctttgtg agcct                                                      75

<210> SEQ ID NO 106
<211> LENGTH: 75
<212> TYPE: DNA
<213> ORGANISM: Artificial sequence
<220> FEATURE:
<223> OTHER INFORMATION: derived from TRIP alpha

<400> SEQUENCE: 106
atttgtggtt ataatttggc tacgttggat atgctgggtc cgagtgagcg ggtgctttgt      60
ccgctttgtg agcct                                                      75

<210> SEQ ID NO 107
<211> LENGTH: 75
<212> TYPE: DNA
<213> ORGANISM: Artificial sequence
<220> FEATURE:
<223> OTHER INFORMATION: derived from TRIP alpha

<400> SEQUENCE: 107
atttgtggtt ataatttggc tacgttggtt atgctgggtc cgagtgagcg ggtgttttgt      60
ccgctttgtg ggcct                                                      75

<210> SEQ ID NO 108
<211> LENGTH: 75
```

<212> TYPE: DNA
<213> ORGANISM: Artificial sequence
<220> FEATURE:
<223> OTHER INFORMATION: derived from TRIP alpha

<400> SEQUENCE: 108
atttgtggtt ataatttggc tgcgttgggt atgctgggtc cgagtgagcg ggtgttttgt    60
ccgctttgtg ggcct                                                     75

<210> SEQ ID NO 109
<211> LENGTH: 75
<212> TYPE: DNA
<213> ORGANISM: Artificial sequence
<220> FEATURE:
<223> OTHER INFORMATION: derived from TRIP alpha

<400> SEQUENCE: 109
atttgtggtt ataatttggc tacgttggct atgctgggtc cgagtgcgcg ggtgttttgt    60
ccgctttgtg ggcct                                                     75

<210> SEQ ID NO 110
<211> LENGTH: 75
<212> TYPE: DNA
<213> ORGANISM: Artificial sequence
<220> FEATURE:
<223> OTHER INFORMATION: derived from TRIP alpha

<400> SEQUENCE: 110
atttgtggtt atgatttggc tatgttggtt atgctgggtc cgagtgagcg ggtgttttgt    60
ccgctttgtg agcct                                                     75

<210> SEQ ID NO 111
<211> LENGTH: 75
<212> TYPE: DNA
<213> ORGANISM: Artificial sequence
<220> FEATURE:
<223> OTHER INFORMATION: derived from TRIP alpha

<400> SEQUENCE: 111
atttgtggtt ataatttggc tgcgtcggtt atgctgggtc cgagtgagcg ggtgttttgt    60
ccgctttgtg agcct                                                     75

<210> SEQ ID NO 112
<211> LENGTH: 75
<212> TYPE: DNA
<213> ORGANISM: Artificial sequence
<220> FEATURE:
<223> OTHER INFORMATION: derived from TRIP alpha

<400> SEQUENCE: 112
atttgtggtt ataatttggc tacgttggat atgctgggtc cgagtgagcg ggtgttttgt    60
ccgctttgtg agcct                                                     75

<210> SEQ ID NO 113
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 113
gcgagggagg gggctgatgg tgcgatttgt ggttataatt tggctacgtt ggttatgctg    60

```
ggtccgagtg agcgggtgtt ttgtccgctt tgtgggcct                                99
```

<210> SEQ ID NO 114
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 114

```
gcgagggagg gggctgatgg tgcgatttgt ggttataatt tggctatgtc ggttatgctg         60
ggtccgagtg agcgggtgtt ttgtccgctt tgtgagcct                                99
```

<210> SEQ ID NO 115
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 115

```
gcgagggagg gggctgatgg tgcgatttgt ggttataatt tggctatgtt ggttatgctg         60
ggtccgagtg agcgggtgtt ttgtccgctt tgtgagcct                                99
```

<210> SEQ ID NO 116
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 116

```
gcgagggagg gggctgatgg tgcgatttgt ggttataatt tggctacgtc ggttatgctg         60
ggtccgagtg agcgggtgtt ttgtccgctt tgtgagcct                                99
```

<210> SEQ ID NO 117
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 117

```
gcgagggagg gggctgatgg tgcgatttgt ggttataatt tggctatgtt ggttatgctg         60
ggtccgggtg agcgggtgtt ttgtccgctt tgtgagcct                                99
```

<210> SEQ ID NO 118
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 118

```
acgagggagg gggctgatgg tgcgatttgt ggttataatt tggctacgtt ggatatgctg         60
ggtccgagtg agcgggtgct ttgtccgctt tgtgagcct                                99
```

<210> SEQ ID NO 119
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 119
gcgagggagg gggctgatgg tgcgatttgt ggttataatt tggctacgtt ggttatgctg    60
ggtccgagtg agcgggtgtt ttgtccgctt tgtgggcct                          99

<210> SEQ ID NO 120
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 120
gcgagggagg gggctgatgg tgcgatttgt ggttataatt tggctgcgtt gggtatgctg    60
ggtccgagtg agcgggtgtt ttgtccgctt tgtgggcct                          99

<210> SEQ ID NO 121
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 121
gcgagggagg gggctgatgg tgcgatttgt ggttataatt tggctacgtt ggctatgctg    60
ggtccgagtg cgcgggtgtt ttgtccgctt tgtgggcct                          99

<210> SEQ ID NO 122
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 122
gcgagggagg gggctgatgg tgcgatttgt ggttatgatt tggctatgtt ggttatgctg    60
ggtccgagtg agcgggtgtt ttgtccgctt tgtgagcct                          99

<210> SEQ ID NO 123
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 123
gcgagggagg gggctgatgg tgcgatttgt ggttataatt tggctgcgtc ggttatgctg    60
ggtccgagtg agcgggtgtt ttgtccgctt tgtgagcct                          99

<210> SEQ ID NO 124
<211> LENGTH: 99
<212> TYPE: DNA
<213> ORGANISM: Artificial sequence
<220> FEATURE:
<223> OTHER INFORMATION: derived from TRIP alpha

<400> SEQUENCE: 124
gcgagggagg gggctgatgg tgcgatttgt ggttataatt tggctacgtt ggatatgctg    60
ggtccgagtg agcgggtgtt ttgtccgctt tgtgagcct                          99

<210> SEQ ID NO 125

```
<211> LENGTH: 102
<212> TYPE: DNA
<213> ORGANISM: Artificial sequence
<220> FEATURE:
<223> OTHER INFORMATION: derived from TRIP alpha

<400> SEQUENCE: 125
atttgtggtt ataatttggc tacgttggtt atgctgggtc cgagtgagcg ggtgttttgt      60
ccgctttgtg ggccttgtag ttctgatatt tatgagttga tg                        102

<210> SEQ ID NO 126
<211> LENGTH: 102
<212> TYPE: DNA
<213> ORGANISM: Artificial sequence
<220> FEATURE:
<223> OTHER INFORMATION: derived from TRIP alpha

<400> SEQUENCE: 126
atttgtggtt ataatttggc tatgtcggtt atgctgggtc cgagtgagcg ggtgttttgt      60
ccgctttgtg agccttgtag ttctgatatt tatgagttga tg                        102

<210> SEQ ID NO 127
<211> LENGTH: 102
<212> TYPE: DNA
<213> ORGANISM: Artificial sequence
<220> FEATURE:
<223> OTHER INFORMATION: from TRIP alpha

<400> SEQUENCE: 127
atttgtggtt ataatttggc tatgttggtt atgctgggtc cgagtgagcg ggtgttttgt      60
ccgctttgtg agccttgtag ttctgatatt tatgagttga tg                        102

<210> SEQ ID NO 128
<211> LENGTH: 102
<212> TYPE: DNA
<213> ORGANISM: Artificial sequence
<220> FEATURE:
<223> OTHER INFORMATION: derived from TRIP alpha

<400> SEQUENCE: 128
atttgtggtt ataatttggc tacgtcggtt atgctgggtc cgagtgagcg ggtgttttgt      60
ccgctttgtg agccttgtag ttctgatatt tatgagttga tg                        102

<210> SEQ ID NO 129
<211> LENGTH: 102
<212> TYPE: DNA
<213> ORGANISM: Artificial sequence
<220> FEATURE:
<223> OTHER INFORMATION: derived from TRIP alpha

<400> SEQUENCE: 129
atttgtggtt ataatttggc tatgttggtt atgctgggtc cgggtgagcg ggtgttttgt      60
ccgctttgtg agccttgtag ttctgatatt tatgagttga tg                        102

<210> SEQ ID NO 130
<211> LENGTH: 102
<212> TYPE: DNA
<213> ORGANISM: Artificial sequence
<220> FEATURE:
<223> OTHER INFORMATION: derived from TRIP alpha

<400> SEQUENCE: 130
atttgtggtt ataatttggc tacgttggat atgctgggtc cgagtgagcg ggtgctttgt      60
```

<210> SEQ ID NO 131
<211> LENGTH: 102
<212> TYPE: DNA
<213> ORGANISM: Artificial sequence
<220> FEATURE:
<223> OTHER INFORMATION: derived from TRIP alpha

<400> SEQUENCE: 131
atttgtggtt ataatttggc tacgttggtt atgctgggtc cgagtgagcg ggtgttttgt      60
ccgctttgtg ggccttgtag tactgatatt tatgagttga tg                         102

<210> SEQ ID NO 132
<211> LENGTH: 102
<212> TYPE: DNA
<213> ORGANISM: Artificial sequence
<220> FEATURE:
<223> OTHER INFORMATION: derived from TRIP alpha

<400> SEQUENCE: 132
atttgtggtt ataatttggc tgcgttgggt atgctgggtc cgagtgagcg ggtgttttgt      60
ccgctttgtg ggccttgtag ttctgataat tatgagttga tg                         102

<210> SEQ ID NO 133
<211> LENGTH: 102
<212> TYPE: DNA
<213> ORGANISM: Artificial sequence
<220> FEATURE:
<223> OTHER INFORMATION: derived from TRIP alpha

<400> SEQUENCE: 133
atttgtggtt ataatttggc tacgttggct atgctgggtc cgagtgcgcg ggtgttttgt      60
ccgctttgtg ggccttgtag ttctgatatt tatgagttga tg                         102

<210> SEQ ID NO 134
<211> LENGTH: 102
<212> TYPE: DNA
<213> ORGANISM: Artificial sequence
<220> FEATURE:
<223> OTHER INFORMATION: derived from TRIP alpha

<400> SEQUENCE: 134
atttgtggtt atgatttggc tatgttggtt atgctgggtc cgagtgagcg ggtgttttgt      60
ccgctttgtg agcctcgtag ttctgatatt tatgagttga tg                         102

<210> SEQ ID NO 135
<211> LENGTH: 102
<212> TYPE: DNA
<213> ORGANISM: Artificial sequence
<220> FEATURE:
<223> OTHER INFORMATION: derived from TRIP alpha

<400> SEQUENCE: 135
atttgtggtt ataatttggc tgcgtcggtt atgctgggtc cgagtgagcg ggtgttttgt      60
ccgctttgtg agcctcgtag tcctgatatt tatgagttga tg                         102

<210> SEQ ID NO 136
<211> LENGTH: 102
<212> TYPE: DNA
<213> ORGANISM: Artificial sequence
<220> FEATURE:

<223> OTHER INFORMATION: derived from TRIP alpha

<400> SEQUENCE: 136
atttgtggtt ataatttggc tacgttggat atgctgggtc cgagtgagcg ggtgttttgt    60
ccgctttgtg agccttgtag ttctgatagt tatgagttga tg    102

<210> SEQ ID NO 137
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 137
gcgagggagg gggctgatgg tgcgatttgt ggttataatt tggctacgtt ggttatgctg    60
ggtccgagtg agcgggtgtt ttgtccgctt tgtgggcctt gtagttctga tatttatgag    120
ttgatg    126

<210> SEQ ID NO 138
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 138
gcgagggagg gggctgatgg tgcgatttgt ggttataatt tggctatgtc ggttatgctg    60
ggtccgagtg agcgggtgtt ttgtccgctt tgtgagcctt gtagttctga tatttatgag    120
ttgatg    126

<210> SEQ ID NO 139
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 139
gcgagggagg gggctgatgg tgcgatttgt ggttataatt tggctatgtt ggttatgctg    60
ggtccgagtg agcgggtgtt ttgtccgctt tgtgagcctt gtagttctga tatttatgag    120
ttgatg    126

<210> SEQ ID NO 140
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 140
gcgagggagg gggctgatgg tgcgatttgt ggttataatt tggctacgtc ggttatgctg    60
ggtccgagtg agcgggtgtt ttgtccgctt tgtgagcctt gtagttctga tatttatgag    120
ttgatg    126

<210> SEQ ID NO 141
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 141

```
gcgagggagg gggctgatgg tgcgatttgt ggttataatt tggctatgtt ggttatgctg    60
ggtccgggtg agcgggtgtt ttgtccgctt tgtgagcctt gtagttctga tatttatgag   120
ttgatg                                                              126
```

<210> SEQ ID NO 142
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 142

```
acgagggagg gggctgatgg tgcgatttgt ggttataatt tggctacgtt ggatatgctg    60
ggtccgagtg agcgggtgct ttgtccgctt tgtgagcctt gtagttctga tatttatgag   120
ttgatg                                                              126
```

<210> SEQ ID NO 143
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 143

```
gcgagggagg gggctgatgg tgcgatttgt ggttataatt tggctacgtt ggttatgctg    60
ggtccgagtg agcgggtgtt ttgtccgctt tgtgggcctt gtagtactga tatttatgag   120
ttgatg                                                              126
```

<210> SEQ ID NO 144
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 144

```
gcgagggagg gggctgatgg tgcgatttgt ggttataatt tggctgcgtt gggtatgctg    60
ggtccgagtg agcgggtgtt ttgtccgctt tgtgggcctt gtagttctga taattatgag   120
ttgatg                                                              126
```

<210> SEQ ID NO 145
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 145

```
gcgagggagg gggctgatgg tgcgatttgt ggttataatt tggctacgtt ggctatgctg    60
ggtccgagtg cgcgggtgtt ttgtccgctt tgtgggcctt gtagttctga tatttatgag   120
ttgatg                                                              126
```

<210> SEQ ID NO 146
<211> LENGTH: 126
<212> TYPE: DNA
<213> ORGANISM: Artificial sequence
<220> FEATURE:

<223> OTHER INFORMATION: derived from TRIP alpha

<400> SEQUENCE: 146

| gcgagggagg gggctgatgg tgcgatttgt ggttatgatt tggctatgtt ggttatgctg | 60 |
| ggtccgagtg agcgggtgtt ttgtccgctt tgtgagcctc gtagttctga tatttatgag | 120 |
| ttgatg | 126 |

<210> SEQ ID NO 147
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 147

| gcgagggagg gggctgatgg tgcgatttgt ggttataatt tggctgcgtc ggttatgctg | 60 |
| ggtccgagtg agcgggtgtt ttgtccgctt tgtgagcctc gtagtcctga tatttatgag | 120 |
| ttgatg | 126 |

<210> SEQ ID NO 148
<211> LENGTH: 126
<212> TYPE: DNA
<213> ORGANISM: Artificial sequence
<220> FEATURE:
<223> OTHER INFORMATION: derived from TRIP alpha

<400> SEQUENCE: 148

| gcgagggagg gggctgatgg tgcgatttgt ggttataatt tggctacgtt ggatatgctg | 60 |
| ggtccgagtg agcgggtgtt ttgtccgctt tgtgagcctt gtagttctga tagttatgag | 120 |
| ttgatg | 126 |

<210> SEQ ID NO 149
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 149

| atgagcgata aaattattca cctgactgac gacagttttg acacggatgt actcaaagcg | 60 |
| gacggggcga tcctcgtcga tttctgggca gagtggtgcg gtccgatttg tggttataat | 120 |
| ttggctacgt tggttatgct gggtccgagt gagcgggtgt tttgtccgct ttgtgggcct | 180 |
| ggtccgtgca aaatgatcgc cccgattctg gatgaaatcg ctgacgaata tcagggcaaa | 240 |
| ctgaccgttg caaaactgaa catcgatcaa aaccctggca ctgcgccgaa atatggcatc | 300 |
| cgtggtatcc cgactctgct gctgttcaaa aacggtgaag tggcgtcggc aaccaaagtg | 360 |
| ggtgcactgt ctaaaggtca gttgaaagag ttcctcgacg ctaacctggc gtaa | 414 |

<210> SEQ ID NO 150
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 150

| atgagcgata aaattattca cctgactgac gacagttttg acacggatgt actcaaagcg | 60 |
| gacggggcga tcctcgtcga tttctgggca gagtggtgcg gtccgatttg tggttataat | 120 |

```
ttggctatgt cggttatgct gggtccgagt gagcgggtgt tttgtccgct tgtgagcct      180 ggtccgtgca aaatgatcgc cccgattctg gatgaaatcg ctgacgaata tcagggcaaa    240
ctgaccgttg caaaactgaa catcgatcaa aaccctggca ctgcgccgaa atatggcatc    300
cgtggtatcc cgactctgct gctgttcaaa acggtgaag tggcgtcggc aaccaaagtg     360
ggtgcactgt ctaaaggtca gttgaaagag ttcctcgacg ctaacctggc gtaa          414
```

<210> SEQ ID NO 151
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 151

```
atgagcgata aaattattca cctgactgac gacagttttg acacggatgt actcaaagcg    60
gacggggcga tcctcgtcga tttctgggca gagtggtgcg gtccgatttg tggttataat    120
ttggctatgt tggttatgct gggtccgagt gagcgggtgt tttgtccgct tgtgagcct     180 ggtccgtgca aaatgatcgc cccgattctg gatgaaatcg ctgacgaata tcagggcaaa   240
ctgaccgttg caaaactgaa catcgatcaa aaccctggca ctgcgccgaa atatggcatc   300
cgtggtatcc cgactctgct gctgttcaaa acggtgaag tggcgtcggc aaccaaagtg    360
ggtgcactgt ctaaaggtca gttgaaagag ttcctcgacg ctaacctggc gtaa         414
```

<210> SEQ ID NO 152
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 152

```
atgagcgata aaattattca cctgactgac gacagttttg acacggatgt actcaaagcg   60
gacggggcga tcctcgtcga tttctgggca gagtggtgcg gtccgatttg tggttataat   120
ttggctacgt cggttatgct gggtccgagt gagcgggtgt tttgtccgct tgtgagcct    180 ggtccgtgca aaatgatcgc cccgattctg gatgaaatcg ctgacgaata tcagggcaaa  240
ctgaccgttg caaaactgaa catcgatcaa aaccctggca ctgcgccgaa atatggcatc  300
cgtggtatcc cgactctgct gctgttcaaa acggtgaag tggcgtcggc aaccaaagtg   360
ggtgcactgt ctaaaggtca gttgaaagag ttcctcgacg ctaacctggc gtaa        414
```

<210> SEQ ID NO 153
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 153

```
atgagcgata aaattattca cctgactgac gacagttttg acacggatgt actcaaagcg   60
gacggggcga tcctcgtcga tttctgggca gagtggtgcg gtccgatttg tggttataat   120
ttggctatgt tggttatgct gggtccgggt gagcgggtgt tttgtccgct tgtgagcct    180 ggtccgtgca aaatgatcgc cccgattctg gatgaaatcg ctgacgaata tcagggcaaa  240
ctgaccgttg caaaactgaa catcgatcaa aaccctggca ctgcgccgaa atatggcatc  300
```

```
cgtggtatcc cgactctgct gctgttcaaa acggtgaag tggcgtcggc aaccaaagtg    360
ggtgcactgt ctaaaggtca gttgaaagag ttcctcgacg ctaacctggc gtaa         414
```

<210> SEQ ID NO 154
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 154

```
atgagcgata aaattattca cctgactgac gacagttttg acacggatgt actcaaagcg    60
gacggggcga tcctcgtcga tttctgggca gagtggtgcg gtccgatttg tggttataat   120
ttggctacgt tggatatgct gggtccgagt gagcgggtgc tttgtccgct ttgtgagcct   180
ggtccgtgca aaatgatcgc cccgattctg gatgaaatcg ctgacgaata tcagggcaaa   240
ctgaccgttg caaaactgaa catcgatcaa aaccctggca ctgcgccgaa atatggcatc   300
cgtggtatcc cgactctgct gctgttcaaa acggtgaag tggcgtcggc aaccaaagtg    360
ggtgcactgt ctaaaggtca gttgaaagag ttcctcgacg ctaacctggc gtaa         414
```

<210> SEQ ID NO 155
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 155

```
atgagcgata aaattattca cctgactgac gacagttttg acacggatgt actcaaagcg    60
gacggggcga tcctcgtcga tttctgggca gagtggtgcg gtccgatttg tggttataat   120
ttggctacgt tggttatgct gggtccgagt gagcgggtgt tttgtccgct ttgtgggcct   180
ggtccgtgca aaatgatcgc cccgattctg gatgaaatcg ctgacgaata tcagggcaaa   240
ctgaccgttg caaaactgaa catcgatcaa aaccctggca ctgcgccgaa atatggcatc   300
cgtggtatcc cgactctgct gctgttcaaa acggtgaag tggcgtcggc aaccaaagtg    360
ggtgcactgt ctaaaggtca gttgaaagag ttcctcgacg ctaacctggc gtaa         414
```

<210> SEQ ID NO 156
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 156

```
atgagcgata aaattattca cctgactgac gacagttttg acacggatgt actcaaagcg    60
gacggggcga tcctcgtcga tttctgggca gagtggtgcg gtccgatttg tggttataat   120
ttggctgcgt tgggtatgct gggtccgagt gagcgggtgt tttgtccgct ttgtgggcct   180
ggtccgtgca aaatgatcgc cccgattctg gatgaaatcg ctgacgaata tcagggcaaa   240
ctgaccgttg caaaactgaa catcgatcaa aaccctggca ctgcgccgaa atatggcatc   300
cgtggtatcc cgactctgct gctgttcaaa acggtgaag tggcgtcggc aaccaaagtg    360
ggtgcactgt ctaaaggtca gttgaaagag ttcctcgacg ctaacctggc gtaa         414
```

<210> SEQ ID NO 157
<211> LENGTH: 414

```
<212> TYPE: DNA
<213> ORGANISM: Artificial sequence
<220> FEATURE:
<223> OTHER INFORMATION: derived from TRIP alpha

<400> SEQUENCE: 157
atgagcgata aaattattca cctgactgac gacagttttg acacggatgt actcaaagcg      60
gacggggcga tcctcgtcga tttctgggca gagtggtgcg gtccgatttg tggttataat     120
ttggctacgt tggctatgct gggtccgagt gcgcgggtgt tttgtccgct ttgtgggcct     180
ggtccgtgca aaatgatcgc cccgattctg gatgaaatcg ctgacgaata tcagggcaaa     240
ctgaccgttg caaaactgaa catcgatcaa aaccctggca ctgcgccgaa atatggcatc     300
cgtggtatcc cgactctgct gctgttcaaa aacggtgaag tggcgtcggc aaccaaagtg     360
ggtgcactgt ctaaaggtca gttgaaagag ttcctcgacg ctaacctggc gtaa           414

<210> SEQ ID NO 158
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 158
atgagcgata aaattattca cctgactgac gacagttttg acacggatgt actcaaagcg      60
gacggggcga tcctcgtcga tttctgggca gagtggtgcg gtccgatttg tggttatgat     120
ttggctatgt tggttatgct gggtccgagt gagcgggtgt tttgtccgct ttgtgagcct     180
ggtccgtgca aaatgatcgc cccgattctg gatgaaatcg ctgacgaata tcagggcaaa     240
ctgaccgttg caaaactgaa catcgatcaa aaccctggca ctgcgccgaa atatggcatc     300
cgtggtatcc cgactctgct gctgttcaaa aacggtgaag tggcgtcggc aaccaaagtg     360
ggtgcactgt ctaaaggtca gttgaaagag ttcctcgacg ctaacctggc gtaa           414

<210> SEQ ID NO 159
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 159
atgagcgata aaattattca cctgactgac gacagttttg acacggatgt actcaaagcg      60
gacggggcga tcctcgtcga tttctgggca gagtggtgcg gtccgatttg tggttataat     120
ttggctgcgt cggttatgct gggtccgagt gagcgggtgt tttgtccgct ttgtgagcct     180
ggtccgtgca aaatgatcgc cccgattctg gatgaaatcg ctgacgaata tcagggcaaa     240
ctgaccgttg caaaactgaa catcgatcaa aaccctggca ctgcgccgaa atatggcatc     300
cgtggtatcc cgactctgct gctgttcaaa aacggtgaag tggcgtcggc aaccaaagtg     360
ggtgcactgt ctaaaggtca gttgaaagag ttcctcgacg ctaacctggc gtaa           414

<210> SEQ ID NO 160
<211> LENGTH: 414
<212> TYPE: DNA
<213> ORGANISM: Artificial sequence
<220> FEATURE:
<223> OTHER INFORMATION: derived from TRIP alpha

<400> SEQUENCE: 160
```

```
atgagcgata aaattattca cctgactgac gacagttttg acacggatgt actcaaagcg    60
gacggggcga tcctcgtcga tttctgggca gagtggtgcg gtccgatttg tggttataat   120
ttggctacgt tggatatgct gggtccgagt gagcgggtgt tttgtccgct ttgtgagcct   180
ggtccgtgca aaatgatcgc cccgattctg gatgaaatcg ctgacgaata tcagggcaaa   240
ctgaccgttg caaaactgaa catcgatcaa aaccctggca ctgcgccgaa atatggcatc   300
cgtggtatcc cgactctgct gctgttcaaa acggtgaag tggcgtcggc aaccaaagtg    360
ggtgcactgt ctaaaggtca gttgaaagag ttcctcgacg ctaacctggc gtaa          414
```

<210> SEQ ID NO 161
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 161

```
atgagcgata aaattattca cctgactgac gacagttttg acacggatgt actcaaagcg    60
gacggggcga tcctcgtcga tttctgggca gagtggtgcg gtccggcgag ggaggggct   120 gatggtgcga tttgtggtta taatttggct acgttggtta tgctgggtcc gagtgagcgg   180
gtgttttgtc cgctttgtgg gcctggtccg tgcaaaatga tcgccccgat tctggatgaa   240
atcgctgacg aatatcaggg caaactgacc gttgcaaaac tgaacatcga tcaaaaccct   300
ggcactgcgc cgaaatatgg catccgtggt atcccgactc tgctgctgtt caaaaacggt   360
gaagtggcgt cggcaaccaa agtgggtgca ctgtctaaag gtcagttgaa agagttcctc   420
gacgctaacc tggcgtaa                                                  438
```

<210> SEQ ID NO 162
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 162

```
atgagcgata aaattattca cctgactgac gacagttttg acacggatgt actcaaagcg    60
gacggggcga tcctcgtcga tttctgggca gagtggtgcg gtccggcgag ggaggggct   120 gatggtgcga tttgtggtta taatttggct atgtcggtta tgctgggtcc gagtgagcgg   180
gtgttttgtc cgctttgtga gcctggtccg tgcaaaatga tcgccccgat tctggatgaa   240
atcgctgacg aatatcaggg caaactgacc gttgcaaaac tgaacatcga tcaaaaccct   300
ggcactgcgc cgaaatatgg catccgtggt atcccgactc tgctgctgtt caaaaacggt   360
gaagtggcgt cggcaaccaa agtgggtgca ctgtctaaag gtcagttgaa agagttcctc   420
gacgctaacc tggcgtaa                                                  438
```

<210> SEQ ID NO 163
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 163

```
atgagcgata aaattattca cctgactgac gacagttttg acacggatgt actcaaagcg    60
gacggggcga tcctcgtcga tttctgggca gagtggtgcg gtccggcgag ggaggggct   120
```

```
gatggtgcga tttgtggtta taatttggct atgttggtta tgctgggtcc gagtgagcgg    180
gtgttttgtc cgctttgtga gcctggtccg tgcaaaatga tcgccccgat tctggatgaa    240
atcgctgacg aatatcaggg caaactgacc gttgcaaaac tgaacatcga tcaaaaccct    300
ggcactgcgc cgaaatatgg catccgtggt atcccgactc tgctgctgtt caaaaacggt    360
gaagtggcgt cggcaaccaa agtgggtgca ctgtctaaag gtcagttgaa agagttcctc    420
gacgctaacc tggcgtaa                                                  438

<210> SEQ ID NO 164
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 164
atgagcgata aaattattca cctgactgac gacagttttg acacggatgt actcaaagcg    60
gacggggcga tcctcgtcga tttctgggca gagtggtgcg gtccggcgag ggaggggggct   120 gatggtgcga tttgtggtta taatttggct acgtcggtta tgctgggtcc gagtgagcgg    180
gtgttttgtc cgctttgtga gcctggtccg tgcaaaatga tcgccccgat tctggatgaa    240
atcgctgacg aatatcaggg caaactgacc gttgcaaaac tgaacatcga tcaaaaccct    300
ggcactgcgc cgaaatatgg catccgtggt atcccgactc tgctgctgtt caaaaacggt    360
gaagtggcgt cggcaaccaa agtgggtgca ctgtctaaag gtcagttgaa agagttcctc    420
gacgctaacc tggcgtaa                                                  438

<210> SEQ ID NO 165
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 165
atgagcgata aaattattca cctgactgac gacagttttg acacggatgt actcaaagcg    60
gacggggcga tcctcgtcga tttctgggca gagtggtgcg gtccggcgag ggaggggggct   120 gatggtgcga tttgtggtta taatttggct atgttggtta tgctgggtcc gggtgagcgg    180
gtgttttgtc cgctttgtga gcctggtccg tgcaaaatga tcgccccgat tctggatgaa    240
atcgctgacg aatatcaggg caaactgacc gttgcaaaac tgaacatcga tcaaaaccct    300
ggcactgcgc cgaaatatgg catccgtggt atcccgactc tgctgctgtt caaaaacggt    360
gaagtggcgt cggcaaccaa agtgggtgca ctgtctaaag gtcagttgaa agagttcctc    420
gacgctaacc tggcgtaa                                                  438

<210> SEQ ID NO 166
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 166
atgagcgata aaattattca cctgactgac gacagttttg acacggatgt actcaaagcg    60
gacggggcga tcctcgtcga tttctgggca gagtggtgcg gtccgacgag ggaggggggct   120
```

```
gatggtgcga tttgtggtta taatttggct acgttggata tgctgggtcc gagtgagcgg      180
gtgctttgtc cgctttgtga gcctggtccg tgcaaaatga tcgccccgat tctggatgaa      240
atcgctgacg aatatcaggg caaactgacc gttgcaaaac tgaacatcga tcaaaaccct      300
ggcactgcgc cgaaatatgg catccgtggt atcccgactc tgctgctgtt caaaaacggt      360
gaagtggcgt cggcaaccaa agtgggtgca ctgtctaaag gtcagttgaa agagttcctc      420
gacgctaacc tggcgtaa                                                    438

<210> SEQ ID NO 167
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 167
atgagcgata aaattattca cctgactgac gacagttttg acacggatgt actcaaagcg      60
gacggggcga tcctcgtcga tttctgggca gagtggtgcg gtccggcgag ggaggggget      120 gatggtgcga tttgtggtta taatttggct acgttggtta tgctgggtcc gagtgagcgg      180
gtgttttgtc cgctttgtgg gcctggtccg tgcaaaatga tcgccccgat tctggatgaa      240
atcgctgacg aatatcaggg caaactgacc gttgcaaaac tgaacatcga tcaaaaccct      300
ggcactgcgc cgaaatatgg catccgtggt atcccgactc tgctgctgtt caaaaacggt      360
gaagtggcgt cggcaaccaa agtgggtgca ctgtctaaag gtcagttgaa agagttcctc      420
gacgctaacc tggcgtaa                                                    438

<210> SEQ ID NO 168
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 168
atgagcgata aaattattca cctgactgac gacagttttg acacggatgt actcaaagcg      60
gacggggcga tcctcgtcga tttctgggca gagtggtgcg gtccggcgag ggaggggget      120 gatggtgcga tttgtggtta taatttggct gcgttgggta tgctgggtcc gagtgagcgg      180
gtgttttgtc cgctttgtgg gcctggtccg tgcaaaatga tcgccccgat tctggatgaa      240
atcgctgacg aatatcaggg caaactgacc gttgcaaaac tgaacatcga tcaaaaccct      300
ggcactgcgc cgaaatatgg catccgtggt atcccgactc tgctgctgtt caaaaacggt      360
gaagtggcgt cggcaaccaa agtgggtgca ctgtctaaag gtcagttgaa agagttcctc      420
gacgctaacc tggcgtaa                                                    438

<210> SEQ ID NO 169
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 169
atgagcgata aaattattca cctgactgac gacagttttg acacggatgt actcaaagcg      60
gacggggcga tcctcgtcga tttctgggca gagtggtgcg gtccggcgag ggaggggget      120 gatggtgcga tttgtggtta taatttggct acgttggcta tgctgggtcc gagtgcgcgg      180
```

```
gtgttttgtc cgctttgtgg gcctggtccg tgcaaaatga tcgccccgat tctggatgaa    240
atcgctgacg aatatcaggg caaactgacc gttgcaaaac tgaacatcga tcaaaaccct    300
ggcactgcgc cgaaatatgg catccgtggt atcccgactc tgctgctgtt caaaaacggt    360
gaagtggcgt cggcaaccaa agtgggtgca ctgtctaaag gtcagttgaa agagttcctc    420
gacgctaacc tggcgtaa                                                   438
```

<210> SEQ ID NO 170
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 170

```
atgagcgata aaattattca cctgactgac gacagttttg acacggatgt actcaaagcg    60
gacggggcga tcctcgtcga tttctgggca gagtggtgcg gtccggcgag ggaggggggct   120 gatggtgcga tttgtggtta tgatttggct atgttggtta tgctgggtcc gagtgagcgg    180
gtgttttgtc cgctttgtga gcctggtccg tgcaaaatga tcgccccgat tctggatgaa    240
atcgctgacg aatatcaggg caaactgacc gttgcaaaac tgaacatcga tcaaaaccct    300
ggcactgcgc cgaaatatgg catccgtggt atcccgactc tgctgctgtt caaaaacggt    360
gaagtggcgt cggcaaccaa agtgggtgca ctgtctaaag gtcagttgaa agagttcctc    420
gacgctaacc tggcgtaa                                                   438
```

<210> SEQ ID NO 171
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 171

```
atgagcgata aaattattca cctgactgac gacagttttg acacggatgt actcaaagcg    60
gacggggcga tcctcgtcga tttctgggca gagtggtgcg gtccggcgag ggaggggggct   120 gatggtgcga tttgtggtta taatttggct gcgtcggtta tgctgggtcc gagtgagcgg    180
gtgttttgtc cgctttgtga gcctggtccg tgcaaaatga tcgccccgat tctggatgaa    240
atcgctgacg aatatcaggg caaactgacc gttgcaaaac tgaacatcga tcaaaaccct    300
ggcactgcgc cgaaatatgg catccgtggt atcccgactc tgctgctgtt caaaaacggt    360
gaagtggcgt cggcaaccaa agtgggtgca ctgtctaaag gtcagttgaa agagttcctc    420
gacgctaacc tggcgtaa                                                   438
```

<210> SEQ ID NO 172
<211> LENGTH: 438
<212> TYPE: DNA
<213> ORGANISM: Artificial sequence
<220> FEATURE:
<223> OTHER INFORMATION: derived from TRIP alpha

<400> SEQUENCE: 172

```
atgagcgata aaattattca cctgactgac gacagttttg acacggatgt actcaaagcg    60
gacggggcga tcctcgtcga tttctgggca gagtggtgcg gtccggcgag ggaggggggct   120 gatggtgcga tttgtggtta taatttggct acgttggata tgctgggtcc gagtgagcgg    180
```

```
gtgttttgtc cgctttgtga gcctggtccg tgcaaaatga tcgccccgat tctggatgaa        240
atcgctgacg aatatcaggg caaactgacc gttgcaaaac tgaacatcga tcaaaaccct        300
ggcactgcgc cgaaatatgg catccgtggt atcccgactc tgctgctgtt caaaaacggt        360
gaagtggcgt cggcaaccaa agtgggtgca ctgtctaaag gtcagttgaa agagttcctc        420
gacgctaacc tggcgtaa                                                      438

<210> SEQ ID NO 173
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 173
atgagcgata aaattattca cctgactgac gacagttttg acacggatgt actcaaagcg         60
gacggggcga tcctcgtcga tttctgggca gagtggtgcg gtccgatttg tggttataat        120
ttggctacgt tggttatgct gggtccgagt gagcgggtgt tttgtccgct ttgtgggcct        180
tgtagttctg atatttatga gttgatgggt ccgtgcaaaa tgatcgcccc gattctggat        240
gaaatcgctg acgaatatca gggcaaactg accgttgcaa aactgaacat cgatcaaaac        300
cctggcactg cgccgaaata tggcatccgt ggtatcccga ctctgctgct gttcaaaaac        360
ggtgaagtgg cgtcggcaac caaagtgggt gcactgtcta aggtcagtt gaaagagttc        420 ctcgacgcta acctggcgta a                                                  441

<210> SEQ ID NO 174
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 174
atgagcgata aaattattca cctgactgac gacagttttg acacggatgt actcaaagcg         60
gacggggcga tcctcgtcga tttctgggca gagtggtgcg gtccgatttg tggttataat        120
ttggctatgt cggttatgct gggtccgagt gagcgggtgt tttgtccgct ttgtgagcct        180
tgtagttctg atatttatga gttgatgggt ccgtgcaaaa tgatcgcccc gattctggat        240
gaaatcgctg acgaatatca gggcaaactg accgttgcaa aactgaacat cgatcaaaac        300
cctggcactg cgccgaaata tggcatccgt ggtatcccga ctctgctgct gttcaaaaac        360
ggtgaagtgg cgtcggcaac caaagtgggt gcactgtcta aggtcagtt gaaagagttc        420 ctcgacgcta acctggcgta a                                                  441

<210> SEQ ID NO 175
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 175
atgagcgata aaattattca cctgactgac gacagttttg acacggatgt actcaaagcg         60
gacggggcga tcctcgtcga tttctgggca gagtggtgcg gtccgatttg tggttataat        120
ttggctatgt tggttatgct gggtccgagt gagcgggtgt tttgtccgct ttgtgagcct        180
tgtagttctg atatttatga gttgatgggt ccgtgcaaaa tgatcgcccc gattctggat        240
```

```
gaaatcgctg acgaatatca gggcaaactg accgttgcaa aactgaacat cgatcaaaac      300
cctggcactg cgccgaaata tggcatccgt ggtatcccga ctctgctgct gttcaaaaac      360
ggtgaagtgg cgtcggcaac caaagtgggt gcactgtcta aaggtcagtt gaaagagttc      420
ctcgacgcta acctggcgta a                                                441
```

<210> SEQ ID NO 176
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 176

```
atgagcgata aaattattca cctgactgac gacagttttg acacggatgt actcaaagcg       60
gacggggcga tcctcgtcga tttctgggca gagtggtgcg gtccgatttg tggttataat      120
ttggctacgt cggttatgct gggtccgagt gagcgggtgt tttgtccgct ttgtgagcct      180
tgtagttctg atatttatga gttgatgggt ccgtgcaaaa tgatcgcccc gattctggat      240
gaaatcgctg acgaatatca gggcaaactg accgttgcaa aactgaacat cgatcaaaac      300
cctggcactg cgccgaaata tggcatccgt ggtatcccga ctctgctgct gttcaaaaac      360
ggtgaagtgg cgtcggcaac caaagtgggt gcactgtcta aaggtcagtt gaaagagttc      420
ctcgacgcta acctggcgta a                                                441
```

<210> SEQ ID NO 177
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 177

```
atgagcgata aaattattca cctgactgac gacagttttg acacggatgt actcaaagcg       60
gacggggcga tcctcgtcga tttctgggca gagtggtgcg gtccgatttg tggttataat      120
ttggctatgt tggttatgct gggtccgggt gagcgggtgt tttgtccgct ttgtgagcct      180
tgtagttctg atatttatga gttgatgggt ccgtgcaaaa tgatcgcccc gattctggat      240
gaaatcgctg acgaatatca gggcaaactg accgttgcaa aactgaacat cgatcaaaac      300
cctggcactg cgccgaaata tggcatccgt ggtatcccga ctctgctgct gttcaaaaac      360
ggtgaagtgg cgtcggcaac caaagtgggt gcactgtcta aaggtcagtt gaaagagttc      420
ctcgacgcta acctggcgta a                                                441
```

<210> SEQ ID NO 178
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 178

```
atgagcgata aaattattca cctgactgac gacagttttg acacggatgt actcaaagcg       60
gacggggcga tcctcgtcga tttctgggca gagtggtgcg gtccgatttg tggttataat      120
ttggctacgt tggatatgct gggtccgagt gagcgggtgc tttgtccgct ttgtgagcct      180
tgtagttctg atatttatga gttgatgggt ccgtgcaaaa tgatcgcccc gattctggat      240
```

-continued

```
gaaatcgctg acgaatatca gggcaaactg accgttgcaa aactgaacat cgatcaaaac    300
cctggcactg cgccgaaata tggcatccgt ggtatcccga ctctgctgct gttcaaaaac    360
ggtgaagtgg cgtcggcaac caaagtgggt gcactgtcta aaggtcagtt gaaagagttc    420
ctcgacgcta acctggcgta a                                              441
```

<210> SEQ ID NO 179
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 179

```
atgagcgata aaattattca cctgactgac gacagttttg acacggatgt actcaaagcg     60
gacggggcga tcctcgtcga tttctgggca gagtggtgcg gtccgatttg tggttataat    120
ttggctacgt tggttatgct gggtccgagt gagcgggtgt tttgtccgct ttgtgggcct    180
tgtagtactg atatttatga gttgatgggt ccgtgcaaaa tgatcgcccc gattctggat    240
gaaatcgctg acgaatatca gggcaaactg accgttgcaa aactgaacat cgatcaaaac    300
cctggcactg cgccgaaata tggcatccgt ggtatcccga ctctgctgct gttcaaaaac    360
ggtgaagtgg cgtcggcaac caaagtgggt gcactgtcta aaggtcagtt gaaagagttc    420
ctcgacgcta acctggcgta a                                              441
```

<210> SEQ ID NO 180
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 180

```
atgagcgata aaattattca cctgactgac gacagttttg acacggatgt actcaaagcg     60
gacggggcga tcctcgtcga tttctgggca gagtggtgcg gtccgatttg tggttataat    120
ttggctgcgt tgggtatgct gggtccgagt gagcgggtgt tttgtccgct ttgtgggcct    180
tgtagttctg ataattatga gttgatgggt ccgtgcaaaa tgatcgcccc gattctggat    240
gaaatcgctg acgaatatca gggcaaactg accgttgcaa aactgaacat cgatcaaaac    300
cctggcactg cgccgaaata tggcatccgt ggtatcccga ctctgctgct gttcaaaaac    360
ggtgaagtgg cgtcggcaac caaagtgggt gcactgtcta aaggtcagtt gaaagagttc    420
ctcgacgcta acctggcgta a                                              441
```

<210> SEQ ID NO 181
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 181

```
atgagcgata aaattattca cctgactgac gacagttttg acacggatgt actcaaagcg     60
gacggggcga tcctcgtcga tttctgggca gagtggtgcg gtccgatttg tggttataat    120
ttggctacgt tggctatgct gggtccgagt gcgcgggtgt tttgtccgct ttgtgggcct    180
tgtagttctg atatttatga gttgatgggt ccgtgcaaaa tgatcgcccc gattctggat    240
gaaatcgctg acgaatatca gggcaaactg accgttgcaa aactgaacat cgatcaaaac    300
```

```
cctggcactg cgccgaaata tggcatccgt ggtatcccga ctctgctgct gttcaaaaac    360
ggtgaagtgg cgtcggcaac caaagtgggt gcactgtcta aggtcagtt gaaagagttc     420 ctcgacgcta acctggcgta a                                              441
```

<210> SEQ ID NO 182
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 182

```
atgagcgata aaattattca cctgactgac gacagttttg acacggatgt actcaaagcg    60
gacggggcga tcctcgtcga tttctgggca gagtggtgcg gtccgatttg tggttatgat   120
ttggctatgt tggttatgct gggtccgagt gagcgggtgt tttgtccgct tgtgagcct    180 cgtagttctg atatttatga gttgatgggt ccgtgcaaaa tgatcgcccc gattctggat   240
gaaatcgctg acgaatatca gggcaaactg accgttgcaa aactgaacat cgatcaaaac   300
cctggcactg cgccgaaata tggcatccgt ggtatcccga ctctgctgct gttcaaaaac   360
ggtgaagtgg cgtcggcaac caaagtgggt gcactgtcta aggtcagtt gaaagagttc    420 ctcgacgcta acctggcgta a                                              441
```

<210> SEQ ID NO 183
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 183

```
atgagcgata aaattattca cctgactgac gacagttttg acacggatgt actcaaagcg    60
gacggggcga tcctcgtcga tttctgggca gagtggtgcg gtccgatttg tggttataat   120
ttggctgcgt cggttatgct gggtccgagt gagcgggtgt tttgtccgct tgtgagcct    180 cgtagtcctg atatttatga gttgatgggt ccgtgcaaaa tgatcgcccc gattctggat   240
gaaatcgctg acgaatatca gggcaaactg accgttgcaa aactgaacat cgatcaaaac   300
cctggcactg cgccgaaata tggcatccgt ggtatcccga ctctgctgct gttcaaaaac   360
ggtgaagtgg cgtcggcaac caaagtgggt gcactgtcta aggtcagtt gaaagagttc    420 ctcgacgcta acctggcgta a                                              441
```

<210> SEQ ID NO 184
<211> LENGTH: 441
<212> TYPE: DNA
<213> ORGANISM: Artificial sequence
<220> FEATURE:
<223> OTHER INFORMATION: derived from TRIP alpha

<400> SEQUENCE: 184

```
atgagcgata aaattattca cctgactgac gacagttttg acacggatgt actcaaagcg    60
gacggggcga tcctcgtcga tttctgggca gagtggtgcg gtccgatttg tggttataat   120
ttggctacgt tggatatgct gggtccgagt gagcgggtgt tttgtccgct tgtgagcct    180 tgtagttctg atagttatga gttgatgggt ccgtgcaaaa tgatcgcccc gattctggat   240
gaaatcgctg acgaatatca gggcaaactg accgttgcaa aactgaacat cgatcaaaac   300
```

```
cctggcactg cgccgaaata tggcatccgt ggtatcccga ctctgctgct gttcaaaaac    360
ggtgaagtgg cgtcggcaac caaagtgggt gcactgtcta aggtcagtt gaaagagttc     420 ctcgacgcta acctggcgta a                                              441
```

```
<210> SEQ ID NO 185
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 185
atgagcgata aaattattca cctgactgac gacagttttg acacggatgt actcaaagcg     60
gacggggcga tcctcgtcga tttctgggca gagtggtgcg gtccggcgag ggaggggggct   120 gatggtgcga tttgtggtta taatttggct acgttggtta tgctgggtcc gagtgagcgg   180
gtgttttgtc cgctttgtgg gccttgtagt tctgatattt atgagttgat gggtccgtgc    240
aaaatgatcg ccccgattct ggatgaaatc gctgacgaat atcagggcaa actgaccgtt   300
gcaaaactga acatcgatca aaaccctggc actgcgccga aatatggcat ccgtggtatc   360
ccgactctgc tgctgttcaa aacggtgaa gtggcgtcgg caaccaaagt gggtgcactg   420
tctaaaggtc agttgaaaga gttcctcgac gctaacctgg cgtaa                   465
```

```
<210> SEQ ID NO 186
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 186
atgagcgata aaattattca cctgactgac gacagttttg acacggatgt actcaaagcg     60
gacggggcga tcctcgtcga tttctgggca gagtggtgcg gtccggcgag ggaggggggct   120 gatggtgcga tttgtggtta taatttggct atgtcggtta tgctgggtcc gagtgagcgg   180
gtgttttgtc cgctttgtga gccttgtagt tctgatattt atgagttgat gggtccgtgc    240
aaaatgatcg ccccgattct ggatgaaatc gctgacgaat atcagggcaa actgaccgtt   300
gcaaaactga acatcgatca aaaccctggc actgcgccga aatatggcat ccgtggtatc   360
ccgactctgc tgctgttcaa aacggtgaa gtggcgtcgg caaccaaagt gggtgcactg   420
tctaaaggtc agttgaaaga gttcctcgac gctaacctgg cgtaa                   465
```

```
<210> SEQ ID NO 187
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 187
atgagcgata aaattattca cctgactgac gacagttttg acacggatgt actcaaagcg     60
gacggggcga tcctcgtcga tttctgggca gagtggtgcg gtccggcgag ggaggggggct   120 gatggtgcga tttgtggtta taatttggct atgttggtta tgctgggtcc gagtgagcgg   180
gtgttttgtc cgctttgtga gccttgtagt tctgatattt atgagttgat gggtccgtgc    240
aaaatgatcg ccccgattct ggatgaaatc gctgacgaat atcagggcaa actgaccgtt   300
gcaaaactga acatcgatca aaaccctggc actgcgccga aatatggcat ccgtggtatc   360
```

```
ccgactctgc tgctgttcaa aaacggtgaa gtggcgtcgg caaccaaagt gggtgcactg    420
tctaaaggtc agttgaaaga gttcctcgac gctaacctgg cgtaa                   465
```

<210> SEQ ID NO 188
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 188

```
atgagcgata aaattattca cctgactgac gacagttttg acacggatgt actcaaagcg    60
gacggggcga tcctcgtcga tttctgggca gagtggtgcg gtccggcgag ggaggggggct   120 gatggtgcga tttgtggtta taatttggct acgtcggtta tgctgggtcc gagtgagcgg    180
gtgttttgtc cgctttgtga gccttgtagt tctgatattt atgagttgat gggtccgtgc    240
aaaatgatcg ccccgattct ggatgaaatc gctgacgaat atcagggcaa actgaccgtt    300
gcaaaactga acatcgatca aaaccctggc actgcgccga aatatggcat ccgtggtatc    360
ccgactctgc tgctgttcaa aaacggtgaa gtggcgtcgg caaccaaagt gggtgcactg    420
tctaaaggtc agttgaaaga gttcctcgac gctaacctgg cgtaa                   465
```

<210> SEQ ID NO 189
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 189

```
atgagcgata aaattattca cctgactgac gacagttttg acacggatgt actcaaagcg    60
gacggggcga tcctcgtcga tttctgggca gagtggtgcg gtccggcgag ggaggggggct   120 gatggtgcga tttgtggtta taatttggct atgttggtta tgctgggtcc gggtgagcgg    180
gtgttttgtc cgctttgtga gccttgtagt tctgatattt atgagttgat gggtccgtgc    240
aaaatgatcg ccccgattct ggatgaaatc gctgacgaat atcagggcaa actgaccgtt    300
gcaaaactga acatcgatca aaaccctggc actgcgccga aatatggcat ccgtggtatc    360
ccgactctgc tgctgttcaa aaacggtgaa gtggcgtcgg caaccaaagt gggtgcactg    420
tctaaaggtc agttgaaaga gttcctcgac gctaacctgg cgtaa                   465
```

<210> SEQ ID NO 190
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 190

```
atgagcgata aaattattca cctgactgac gacagttttg acacggatgt actcaaagcg    60
gacggggcga tcctcgtcga tttctgggca gagtggtgcg gtccgacgag ggaggggggct   120 gatggtgcga tttgtggtta taatttggct acgttggata tgctgggtcc gagtgagcgg    180
gtgctttgtc cgctttgtga gccttgtagt tctgatattt atgagttgat gggtccgtgc    240
aaaatgatcg ccccgattct ggatgaaatc gctgacgaat atcagggcaa actgaccgtt    300
gcaaaactga acatcgatca aaaccctggc actgcgccga aatatggcat ccgtggtatc    360
```

```
ccgactctgc tgctgttcaa aaacggtgaa gtggcgtcgg caaccaaagt gggtgcactg      420
tctaaaggtc agttgaaaga gttcctcgac gctaacctgg cgtaa                      465

<210> SEQ ID NO 191
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 191
atgagcgata aaattattca cctgactgac gacagttttg acacggatgt actcaaagcg       60
gacggggcga tcctcgtcga tttctgggca gagtggtgcg gtccggcgag ggagggggct      120
gatggtgcga tttgtggtta taatttggct acgttggtta tgctgggtcc gagtgagcgg      180
gtgttttgtc cgctttgtgg gccttgtagt actgatattt atgagttgat gggtccgtgc      240
aaaatgatcg ccccgattct ggatgaaatc gctgacgaat atcagggcaa actgaccgtt      300
gcaaaactga acatcgatca aaaccctggc actgcgccga atatggcat ccgtggtatc      360 ccgactctgc tgctgttcaa aaacggtgaa gtggcgtcgg caaccaaagt gggtgcactg      420
tctaaaggtc agttgaaaga gttcctcgac gctaacctgg cgtaa                      465

<210> SEQ ID NO 192
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 192
atgagcgata aaattattca cctgactgac gacagttttg acacggatgt actcaaagcg       60
gacggggcga tcctcgtcga tttctgggca gagtggtgcg gtccggcgag ggagggggct      120
gatggtgcga tttgtggtta taatttggct gcgttgggta tgctgggtcc gagtgagcgg      180
gtgttttgtc cgctttgtgg gccttgtagt tctgataatt atgagttgat gggtccgtgc      240
aaaatgatcg ccccgattct ggatgaaatc gctgacgaat atcagggcaa actgaccgtt      300
gcaaaactga acatcgatca aaaccctggc actgcgccga atatggcat ccgtggtatc      360 ccgactctgc tgctgttcaa aaacggtgaa gtggcgtcgg caaccaaagt gggtgcactg      420
tctaaaggtc agttgaaaga gttcctcgac gctaacctgg cgtaa                      465

<210> SEQ ID NO 193
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 193
atgagcgata aaattattca cctgactgac gacagttttg acacggatgt actcaaagcg       60
gacggggcga tcctcgtcga tttctgggca gagtggtgcg gtccggcgag ggagggggct      120
gatggtgcga tttgtggtta taatttggct acgttggcta tgctgggtcc gagtgcgcgg      180
gtgttttgtc cgctttgtgg gccttgtagt tctgatattt atgagttgat gggtccgtgc      240
aaaatgatcg ccccgattct ggatgaaatc gctgacgaat atcagggcaa actgaccgtt      300
gcaaaactga acatcgatca aaaccctggc actgcgccga atatggcat ccgtggtatc      360 ccgactctgc tgctgttcaa aaacggtgaa gtggcgtcgg caaccaaagt gggtgcactg      420
```

```
tctaaaggtc agttgaaaga gttcctcgac gctaacctgg cgtaa            465

<210> SEQ ID NO 194
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 194
atgagcgata aaattattca cctgactgac gacagttttg acacggatgt actcaaagcg     60
gacggggcga tcctcgtcga tttctgggca gagtggtgcg gtccggcgag ggagggggct    120
gatggtgcga tttgtggtta tgatttggct atgttggtta tgctgggtcc gagtgagcgg    180
gtgttttgtc cgctttgtga gcctcgtagt tctgatattt atgagttgat gggtccgtgc    240
aaaatgatcg ccccgattct ggatgaaatc gctgacgaat atcagggcaa actgaccgtt    300
gcaaaactga acatcgatca aaaccctggc actgcgccga atatggcat ccgtggtatc     360 ccgactctgc tgctgttcaa aaacggtgaa gtggcgtcgg caaccaaagt gggtgcactg    420
tctaaaggtc agttgaaaga gttcctcgac gctaacctgg cgtaa                   465

<210> SEQ ID NO 195
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 195
atgagcgata aaattattca cctgactgac gacagttttg acacggatgt actcaaagcg     60
gacggggcga tcctcgtcga tttctgggca gagtggtgcg gtccggcgag ggagggggct    120
gatggtgcga tttgtggtta taatttggct gcgtcggtta tgctgggtcc gagtgagcgg    180
gtgttttgtc cgctttgtga gcctcgtagt cctgatattt atgagttgat gggtccgtgc    240
aaaatgatcg ccccgattct ggatgaaatc gctgacgaat atcagggcaa actgaccgtt    300
gcaaaactga acatcgatca aaaccctggc actgcgccga atatggcat ccgtggtatc     360 ccgactctgc tgctgttcaa aaacggtgaa gtggcgtcgg caaccaaagt gggtgcactg    420
tctaaaggtc agttgaaaga gttcctcgac gctaacctgg cgtaa                   465

<210> SEQ ID NO 196
<211> LENGTH: 465
<212> TYPE: DNA
<213> ORGANISM: Artificial sequence
<220> FEATURE:
<223> OTHER INFORMATION: derived from TRIP alpha

<400> SEQUENCE: 196
atgagcgata aaattattca cctgactgac gacagttttg acacggatgt actcaaagcg     60
gacggggcga tcctcgtcga tttctgggca gagtggtgcg gtccggcgag ggagggggct    120
gatggtgcga tttgtggtta taatttggct acgttggata tgctgggtcc gagtgagcgg    180
gtgttttgtc cgctttgtga gccttgtagt tctgatagtt atgagttgat gggtccgtgc    240
aaaatgatcg ccccgattct ggatgaaatc gctgacgaat atcagggcaa actgaccgtt    300
gcaaaactga acatcgatca aaaccctggc actgcgccga atatggcat ccgtggtatc     360 ccgactctgc tgctgttcaa aaacggtgaa gtggcgtcgg caaccaaagt gggtgcactg    420
```

```
tctaaaggtc agttgaaaga gttcctcgac gctaacctgg cgtaa                    465

<210> SEQ ID NO 197
<211> LENGTH: 42
<212> TYPE: PRT
<213> ORGANISM: Artificial sequence
<220> FEATURE:
<223> OTHER INFORMATION: TRIP alpha

<400> SEQUENCE: 197

Ala Arg Glu Gly Ala Asp Gly Ala Ile Cys Gly Tyr Asn Leu Ala Thr
1               5                   10                  15

Leu Val Met Leu Gly Pro Ser Glu Arg Val Phe Cys Pro Leu Cys Glu
            20                  25                  30

Pro Cys Ser Ser Asp Ile Tyr Glu Leu Met
            35                  40
```